United States Patent
Cohen et al.

(10) Patent No.: US 12,138,272 B2
(45) Date of Patent: Nov. 12, 2024

(54) METHODS AND COMPOSITIONS FOR TREATING AMYOTROPHIC LATERAL SCLEROSIS

(71) Applicant: Amylyx Pharmaceuticals, Inc., Cambridge, MA (US)

(72) Inventors: Joshua Cohen, Canton, MA (US); Justin Klee, Cambridge, MA (US)

(73) Assignee: Amylyx Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 17/742,707

(22) Filed: May 12, 2022

(65) Prior Publication Data
US 2023/0364110 A1 Nov. 16, 2023

(51) Int. Cl.
*A61K 31/575* (2006.01)
*A61K 31/192* (2006.01)
*A61K 38/13* (2006.01)

(52) U.S. Cl.
CPC .......... *A61K 31/575* (2013.01); *A61K 31/192* (2013.01); *A61K 38/13* (2013.01)

(58) Field of Classification Search
None
See application file for complete search history.

(56) References Cited

U.S. PATENT DOCUMENTS

| | | |
|---|---|---|
| 7,737,175 B2 | 6/2010 | Yao et al. |
| 9,632,075 B2 | 4/2017 | Leong et al. |
| 9,872,865 B2 * | 1/2018 | Cohen ............. A61P 21/02 |
| 10,251,896 B2 | 4/2019 | Cohen et al. |
| 10,251,986 B2 * | 4/2019 | Larose ............. A61M 60/237 |
| 10,857,162 B2 * | 12/2020 | Cohen ............. A61P 21/02 |
| 11,071,742 B2 * | 7/2021 | Cohen ............. A61P 39/06 |
| 11,406,625 B2 | 8/2022 | Geva et al. |
| 11,559,533 B2 | 1/2023 | Cohen et al. |
| 2006/0135612 A1 | 6/2006 | Ferrante |
| 2009/0252704 A1 | 10/2009 | Green et al. |
| 2009/0312297 A1 | 12/2009 | Hotamisligil et al. |
| 2011/0142799 A1 | 6/2011 | Glimcher et al. |
| 2012/0157419 A1 | 6/2012 | Gilat et al. |
| 2014/0288030 A1 | 9/2014 | Cohen et al. |
| 2018/0098999 A1 | 11/2018 | Cohen et al. |
| 2018/0362935 A1 | 12/2018 | Wilmer et al. |
| 2019/0255072 A1 | 8/2019 | Cohen et al. |
| 2020/0131236 A1 | 4/2020 | Petsko et al. |
| 2020/0171052 A1 | 6/2020 | Cohen et al. |
| 2020/0179355 A1 | 6/2020 | Geva et al. |
| 2020/0230156 A1 | 7/2020 | Cohen et al. |
| 2021/0030734 A1 | 2/2021 | Geva et al. |
| 2021/0177867 A1 | 6/2021 | Cohen et al. |
| 2021/0186990 A1 | 6/2021 | Cohen et al. |
| 2022/0110948 A1 | 4/2022 | Cohen et al. |
| 2022/0152052 A1 | 5/2022 | Cohen et al. |
| 2022/0152053 A1 | 5/2022 | Coben et al. |
| 2022/0152054 A1 | 5/2022 | Cohen et al. |
| 2022/0152055 A1 | 5/2022 | Cohen et al. |
| 2022/0152056 A1 | 5/2022 | Cohen et al. |
| 2022/0152057 A1 | 5/2022 | Cohen et al. |
| 2022/0152058 A1 | 5/2022 | Cohen et al. |
| 2022/0152059 A1 | 5/2022 | Cohen et al. |
| 2022/0160733 A1 | 5/2022 | Cohen et al. |
| 2023/0277630 A1 | 9/2023 | Cohen et al. |
| 2023/0372263 A1 | 11/2023 | Cohen et al. |

FOREIGN PATENT DOCUMENTS

| | | |
|---|---|---|
| CN | 101048164 | 10/2007 |
| EP | 2422787 | 8/2010 |
| EP | 2255812 | 12/2010 |
| EP | 2599477 | 6/2013 |
| EP | 3016654 | 9/2018 |
| JP | 2005532372 | 10/2005 |
| JP | 2008-518935 | 6/2008 |
| JP | 2011518119 | 6/2011 |
| WO | WO 2004/096123 | 11/2004 |
| WO | WO 2006/050165 | 5/2006 |
| WO | WO 2006/086452 | 8/2006 |
| WO | WO 2009/140265 | 11/2009 |
| WO | WO 2012/160563 | 11/2012 |
| WO | WO 2013/142490 | 9/2013 |
| WO | WO 2014/158547 | 10/2014 |
| WO | WO 2015/001379 | 1/2015 |
| WO | WO 2021/126320 | 6/2021 |
| WO | WO 2023/168280 | 9/2023 |
| WO | WO 2023/224995 | 11/2023 |

OTHER PUBLICATIONS

Appel et al., Arch Neurol 45: 381-396 (Year: 1988).*
Mita et al., Drug Metabolism and Disposition 34(9): 1575-1581 (Year: 2006).*
Kassianides et al., Dig Dis Sci 35(6): 693-697 (Year: 1990).*
Paganoni et al., N Engl. J Med 383: 919-930 (Year: 2020).*
Xu et al., Translational Neurodegeneration 10(29): 1-18 (Year: 2021).*
Amylyx Pharmaceuticals Inc., "Evaluation of the Safety, Tolerability, Efficacy and Activity of AMX0035, a Fixed Combination of Phenylbutyrate (PB) and Tauroursodeoxycholic Acid (TU DCA), for Treatment of(ALS) for the Treatment of ALS Study," Protocol Version 6.0, Jan. 11, 2019, 101 pages.
clinicaltrials.gov, "Open Label Extension Study of AMX0035 in Patients With ALS (CENTAUR-OLE)," dated Apr. 5, 2018, retrieved from URL <https://clinicaltrials.gov/ct2/show/NCT03488524> on Jul. 5, 2022.
CN Office Action in Chinese Appln. No. 201910114290.5, dated Jul. 6, 2022, 11 pages (with English translation).
Kaufmann et al., "The ALSFRSr predicts survival time in an ALS clinic population," Neurology, Jan. 11, 2005, 64(1):38-43.

(Continued)

*Primary Examiner* — Phuong Huynh
(74) *Attorney, Agent, or Firm* — Fish & Richardson P.C.

(57) ABSTRACT

Provided herein are methods for treating at least one symptom of ALS in a subject who has received a first dosage of BSEP inhibitor, the method including administering to the subject a composition comprising a bile acid or a pharmaceutically acceptable salt thereof and a phenylbutyrate compound, monitoring the subject for response to the B SEP inhibitor, and administering a second dosage of the BSEP inhibitor, wherein the second dosage is less than the first dosage.

11 Claims, No Drawings

(56) References Cited

OTHER PUBLICATIONS

PCT International Preliminary Report on Patentability in International Appln. No. PCT/US2020/048581, dated May 17, 2022, 9 pages.
alstreatment.com, "ALS and Constipation: Causes and Management of This Symptom," Aug. 2019, retrieved Mar. 21, 2022 from URL <https://alstreatment.com/constipation-als-symptom/>, 5 pages.
CA Office Action in Canadian Appln. No. 2,908,683, dated May 16, 2022, 4 pages.
Hogarth et al., "Sodium phenylbutyrate in Huntington's disease: A dose-finding study," Movement Disorders, Oct. 15, 2007, 22(13):1962-4.
JP Japanese Office Action in Japanese Appln. No. 2022-085433, dated Aug. 9, 2022, 13 pages (with English translation).
clinicaltrials.gov, "NCT02437110, HERV-K Suppression Using Antiretroviral Therapy in Volunteers With Amyotrophic Lateral Sclerosis (ALS)," dated Oct. 19, 2020, retrieved Oct. 26, 2022 from URL <https://clinicaltrials.gov/ct2/show/NCT02437110>, 10 pages.
Iiagos et al., "Assessment of the role of renal organic anion transporters in drug-induced nephrotoxicity," Toxins, Aug. 9, 2010, 2(8):2055-82.
Hill et al., "Tenofovir alafenamide versus tenofovir disoproxil fumarate: is there a true difference in efficacy and safety?," Journal of Virus Eradication, Apr. 1, 2018, 4(2):72-9.
Kohler et al., "Tenofovir renal proximal tubular toxicity is regulated By OAT1 and MRP4 transporters," Laboratory Investigation, Jun. 2011, 91(6):852-8.
Sevenler et al., "Immunoassay for HIV Drug Metabolites Tenofovir and Tenofovir Diphosphate," ACS Infectious Diseases, May 11, 2020, 6(7):1635-42.
[No Author] "Safety and Efficacy of TR019622 as add-on Therapy to Riluzole Versus Placebo in Treatment of Patients Suffering From ALS (Mitotarget)," U.S. Library of Medicine, Mar. 24, 2009, NCT00868166.
[No Author] "Experimental Alzheimer Drugs Targeting Beta-Amyloid and the Amyloid Hypothesis," Alzheimer's Associate, 2007, 3 pages.
[No Author] "Know the 10 Signs, Early Detection Matters," Alzheimer's Association, 2009, 2 pages.
[No Author] "Alzheimer's Disease and Type 2 Diabetes: What is the Link?" Alzheimer's Association, 2011, 3 pages.
Abe et al., "Confirmatory double-blind, parallel-group, placebo-controlled study of efficacy and safety of edaravone (MCI-186) in amyotrophic lateral sclerosis patients," Amyotrophic Lateral Sclerosis and Frontotemporal Degeneration, Dec. 1, 2014, 15(7-8):610-7.
Abe et al., "Safety and efficacy of edaravone in well defined patients with amyotrophic lateral sclerosis: a randomised, double-blind, placebo-controlled trial," The Lancet Neurology, Jul. 1, 2017, 16(7):505-12.
Afanas'ev, "Signaling and Damaging Functions of Free Radicals in Aging—Free Radical Theory, Hormesis, and TOR," Aging and Dis., Oct. 2010, 1(2):75-88.
Al-Chalabi et al., "Amyotrophic lateral sclerosis: moving towards a new classification system," The Lancet Neurology, Oct. 1, 2016, 15(11):1182-94.
Al-Chalabi et al., "Protocol for a double-blind randomised placebo-controlled trial of lithium carbonate in patients with amyotrophic Lateral Sclerosis," BMC Neurology, 2011, 11:111, 13 pages.
Aldini et al., "Relationship between structure and intestinal absorption of bile acids with a steroid or side-chain modification," Steroids, 1996, 61:590-597.
ALS Utangled Group, "ALSUntangled No. 25: Ursodiol," Amyotroph Lateral Scler Frontotemporal Degener., 2014, 15(5-6):475-478.
Alshikho et al., "Integrated magnetic resonance imaging and [11C]-PBR28 positron emission tomographic imaging in amyotrophic lateral sclerosis," Annals of Neurology, Jun. 2018, 83(6):1186-97, 39 pages.
ALSOD, "Amyotrophic Lateral Sclerosis online Database," retrieved Nov. 12, 2020 from URL <https://alsod.ac.uk/>, 1 pages.
alstreatment.com, "ALS and Constipation: Causes and Management of This Symptom," Aug. 2019, retrieved Mar. 21, 2022 from URL <https://alstreatment.com/constipation-als-symptom/2, 5 pages.
alzforum.org, "In ALS, Respiratory Measure Predicts Pace of Disease," Dec. 1, 2017, retrieved Apr. 27, 2022 from URL <https://www.alzforum.org/news/research-news/als-respiratory-measure-predicts-pace-disease>, 5 pages.
Amaral et al., "Bile acids: regulation of apoptosis by ursodeoxycholic Acid," J Lipid Res., 2009, 50:1721-1734.
Andersen et al., "Clinical genetics of amyotrophic lateral sclerosis: what do we really know?," Nature Reviews Neurology, Nov. 2011, 7(11):603-15.
Andersen et al., "EFNS guidelines on the Clinical Management of Amyotrophic Lateral Sclerosis (MALS)—revised report of an EFNS task force," European Journal Neurology, 2012, 19:360-375.
Andres et al., "Developing normalized strength scores for neuromuscular research," Muscle & Nerve, Feb. 2013, 47(2):177-82.
Andres et al., "Fixed dynamometry is more sensitive than vital capacity or ALS rating scale," Muscle & Nerve, Oct. 2017, 56(4):710-5, 28 pages.
Andres et al., "Quantitative motor assessment in amyotrophic lateral sclerosis," Neurology, Jul. 1, 1986, 36(7):937-41.
Andres et al., "Validation of a new strength measurement device for amyotrophic lateral sclerosis clinical trials," Muscle & Nerve, Jan. 2012, 45(1):81-5.
Archibald et al., "Identification of improved clinical outcomes and creatinine sparing effect of dexpramipexole based on significant inter-study differences in the phase 2 and phase 3 (Empower) clinical trials in ALS," Amyotrophic Lateral Sclerosis and Frontotemporal Degeneration, Nov. 4, 2013, 14:46-7.
Atassi et al., "The PRO-ACT database: design, initial analyses, and predictive features," Neurology, Nov. 4, 2014, 83(19):1719-25.
AU Office Action in Australian Application No. 2014242123, dated Feb. 22, 2018, 4 pages.
AU Office Action in Australian Appln. No. 2019200658, dated Mar. 13, 2020, 8 pages.
AusPAR, "Extract from the Clinical Evaluation Report for Sodium phenylbutyrate," Jan. 19, 2017, 85 pages.
Axcan Pharma US Inc .: Treatment of Patients With All Stages of Primary Biliary Cirrhosis; URSO (ursodiol) Tablets, 250 mg; Medical Officer's Review; NDA 20-675; Mar. 26, 1996.
Bakker et al., "Assessment of the factorial validity and reliability of the ALSFRS-R: a revision of its measurement model," Journal of Neurology, Jul. 1, 2017, 264(7):1413-20.
Balendra et al., "C9orf72-mediated ALS and FTD: multiple pathways to disease," Nature Reviews Neurology, Sep. 2018, 14(9):544-58.
Basseri et al., "The chemical chaperone 4-phenylbutyrate inhibits adipogenesis by modulating the unfolded protein response," J Lipid Res., 2009, 50:2486-2501.
Bensimon et al., "ALS/Riluzole Study Group. A controlled trial of riluzole in amyotrophic lateral sclerosis," New England Journal of Medicine, Mar. 3, 1994, 330(9):585-91.
Berger et al., "Structure-function analysis of the tertiary bile acid TUDCA for the resolution of endoplasmic reticulum stress in intestinal epithelial cells," Biochemical and Biophysical Research Communications, 2011, 409:610-615.
Bernard-Marissal et al., "Endoplasmic reticulum and mitochondria in diseases of motor and sensory neurons: a broken relationship?," Cell Death & Disease, Feb. 28, 2018, 9(3):1-6.
Berry et al., "Design and Initial Results of a Multi-Phase Randomized Trial of Cefuiaxone in Amyotrophic Lateral Sclerosis," PLoS One. 2013; 8(4):e611177.
Berry et al., "Predicting success: optimizing phase II ALS trials for the transition to phase III," Amyotrophic Lateral Sclerosis and Frontotemporal Degeneration, Mar. 1, 2014, 15(1-2):1-8.
Berry et al., "The Combined Assessment of Function and Survival (CAFS): a new endpoint for ALS clinical trials," Amyotrophic Lateral Sclerosis and Frontotemporal Degeneration, Apr. 1, 2013, 14(3):162-8.
Berthod et al., "In vivo and in vitro models to study amyotrophic lateral sclerosis," Amyotrophic Lateral Sclerosis, Jan. 20, 2012, 81.

(56) References Cited

OTHER PUBLICATIONS

Bhandary et al., "An involvement of oxidative stress in endoplasmic reticulum stress and its associated diseases," International Journal of Molecular Sciences, Jan. 2013, 14(1):434-56.
Biosciences Inc., "Phenylbutyrate Na Inducer, Catalog# SIH-255," StressMarq, 2011, 2 pages.
Birks, "Donepezil for dementia due to Alzheimer's disease (Review)," 2009, 75 pages.
Boylan et al., "Immunoreactivity of the phosphorylated axonal neurofilament H subunit (pNF-H) in blood of ALS model rodents and ALS patients: evaluation of blood pNF-H as a potential ALS biomarker," Journal of Neurochemistry, Dec. 2009, 111(5):1182-91.
Brooks et al., "El Escorial revisited: revised criteria for the diagnosis of amyotrophic lateral sclerosis," Amyotrophic Lateral Sclerosis and Other Motor Neuron Disorders, Jan. 1, 2000, 1(5):293-9.
Brown et al., "Amyotrophic lateral sclerosis," New England Journal of Medicine, Jul. 13, 2017, 377(2):162-72.
Byrne et al., "Rate of familial amyotrophic lateral sclerosis: a systematic review and meta-analysis," Journal of Neurology, Neurosurgery & Psychiatry, Jun. 1, 2011, 82(6):623-7.
CA Office Action in Canadian Appln. No. 2,908,683, dated Mar. 12, 2020, 5 pages.
CA Office Action in Canadian Appln. No. 2,908,683, dated Oct. 22, 2020, 4 pages.
Carducci et al., "Phenylbutyrate Induces Apoptosis in Human Prostate Cancer and Is More Potent Than Phenylacetate," Clin Canc Res., Feb. 1996, 2:379-387.
Carri et al., "Targets in ALS: designing multidrug therapies," Trends in Pharmacological Sciences, May 1, 2006, 27(5):267-73.
Castro et al., "The Bile Acid Tauroursodeoxycholic Acid Modulates Phosphorylation and Translocation of Bad via Phosphatidylinositol 3-Kinase in Glutamate-Induced Apoptosis of Rat Cortical Neurons," JPET, 2004, 311:845-852.
Cedarbaum et al., "Bdnf Als Study Group, 1A complete listing of the BDNF Study Group. The ALSFRS-R: a revised ALS functional rating scale that incorporates assessments of respiratory function," Journal of the Neurological Sciences, Oct. 31, 1999, 169(1-2):13-21.
Chen et al., "Assessment of a multiple biomarker panel for diagnosis of amyotrophic lateral sclerosis," BMC Neurology, Dec. 2016, 16(1):1-7.
Chiu et al., "Hepatitis C Virus Infection Increases the Risk of Alzheimer's Diseases: A Population-Based Cohort Study in Taiwan," Poster, 2013, 1 page.
Cho et al., "4-Phenylbutyrate attenuates the ER stress response and cyclic AMP accumulation in DYT1 dystonia cell models," PLoS One, Nov. 7, 2014, 9(11):e110086.
Clerc et al., "A look into the future of ALS research," Drug Discovery Today, Jun. 1, 2016, 21(6):939-49.
Clinical Trials.gov: "Efficacy and Tolerability of Tauroursodeoxycholic Acid in Amyotrophic Lateral Sclerosis (TUDCA-ALS)", ClinicalTrials. gov, Mar. 23, 2012, 22 pages.
clinicaltrials.gov, ID NCT03127514, "AMX0035 in Patients With Amyotrophic Lateral Sclerosis (ALS) (CENTAUR)," updated Mar. 5, 2019, retrieved Nov. 5. 2020 from URL <https://clinicaltrials. gov/ct2/show/NCT03127514>, 6 pages.
CN Office Action Chinese Application No. 201480017771X, First Office Action, dated Dec. 14, 2016, 13 pages (with translation).
CN Office Action in Chinese Application No. 201480017771.X, dated Feb. 24, 2018, 10 pages (with English translation).
CN Office Action in Chinese Application No. 201480017771.X, dated Nov. 8, 2018, 15 pages (with English translation).
CN Office Action in Chinese Appln. No. 201910114290.5, dated Jan. 26, 2022, 9 pages (with English translation).
CN Office Action in Chinese Appln. No. 2019101142905, dated May 8, 2021, 18 pages (with English translation).
Cohen J, et al. Poster presented at: 2019 MDA Clinical and Scientific Conference; Apr. 13-17, 2019; Orlando, FL.
Cohen J, et al. Poster presented at: 28th International Symposium for ALS/MND; Dec. 4-10, 2017; Boston, MA, 1 page.
Cudkowicz et al., "Dexpramipexole versus placebo for patients with amyotrophic lateral sclerosis (Empower): a randomised, double-blind, phase 3 trial," The Lancet Neurology, Nov. 1, 2013, 12(11):1059-67.
Cudkowicz et al., "Phase 2 study of sodium phenylbutyrate in ALS," Amyotrophic Lateral Sclerosis, Jan. 1, 2009, 10(2):99-106.
Cudkowicz et al., "Safety and efficacy of ceftriaxone for amyotrophic lateral sclerosis: a multi-stage, randomised, double-blind, placebo-controlled trial," The Lancet Neurology, Nov. 1, 2014, 13(11):1083-91.
Daghlas et al., "A retrospective investigation of the relationship between baseline covariates and rate of ALSFRS-R decline in ALS clinical trials," Amyotrophic Lateral Sclerosis and Frontotemporal Degeneration, Apr. 3, 2018, 19(3-4):206-11.
Daniells, "Dairy could mask bitter taste of antioxidants," Food Navigator, May 27, 2009, 2 pages.
De Schaepdryver et al., "Comparison of elevated phosphorylated neurofilament heavy chains in serum and cerebrospinal fluid of patients with amyotrophic lateral sclerosis," Journal of Neurology, Neurosurgery & Psychiatry, Apr. 1, 2018, 89(4):367-73.
De Schaepdryver et al., "Serum neurofilament heavy chains as early marker of motor neuron degeneration," Annals of Clinical and Translational Neurology, Oct. 2019, 6(10):1971-9.
Del Signore et al., "Combined riluzole and sodium phenylbutyrate therapy in transgenic amyotrophic lateral sclerosis mice," Amyotrophic Lateral Sclerosis, Jan. 1, 2009, 10(2):85-94.
Dionísio et al., "Amyloid-β pathology is attenuated by tauroursodeoxycholic acid treatment in APP/PS1 mice after disease onset," Neurobiology of Aging, Jan. 1, 2015, 36(1):228-40.
D'Ovidio et al., "Association between alcohol exposure and the risk of amyotrophic lateral sclerosis in the Euro-Motor study," Journal of Neurology, Neurosurgery & Psychiatry, Jan. 1, 2019, 90(1):11-9.
Duan W-M et al.: "Tauroursodeoxycholic acid improves the survival and function of nigral transplants in a rat model of Parkinson's disease", Cell Transplantation, Jan. 1, 2002, 11(3):195-205.
Dupuis et al.,"A Randomized, Double Blind, Placebo-Controlled Trial of Pioglitazone in Combination with Riluzole in Amyotrophic Lateral Sclerosis," PLoS One, 7(6):e37885, 7 pages.
Eckert et al., "Mitochondrial dysfunction—the beginning of the end in Alzheimer's disease? Separate and synergistic modes of tau and amyloid-β toxicity," Alzheimer's Res Therapy, 2011, 3:15, 11 pages.
Elia et al., "Tauroursodeoxycholic acid in the treatment of patients with amyotrophic lateral sclerosis," European Journal of Neurology, Jan. 2016, 23:45-52.
Engin et al., "Restoring endoplasmic reticulum function by chemical chaperones: an emerging therapeutic approach for metabolic diseases", Diabetes, Obesity and Metabolism, 2010, vol. 12, No. (Suppl. 2), pp. 108-115.
EP European Search Report in European Application No. 14775675. 3, dated Nov. 7, 2016, 12 pages.
EP European Search Report in European Application No. 20169399. 1, dated Nov. 6, 2020, 12 pages.
EP Notices of Opposition in European Appln. No. 14775675.3, dated Feb. 2, 2021, 29 pages.
fda.gov, "Amyotrophic Lateral Sclerosis: Developing Drugs for Treatment—Guidance for Industry," Washington, DC: US Food and Drug Administration, retrieved Nov. 3, 2020, from URL <https:// www.fda.gov/regulatory-information/search-fda-guidance-documents/ amyotrophic-lateral-sclerosis-developing-drugs-treatment-guidance-industry>, 11 pages.
Feneberg et al., "Multicenter evaluation of neurofilaments in early symptom onset amyotrophic lateral sclerosis," Neurology, Jan. 2, 2018, 90(1):e22-30.
Franck et al., "Hepatitis C Virus NS2 Protein Is Phosphorylated by the Protein Kinase CK2 and Targeted for Degradation to the Proteasome," J Virol., Mar. 2005, 79(5):2700-2708.
Friedlich and Butcher, "Peer Commentary: Involvement of Free Oxygen Radicals in β-Amyloidosis: An Hypothesis," Neurobiol of Aging, 1994, 15(4):443-445.
Fujimura-Kiyono et al., "Onset and spreading patterns of lower motor neuron involvements predict survival in sporadic amyo-

(56) References Cited

OTHER PUBLICATIONS trophic lateral sclerosis," Journal of Neurology, Neurosurgery & Psychiatry, Nov. 1, 2011, 82(11):1244-9.
Fukui, "Reactive oxygen species induce neurite degeneration before induction of cell death," Journal of Clinical Biochemistry and Nutrition, Mar. 23, 2016, 16-34.
Ganesalingam et al., "pNfH is a promising biomarker for ALS," Amyotrophic Lateral Sclerosis and Frontotemporal Degeneration, Mar. 1, 2013, 14(2):146-9.
Geula et al., "Aging renders the brain vulnerable to amyloid β-protein neurotoxicity," Nature Med., Jul. 1998, 4(7):827-831.
Gibson and Shi, "A Mitocentric View of Alzheimer's Disease Suggests Multi-Faceted Treatments," J Alzheimer's Dis., 2010, 20(2):S591-S607 (Author Manuscript).
Gille et al., "Serum neurofilament light chain levels as a marker of upper motor neuron degeneration in patients with amyotrophic lateral sclerosis," Neuropathology and Applied Neurobiology, Apr. 2019, 45(3):291-304.
Goh et al., "Phenylbutyrate Attenuates the Expression of Bcl-XL, DNA-PK, Caveolin-1, and VEGF in Prostate Cancer Cells," Neoplasia, 2001, 3(4):331-338.
Gordon et al., "Progression in ALS is not linear but is curvilinear," J Neurol, 2010, 257:1713-1717.
Hardiman et al., "Amyotrophic lateral sclerosis," Nature Reviews Disease Primers, Oct. 5, 2017, 3(1):1-9.
Hardiman et al., "Edaravone: a new treatment for ALS on the horizon?," The Lancet Neurology, Jul. 1, 2017, 16(7):490-1.
Hayashi et al., "4-Phenylbutyrate Enhances the Cell Surface Expression and the Transport Capacity of Wild-Type and Mutated Bile Salt Export Pumps," Hepatol., 2007, 45:1506-1516.
Hayashi et al., "Short-Chain Ubiquitination is Associated with the Degradation Rate of a Cell-Surface-Resident Bile Salt Export Pump (BSEP/ABCB11)," Mol Pharmacol., 2009, 75:143-150.
Hebert, "Contributions of hepatic and intestinal metabolism and P-glycoprotein to cyclosporine and tacrolimus oral drug delivery," Advanced Drug Delivery Reviews, Sep. 15, 1997, 27(2-3):201-14.
Ho et al., "Endoplasmic Reticulum Stress Induces Tau Pathology and Forms a Vicious Cycle: Implication in Alzheimer's Disease Pathogenesis," J Alzheimer's Dis., 2012, 28:839-854.
Hoozemans et al., "The Unfolded Protein Response is Activated in Pretangle Neurons in Alzheimer's Disease Hippocampus," Am J Pathol., Apr. 2009, 174(4):1241-1251.
Hou et al., "Screening of SOD1, FUS and TARDBP genes in patients with amyotrophic lateral sclerosis in central-southern China," Scientific Reports Sep. 8, 2016, 6(1):1-7.
Huang and Jiang, "Accumulated Amyloid-β Peptide and Hyperphosphorylated Tau Protein: Relationship and Links in Alzheimer's Disease," J Alzheimer's Dis., 2009, 16:15-27.
Iannitti et al., "Clinical and experimental applications of sodium phenylbutyrate," Drugs in R&D, Sep. 2011, 11(3):227-49.
Inagi, "Endoplasmic Reticulum: The Master Regulator of Stress Responses in Glomerular Diseases," Intechopen, 2011, 21 pages.
Jaiswal, "Riluzole and edaravone: A tale of two amyotrophic lateral sclerosis drugs," Medicinal Research Reviews, Mar. 2019, 39(2):733-48.
Jaronen et al., "ER stress and unfolded protein response in amyotrophic lateral sclerosis—A controversial role of protein disulphide isomerase," Frontiers in Cellular Neuroscience, Dec. 2, 2014, 8:402, 6 pages.
JP Japanese Office Action in Japanese Appln. No. 2020-155505, dated Aug. 31, 2021, 10 pages (with English translation).
JP Japanese Patent Application No. 2016-505464, First Office Action dated Oct. 3, 2017 and translation, 6 pages.
JP Office Action in Japanese Application No. 2016-505464, dated Feb. 27, 2018, 5 pages (with English translation).
JP Office Action in Japanese Application No. 2016-505464, dated Oct. 30, 2018, 6 pages (with English translation).
JP Office Action in Japanese Appln. No. 2019-040563, dated Jan. 21, 2020, 10 pages (with English translation).
Kasarskis et al., "Rating the severity of ALS by caregivers over the telephone using the ALSFRS-R," Amyotrophic Lateral Sclerosis, Mar. 1, 2005, 6(1):50-4.
Kaufmann et al., "Excellent inter-rater, intra-rater, and telephone-administered reliability of the ALSFRS-R in a multicenter clinical trial," Amyotrophic Lateral Sclerosis, Jan. 1, 2007, 8(1):42-6.
Kaur et al., "Proteomic profile of 4-PBA treated human neuronal cells during ER stress," Molecular Omics, Jan. 4, 2018, 14(1):53-63.
Keene, CD et al.: "Tauroursodeoxycholic acid, a bile acid is neuroprotective in a transgenic animal model of Huntington's disease", PNAS, vol. 99, No. 16, Aug. 6, 2002, pp. 10671-10676.
Kiernan et al., "Amyotrophic lateral sclerosis," The Lancet, Mar. 12, 2011, 377(9769):942-55.
Kim et al., "Clinical Pharmacology and Biopharmaceutics Review(s)," Center for Drug Evaluation and Research, Dec. 11, 2011-Aug. 23, 2012, 89 pages.
Kimura et al., "Progression rate of ALSFRS-R at time of diagnosis predicts survival time in ALS," Neurology, Jan. 24, 2006, 66(2):265-7.
Kitamoto et al., "Amyloid Plaques in Creutzfeldt-Jakob Disease Stain with Prion Protein Antibodies," Ann Neurol., 1986, 20:204-208.
Knibb et al., "A clinical tool for predicting survival in ALS," Journal of Neurology, Neurosurgery & Psychiatry, Dec. 1, 2016, 87(12):1361-7.
KR Office Action in Korean Appln. No. 10-2015-7030684, dated Apr. 7, 2020, 8 pages (with English translation).
KR Office Action in Korean Appln. No. 10-2021-7005747 dated May 6, 2021, 7 pages (with English translation).
KR Office Action in Korean Appln. No. 10-2021-7005747 dated Nov. 15, 2021, 9 pages (with English translation).
Kusaczuk, "Tauroursodeoxycholate—Bile Acid with Chaperoning Activity: Molecular and Cellular Effects and Therapeutic Perspectives," Cells, Dec. 2019, 8(12):1471.
Labra et al., "Rate of disease progression: a prognostic biomarker in ALS," Journal of Neurology, Neurosurgery & Psychiatry, Jun. 1, 2016, 87(6):628-32.
Lacomblez et al., "Dose-ranging study of riluzole in amyotrophic lateral sclerosis," The Lancet, May 25, 1996, 347(9013):1425-31.
Leigh et al., "Amyotrophic lateral sclerosis: a consensus viewpoint on designing and implementing a clinical trial," ALS and other motor neuron disorders, 2004, 5:84-98.
Lindholm et al., "ER stress and neurodegenerative diseases," Cell Death Differentiation, 2006, 13:385-392.
Lingor et al., "ROCK-ALS: Protocol for a Randomized, Placebo-controlled, Double-Blind Phase IIa Trial of Safety, Tolerability and Efficacy of the Rho Kinase (ROC Inhibitor Fasudil in Amyotrophic Lateral Sclerosis," Frontiers in Neurology, 2019, 10(293):1-11.
Liu et al., "Energy homeostasis and abnormal RNA metabolism in amyotrophic lateral sclerosis," Frontiers in Cellular Neuroscience, May 4, May 4, 2017, 11:126, 15 pages.
Liu et al., "The peroxisome proliferator phenylbutyric acid (PBA) protects astrocytes from ts1 MoMuL V-induced oxidative cell death," Journal of Neurovirology, Jan. 2002, 8(4): 318-325.
Lu et al., "Plasma neurofilament heavy chain levels correlate to markers of late stage disease progression and treatment response in SOD1 G93A mice that model ALS," PLoS One, Jul. 16, 2012, 7(7):e40998, 13 pages.
Manfredi et al., "Mitochondria and endoplasmic reticulum crosstalk in amyotrophic lateral sclerosis," Neurobiology of Disease, Jun. 1, 2016, 90:35-42.
Marlatt et al., "Alzheimer's Disease: Cerebrovascular Dysfunction, Oxidative Stress, an Advanced Clinical Therapies," J Alzheimers Dis., 2009, 15(2):199-2010.
Marzioni et al., "Ca2+-Dependent Cytoprotective Effects of Ursodeoxycholic and Tauroursodeoxycholic Acid on the Biliary Epithelium in a Rat Model of Cholestasis and Loss of Bile Ducts," Am J Pathol., Feb. 2006, 168(2):398-409.
Material Safety Data Sheet, "Sodium Phenylbutyrate: sc-200652," May 2010, 3 pages.

(56) References Cited

OTHER PUBLICATIONS

Maurer M: "Amyotrophic Lateral Sclerosis: An Introduction to Treatment and Trials", Amyotrophic Lateral Sclerosis, Prof. Martin Maurer (Ed.), ISBN: 978-953-307-806-9, InTech, Jan. 20, 2012.
McCombe et al., "Serial measurements of phosphorylated neurofilament-heavy in the serum of subjects with amyotrophic lateral sclerosis," Journal of the Neurological Sciences, Jun. 15, 2015, 353(1-2):122-9.
Mehta et al., "Targeting mitochondrial dysfunction in amyotrophic lateral sclerosis: a systematic review and meta-analysis," Brain Communications, Apr. 6, 2019, 1(1):fcz009, 14 pages.
Miki et al., "Endoplasmic reticulum stress in diabetic hearts abolishes erythropoietin-induced myocardial protection by impairment of phospho-glycogen synthase kinase-3$\beta$-mediated suppression of mitochondrial permeability transition", Diabetes, 2009, vol. 58, pp. 2863-2872.
Min J-H et al.: "Oral solubilized Ursodeoxycholic acid therapy in Amyotrophic Lateral Sclerosis: A randomized cross-over trial", The Journal of Korean Medical Science, vol. 27, No. 2, Jan. 27, 2012.
Moore et al., "WALS Study Group, ALS Care Study Group. ALSFRS as a measure of disease progression and survival," Amyotrophic Lateral Sclerosis Other Motor Neuron Disorders, 2003, 4:42-50.
Mosbah et al., "Endoplasmic reticulum stress inhibition protects steatotic and non-steatotic livers in partial hepatectomy under ischemia-reperfusion," Cell Death Dis., 2010, 12 pages.
Mousavi et al., "Pulmonary function tests in patients with amyotrophic lateral sclerosis and the association between these tests and survival," Iranian Journal of Neurology, Jul. 4, 2014, 13(3):131-7.
Muhammad et al., "Reactive Oxygen Species in Diabetes-induced Vascular Damage, Stroke, and Alzheimer's Disease," J Alzheimer's Dis., 2009, 16:775-785.
Mulder et al., "Familial adult motor neuron disease: amyotrophic lateral sclerosis," Neurology, Apr. 1986, 36(4):511-7.
Neals, Central Institutional Review Board (cIRB), "Northeast Amyotrophic Lateral Sclerosis Consortium," retrieved Nov. 12, 2020 from URL <https://www.neals.org/for-als-researchers/central-irb-master-contracts/>, 4 pages.
Neurology, "Taurursodiol-Phenylbutryate Investigational Treatment for Amyotrophic Lateral Sclerosis Targets Neurodegeneration," Oct. 30, 2019, 3 pages (abstract only).
Niederwolfsgruber et al., "The Production of the Alzheimer Amyloid Precursor Protein (APP) in Extraneuronal Tissue Does Not Increase in Old Age," J Gerontol: Biol Sci., 1998, 53A(3):B186-B190.
Nunes et al., "TUDCA, a Bile Acid, Attenuates Amyloid Precursor Protein Processing and Amyloid-$\beta$ Deposition in APP/PS1 Mice," Mol Neurobiol., 2012, 15 pages.
Oskarsson et al., "Amyotrophic lateral sclerosis: an update for 2018," Mayo Clinic Proceedings, Nov. 1, 2018, 93(11):1617-28.
Paganoni et al., "Diagnostic timelines and delays in diagnosing amyotrophic lateral sclerosis (ALS)," Amyotrophic Lateral Sclerosis and Frontotemporal Degeneration, Sep. 1, 2014, 15(5-6):453-6.
Paganoni et al., "Outcome measures in amyotrophic lateral sclerosis clinical trials," Clinical Investigation, 2014, 4(7):605-18.
Paganoni et al., "Trial of Sodium Phenylbutyrate-Taurursodiol for Amyotrophic Lateral Sclerosis," New England Journal of Medicine, Sep. 3, 2020, 383(10):919-30.
Paolini et al., "Bile acid structure and selective modulation of murine hepatic cytochrome P450-linked enzymes," Hepatology, Sep. 1999, 30(3):730-9.
Paolini et al., "Ursodeoxycholic acid (UDCA) prevents DCA effects on male mouse liver via up-regulation of CXP and preservation of BSEP activities," Hepatology, Aug. 2002, 36(2):305-14.
Parry GJ et al.: "Safety, tolerability, and cerebrospinal fluid penetration of Ursodeoxycholic Acid in patients with Amyotrophic Lateral Sclerosis", Clinical Neuropharmacology, Jan./Feb. 2010, 33(1):17-21.
Pawlitzki et al., "CSF neurofilament light chain levels in primary progressive MS: signs of axonal neurodegeneration," Frontiers in Neurology, Dec. 14, 2018, 9:1037.

PCT International Preliminary Report on Patentability in International Application No. PCT/US2014/018040, dated Sep. 29, 2015, 8 pages.
PCT International Search Report and Written Opinion dated Jun. 24, 2014 for International Appln. No. PCT/US2014/018040, 10 pgs.
PCT International Search Report and Written Opinion in International Appln. No. PCT/US2020/048581, dated Dec. 3, 2020, 16 pages.
PCT International Search Report and Written Opinion in International Appln. No. PCT/US2020/065145, dated Mar. 16, 2021, 12 pages.
Peters et al., "Emerging mechanisms of molecular pathology in ALS," Journal of Clinical Investigation, Jun. 11, 2015, 125(6), 2548, 1 page.
Petrov et al., "ALS clinical trials review: 20 years of failure. Are we any closer to registering a new treatment?," Frontiers in Aging Neuroscience, Mar. 22, 2017, 9:68, 11 pages.
Pfohl et al., "Unraveling the complexity of amyotrophic lateral sclerosis survival prediction," Frontiers in Neuroinformatics, Jun. 14, 2018, 12:36, 13 pages.
Pisa et al., "Hospitalizations due to respiratory failure in patients with amyotrophic lateral sclerosis and their impact on survival: a population-based cohort study," BMC Pulmonary Medicine, Dec. 2016, 16(1):1-9.
Poesen et al., "Diagnostic and prognostic performance of neurofilaments in ALS," Frontiers in Neurology, Jan. 18, 2019, 9:1167, 7 pages.
Pogocki, "Alzheimer's $\beta$-amyloid peptide as a source of neurotoxic free radicals: the role of structural effects," Acta Neurobiol Exp., 2003, 63:131-145.
Polkey et al., "Respiratory muscle strength as a predictive biomarker for survival in amyotrophic lateral sclerosis," American Journal of Respiratory and Critical Care Medicine, Jan. 1, 2017, 195(1):86, 48 pages.
Pottier et al., "Genetics of FTLD: overview and what else we can expect from genetic studies," Journal of Neurochemistry, Aug. 2016, 138:32-53, 59 pages.
Proudfoot et al., "The ALSFRS as an outcome measure in therapeutic trials and its relationship to symptom onset," Amyotrophic Lateral Sclerosis and Frontotemporal Degeneration, Aug. 17, 2016, 17(5-6):414-25.
Qi et al., "Sodium 4-Phenylbutyrate Protects against Cerebral Ischemic Injury," Mol Pharmacol., 2004, 66:899-908.
Reagan-Shaw et al., "Dose translation from animal to human studies revisited," FASEB J., 2007, 22:659-661.
Reijn et al., "CSF neurofilament protein analysis in the differential diagnosis of ALS." Journal of Neurology, Apr. 1, 2009, 256(4):615.
Reisberg et al., "Memantine in Moderate-to-Severe Alzheimer's Disease," N Engl J Med., 2003, 348:1333-41.
Ricobaraza et al., "Phenylbutyrate ameliorates cognitive deficit and reduces tau pathology in an Alzheimer's disease mouse model," Neuropsychopharmacology, Jun. 2009, 34(7):1721-32.
Rodrigues et al., "Tauroursodeoxycholic acid prevents Bax-induced membrane perturbation and cytochrome C release in isolated mitochondria," Biochemistry, Mar. 18, 2003, 42(10):3070-80.
Rodrigues et al., "The therapeutic effects of ursodeoxycholic acid as an anti-apoptotic agent," Expert Opinion on Investigational Drugs, Jul. 1, 2001, 10(7):1243-53.
Rodrigues et al., "Amyloid $\beta$-Peptide Disrupts Mitochondrial Membrane Lipid and Protein Structure: Protective Role of Tauroursodeoxycholate," Biochem Biophys Res Comm., 2001, 281:468-474.
Rosen et al., "A frequent Ala 4 to Val mutation in exon 1 of the superoxide dismutase-1 gene: decreased enzyme activity is associated with a rapidly progressive familial ALS," Human Molecular Genetics, 1994, 3:981-7.
Rosen et al., "Mutations in Cu/Zn superoxide dismutase gene are associated with familial amyotrophic lateral sclerosis," Nature, Mar. 1993, 362(6415):59-62.
Rothstein, "Current hypotheses for the underlying biology of amyotrophic lateral sclerosis," Annals of Neurology, Jan. 2009, 65(S1):S3-9.

(56) References Cited

OTHER PUBLICATIONS

Roy and Kolattukudy, "Monocyte chemotactic protein-induced protein (MCPIP) promotes inflammatory angiogenesis via sequential induction of oxidative stress, endoplasmic reticulum stress and autophagy," Cellular Signalling, 2012, 24:2123-2131.
Roy et al., "Sodium phenylbutyrate controls neuroinflammatory and antioxidant activities and protects dopaminergic neurons in mouse models of Parkinson's disease," PloS one, Jun. 18, 2012, 7(6):e38113, 18 pages.
Rubio-Perez and Morillas-Ruiz, "A Review: Inflammatory Process in Alzheimer's Disease, Role of Cytokines," Scientific World J., 2012, 15 pages.
Rutkove, "Clinical measures of disease progression in amyotrophic lateral sclerosis," Neurotherapeutics, Apr. 1, 2015, 12(2):384-93.
Ryu et al., "Sodium phenylbutyrate prolongs survival and regulates expression of anti-apoptotic genes in transgenic amyotrophic lateral sclerosis mice," Journal of Neurochemistry, Jun. 2005, 93(5):1087-98.
Schnabel, "Neuroscience: standard model. Nature News," Aug. 6, 2008, 454(7205):682-5.
Senopsys, "So You Want to Be in Films?," Taste Masking Blog, Feb. 4, 2019, 11 pages.
Sharma et al., "Bile acid toxicity structure-activity relationships: Correlations between cell viability and liophilicity in a panel of new and known bile acids using an oesophageal cell line (HET-1A)," Bioorganic & Medicinal Chemistry, Sep. 2010, 18(18): 6886-6895.
Shaw et al., "Hyperphosphorylated neurofilament NF-H is a serum biomarker of axonal injury," Biochemical and Biophysical Research Communications, Nov. 4, 2005, 336(4):1268-77.
Shefner, "Strength testing in motor neuron diseases," Neurotherapeutics, Jan. 2017, 14(1):154-60.
Shepheard et al., "Urinary p75ECD: A prognostic, disease progression, and pharmacodynamic biomarker in ALS," Neurology, Mar. 21, 2017, 88(12):1137-43.
Simon et al., "Quantifying disease progression in amyotrophic lateral sclerosis," Annals of Neurology, Nov. 2014, 76(5):643-57.
Smith et al., "The Role of Mitochondria in Amyotrophic Lateral Sclerosis," Neuroscience Letters, Sep. 25, 2019, 710:58 pages.
Spuch et al., "New Insights in the Amyloid-Beta Interaction with Mitochondria," J Aging Res., 2012, 9 pages.
Steele and Glazier, "Is donepezil effective for treating Alzheimer's disease," CA Family Physician, Apr. 1999, 45:917-919.
Suaud et al., "4-Phenylbutyrate stimulates Hsp70 expression through the Elp2 component of elongator and STAT-3 in cystic fibrosis epithelial cells," Journal of Biological Chemistry, Dec. 30, 2011, 286(52):45083-92.
Suaud et al., "ERp29 regulates ΔF508 and wild-type cystic fibrosis transmembrane conductance regulator (CFTR) trafficking to the plasma membrane in cystic fibrosis (CF) and non-CF epithelial cells," Journal of Biological Chemistry, Jun. 17, 2011, 286(24):21239-53.
Suh and Checler, "Amyloid Precursor Protein, Presenilins, and α-Synuclein: Molecular Pathogenesis and Pharmacological Applications in Alzheimer's Disease," Pharmacol Rev., 2002, 54:469-525.
Sung and Waxman, "Combination of Cytotoxic-Differentiation Therapy with 5-Fluorouracil and Phenylbutyrate in Patients with Advanced Colorectal Cancer," Anticancer Res., 2007, 27:995-1002.
Sung JJ et al.: "Tauroursodeoxycholic acid (TUDCA), a bile acid, inhibits GSNO-induced apoptosis by modulating reactive oxygen species (ROS) production in motor neuronal cells expressing mutant Cu/Zn superoxide dismutase (SOD1)", Theme 4 In vitro Experimental Models, Jul. 10, 2009, 6:sup1, P81, pp. 109-110.
Szweda et al., "Aging, lipofuscin formation, and free radical-mediated inhibition of cellular proteolytic systems," Ageing Res Rev., 2003, 2:383-405.
Tallarida et al., "Quantitative methods for assessing drug synergism," Genes & Cancer, Nov. 2011, 2(11):1003-8.
Taub, K: "TUDCA: Tauroursodeoxycholic Acid", Stanford.edu, Nov. 14, 2004, 3 pages.

Taylor et al., "Decoding ALS: from genes to mechanism," Nature, Nov. 2016, 539(7628):197-206.
Taylor et al., "Pooled Resource Open-Access ALS Clinical Trials Consortium. Predicting disease progression in amyotrophic lateral sclerosis," Annals of Clinical and Translational Neurology, Nov. 3, 2016, 3(11):866-75.
Therrien et al., "ALS: recent developments from genetics studies," Current Neurology and Neuroscience Reports, Jun. 1, 2016, 16(6):59, 12 pages.
Thouvenot et al., "Serum neurofilament light chain at time of diagnosis is an independent prognostic factor of survival in amyotrophic lateral sclerosis," European Journal of Neurology, Feb. 2020, 27(2):251-7.
Traxinger et al., "Prognosis and epidemiology of amyotrophic lateral sclerosis: analysis of a clinic population, 1997-2011," Neurology: Clinical Practice, Aug. 1, 2013, 3(4):313-20.
Traynor et al., "Functional outcome measures as clinical trial endpoints in ALS," Neurology, Nov. 2004, 63(10):1933-5.
Tuppo et al., "Free radical oxidative damage and Alzheimer's disease," JAOA, 2001, 101(12):S11-S15.
Turner et al., "Biomarkers in amyotrophic lateral sclerosis. The Lancet Neurology," Jan. 1, 2009, 8(1):94-109.
Turner et al., "Mechanisms, models and biomarkers in amyotrophic lateral sclerosis," Amyotrophic Lateral Sclerosis and Frontotemporal Degeneration, May 1, 2013, 14(sup1):19-32, 25 pages.
Turner et al., "The diagnostic pathway and prognosis in bulbar-onset amyotrophic lateral sclerosis," Journal of the Neurological Sciences, Jul. 15, 2010, 294(1-2):81-5.
Uppala et al., "Chemical chaperone, TUDCA unlike PBA, mitigates protein aggregation efficiently and resists ER and non-ER stress induced HepG2 cell death," Scientific Reports, Jun. 19, 2017, 7(1):1-3.
Vajda et al., "Genetic testing in ALS: a survey of current practices," Neurology, Mar. 7, 2017, 88(10):991-9.
Van Den Berg et al., "Revised Airlie House consensus guidelines for design and implementation of ALS clinical trials," Neurology, Apr. 2, 2019, 92(14):e1610-23.
Van Eijk et al., "Comparing methods to combine functional loss and mortality in clinical trials for amyotrophic lateral sclerosis," Clinical Epidemiology, Mar. 19, 2018, 10:333.
Van Es et al., "Amyotrophic lateral sclerosis," The Lancet, Nov. 4, 2017, 390(10107):2084-98.
Vrotsos et al., "MCP-1 involvement in glial differentiation of neuroprogenitor cells through APP signaling," Brain Res Bulletin, 2009, 79:97-103.
Walling, "Amyotrophic lateral sclerosis: Lou Gehrig's disease," American Family Physician, Mar. 15, 1999, 59(6), 11 pages.
Watson et al., "Solution Structure of Methionine-Oxidized Amyloid β-Peptide (1-40). Does Oxidation Affect Conformational Switching?" Biochem., 1998, 37:12700-12706.
Weiss et al., "A randomized trial of mexiletine in ALS: safety and effects on muscle cramps and progression," Neurology, Apr. 19, 2016, 86(16):1474-81.
Weydt et al., "Neurofilament levels as biomarkers in asymptomatic and symptomatic familial amyotrophic lateral sclerosis," Annals of Neurology, Jan. 2016, 79(1):152-8.
Whittemore et al., "A detailed analysis of hydrogen D6 peroxide-induced cell death in primary neuronal culture," Neuroscience, Aug. 1995, 67 (4): 921-32.
Wiley et al., "Phenylbutyric acid reduces amyloid plaques and rescues cognitive behavior in AD transgenic mice," Aging Cell, Jun. 2011, 10(3):418-28.
Wiley et al., "Phenylbutyric Acid Rescues Endoplasmic Reticulum Stress-Induced Suppression of APP Proteolysis and Prevents Apoptosis in Neuronal Cells," PLoS One, Feb. 2010, 5(2):e9135, 17 pages.
Wilke et al., "Correlations between serum and CSF pNfH levels in ALS, FTD and controls: a comparison of three analytical approaches," Clinical Chemistry and Laboratory Medicine (CCLM), Sep. 25, 2019, 57(10):1556-64.
Xu et al., "Neurofilaments as biomarkers for amyotrophic lateral sclerosis: a systematic review and meta-analysis," PloS one, Oct. 12, 2016, 11(10):e0164625.

(56) References Cited

OTHER PUBLICATIONS

Younce and Kolattukudy, "MCP-1 Induced Protein Promotes Adipogenesis via Oxidative Stress, Endoplasmic Reticulum Stress and Autophagy," Cell Physiol Biochem., 2012, 30:307-320.

Zhai et al., "Free radical-operated proteotoxic stress in macrophages primed with lipopolysaccharide," Free Radical Biol Med., 2012, 53:172-181.

Zhang et al., "Cytochrome P450 reaction-phenotyping: an industrial perspective," Expert Opinion on Drug Metabolism & Toxicology, Oct. 1, 2007, 3(5):667-87.

Zhang et al., "Selective, potent blockade of the IRE 1 and ATF 6 pathways by 4-phenylbutyric acid analogues," British Journal of Pharmacology, Oct. 2013, 170(4):822-34.

Zhou et al., "Enzymatic activities of CYP3A4 allelic variants on quinine 3-hydroxylation in vitro," Frontiers in Pharmacology, May 31, 2019, 10:591, 14 pages.

Zhou et al., "Phenylbutyrate up-regulates the DJ-1 protein and protects neurons in cell culture and in animal models of Parkinson disease," Journal of Biological Chemistry, Apr. 29, 2011, 286(17):14941-51.

Zürcher et al., "Increased in vivo glial activation in patients with amyotrophic lateral sclerosis: assessed with [11C]-PBR28," NeuroImage: Clinical, Jan. 1, 2015, 7:409-14.

accessdata.fda, "RELYVRIO (sodium phenylbutyrate and taurursodiol), for oral suspension, Highlights of Prescribing Information," Sep. 2022, retrieved Jun. 7, 2023 from URL <https://www.accessdata.fda.gov/drugsatfda_docs/label/2022/216660s0001bledt.pdf>, 10 pages.

clinicaltrials.gov, ID NCT03127514, "AMX0035 in Patients With Amyotrophic Lateral Sclerosis (ALS) (CENTAUR)," updated Apr. 20, 2017, retrieved May 31, 2023 from URL <https://www.clinicaltrials.gov/ct2/history/NCT03127514?V_1=View#StudyPageTop>, 7 pages.

clinicaltrials.gov, ID NCT03127514, "AMX0035 in Patients With Amyotrophic Lateral Sclerosis (ALS) (CENTAUR)," updated Apr. 25, 2017, retrieved May 31, 2023 from URL <https://www.clinicaltrials.gov/ct2/history/NCT03127514?V_2=View#StudyPageTop>, 7 pages.

clinicaltrials.gov, ID NCT03127514, "AMX0035 in Patients With Amyotrophic Lateral Sclerosis (ALS) (CENTAUR)," updated Aug. 14, 2017, retrieved May 31, 2023 from URL <https://www.clinicaltrials.gov/ct2/history/NCT03127514?V_10=View#StudyPageTop>, 7 pages.

clinicaltrials.gov, ID NCT03127514, "AMX0035 in Patients With Amyotrophic Lateral Sclerosis (ALS) (CENTAUR)," updated Aug. 3, 2017, retrieved May 31, 2023 from URL <https://www.clinicaltrials.gov/ct2/history/NCT03127514?V_9=View#StudyPageTop>, 7 pages.

clinicaltrials.gov, ID NCT03127514, "AMX0035 in Patients With Amyotrophic Lateral Sclerosis (ALS) (CENTAUR)," updated Aug. 30, 2017, retrieved May 31, 2023 from URL <https://www.clinicaltrials.gov/ct2/history/NCT03127514?V_11=View#StudyPageTop>, 7 pages.

clinicaltrials.gov, ID NCT03127514, "AMX0035 in Patients With Amyotrophic Lateral Sclerosis (ALS) (CENTAUR)," updated Dec. 14, 2017, retrieved May 31, 2023 from URL <https://www.clinicaltrials.gov/ct2/history/NCT03127514?V_26=View#StudyPageTop>, 8 pages.

clinicaltrials.gov, ID NCT03127514, "AMX0035 in Patients With Amyotrophic Lateral Sclerosis (ALS) (CENTAUR)," updated Dec. 20, 2017, retrieved May 31, 2023 from URL <https://www.clinicaltrials.gov/ct2/history/NCT03127514?V_27=View#StudyPageTop>, 8 pages.

clinicaltrials.gov, ID NCT03127514, "AMX0035 in Patients With Amyotrophic Lateral Sclerosis (ALS) (CENTAUR)," updated Dec. 21, 2017, retrieved May 31, 2023 from URL <https://www.clinicaltrials.gov/ct2/history/NCT03127514?V_28=View#StudyPageTop>, 8 pages.

clinicaltrials.gov, ID NCT03127514, "AMX0035 in Patients With Amyotrophic Lateral Sclerosis (ALS) (CENTAUR)," updated Dec. 27, 2017, retrieved May 31, 2023 from URL <https://www.clinicaltrials.gov/ct2/history/NCT03127514?V_29=View#StudyPageTop>, 8 pages.

clinicaltrials.gov, ID NCT03127514, "AMX0035 in Patients With Amyotrophic Lateral Sclerosis (ALS) (CENTAUR)," updated Dec. 4, 2017, retrieved May 31, 2023 from URL <https://www.clinicaltrials.gov/ct2/history/NCT03127514?V_24=View#StudyPageTop>, 8 pages.

clinicaltrials.gov, ID NCT03127514, "AMX0035 in Patients With Amyotrophic Lateral Sclerosis (ALS) (CENTAUR)," updated Dec. 6, 2017, retrieved May 31, 2023 from URL <https://www.clinicaltrials.gov/ct2/history/NCT03127514?V_25=View#StudyPageTop>, 8 pages.

clinicaltrials.gov, ID NCT03127514, "AMX0035 in Patients With Amyotrophic Lateral Sclerosis (ALS) (CENTAUR)," updated Feb. 11, 2019, retrieved May 31, 2023 from URL <https://www.clinicaltrials.gov/ct2/history/NCT03127514?V_36=View#StudyPageTop>, 8 pages.

clinicaltrials.gov, ID NCT03127514, "AMX0035 in Patients With Amyotrophic Lateral Sclerosis (ALS) (CENTAUR)," updated Jan. 29, 2018, retrieved May 31, 2023 from URL <https://www.clinicaltrials.gov/ct2/history/NCT03127514?V_31=View#StudyPageTop>, 8 pages.

clinicaltrials.gov, ID NCT03127514, "AMX0035 in Patients With Amyotrophic Lateral Sclerosis (ALS) (CENTAUR)," updated Jan. 3, 2018, retrieved May 31, 2023 from URL <https://www.clinicaltrials.gov/ct2/history/NCT03127514?V_30=View#StudyPageTop>, 8 pages.

clinicaltrials.gov, ID NCT03127514, "AMX0035 in Patients With Amyotrophic Lateral Sclerosis (ALS) (CENTAUR)," updated Jul. 7, 2017, retrieved May 31, 2023 from URL <https://www.clinicaltrials.gov/ct2/history/NCT03127514?V_8=View#StudyPageTop>, 7 pages.

clinicaltrials.gov, ID NCT03127514, "AMX0035 in Patients With Amyotrophic Lateral Sclerosis (ALS) (CENTAUR)," updated Jun. 13, 2017, retrieved May 31, 2023 from URL <https://www.clinicaltrials.gov/ct2/history/NCT03127514?V_5=View#StudyPageTop>, 7 pages.

clinicaltrials.gov, ID NCT03127514, "AMX0035 in Patients With Amyotrophic Lateral Sclerosis (ALS) (CENTAUR)," updated Jun. 15, 2017, retrieved May 31, 2023 from URL <https://www.clinicaltrials.gov/ct2/history/NCT03127514?V_6=View#StudyPageTop>, 7 pages.

clinicaltrials.gov, ID NCT03127514, "AMX0035 in Patients With Amyotrophic Lateral Sclerosis (ALS) (CENTAUR)," updated Jun. 19, 2017, retrieved May 31, 2023 from URL <https://www.clinicaltrials.gov/ct2/history/NCT03127514?V_7=View#StudyPageTop>, 7 pages.

clinicaltrials.gov, ID NCT03127514, "AMX0035 in Patients With Amyotrophic Lateral Sclerosis (ALS) (CENTAUR)," updated Jun. 9, 2017, retrieved May 31, 2023 from URL <https://www.clinicaltrials.gov/ct2/history/NCT03127514?V_4=View#StudyPageTop>, 7 pages.

clinicaltrials.gov, ID NCT03127514, "AMX0035 in Patients With Amyotrophic Lateral Sclerosis (ALS) (CENTAUR)," updated Mar. 19, 2018, retrieved May 31, 2023 from URL <https://www.clinicaltrials.gov/ct2/history/NCT03127514?V_32=View#StudyPageTop>, 8 pages.

clinicaltrials.gov, ID NCT03127514, "AMX0035 in Patients With Amyotrophic Lateral Sclerosis (ALS) (CENTAUR)," updated May 21, 2018, retrieved May 31, 2023 from URL <https://www.clinicaltrials.gov/ct2/history/NCT03127514?V_33=View#StudyPageTop>, 8 pages.

clinicaltrials.gov, ID NCT03127514, "AMX0035 in Patients With Amyotrophic Lateral Sclerosis (ALS) (CENTAUR)," updated May 24, 2017, retrieved May 31, 2023 from URL <https://www.clinicaltrials.gov/ct2/history/NCT03127514?V_3=View#StudyPageTop>, 7 pages.

clinicaltrials.gov, ID NCT03127514, "AMX0035 in Patients With Amyotrophic Lateral Sclerosis (ALS) (CENTAUR)," updated May 28, 2020, retrieved May 31, 2023 from URL <https://www.clinicaltrials.gov/ct2/history/NCT03127514?V_40=View#StudyPageTop>, 7 pages.

clinicaltrials.gov, ID NCT03127514, "AMX0035 in Patients With Amyotrophic Lateral Sclerosis (ALS) (CENTAUR)," updated Nov. 13, 2017, retrieved May 31, 2023 from URL <https://www.clinicaltrials.gov/ct2/history/NCT03127514?V_21=View#StudyPageTop>, 8 pages.

clinicaltrials.gov, ID NCT03127514, "AMX0035 in Patients With Amyotrophic Lateral Sclerosis (ALS) (CENTAUR)," updated Nov. 16, 2017, retrieved May 31, 2023 from URL <https://www.clinicaltrials.gov/ct2/history/NCT03127514?V_22=View#StudyPageTop>, 8 pages.

clinicaltrials.gov, ID NCT03127514, "AMX0035 in Patients With Amyotrophic Lateral Sclerosis (ALS) (CENTAUR)," updated Nov. 19, 2018, retrieved May 31, 2023 from URL <https://www.clinicaltrials.gov/ct2/history/NCT03127514?V_35=View#StudyPageTop>, 8 pages.

clinicaltrials.gov, ID NCT03127514, "AMX0035 in Patients With Amyotrophic Lateral Sclerosis (ALS) (CENTAUR)," updated Nov. 27, 2017, retrieved May 31, 2023 from URL <https://www.clinicaltrials.gov/ct2/history/NCT03127514?V_23=View#StudyPageTop>, 8 pages.

clinicaltrials.gov, ID NCT03127514, "AMX0035 in Patients With Amyotrophic Lateral Sclerosis (ALS) (CENTAUR)," updated Nov. 6, 2017, retrieved May 31, 2023 from URL <https://www.clinicaltrials.gov/ct2/history/NCT03127514?V_19=View#StudyPageTop>, 7 pages.

clinicaltrials.gov, ID NCT03127514, "AMX0035 in Patients With Amyotrophic Lateral Sclerosis (ALS) (CENTAUR)," updated Nov.

(56) References Cited

OTHER PUBLICATIONS 9, 2017, retrieved May 31, 2023 from URL <https://www.clinicaltrials.gov/ct2/history/NCT03127514?V_20=View#StudyPageTop>, 8 pages.
clinicaltrials.gov, ID NCT03127514, "AMX0035 in Patients With Amyotrophic Lateral Sclerosis (ALS) (CENTAUR)," updated Oct. 16, 2017, retrieved May 31, 2023 from URL <https://www.clinicaltrials.gov/ct2/history/NCT03127514?V_15=View#StudyPageTop>, 7 pages.
clinicaltrials.gov, ID NCT03127514, "AMX0035 in Patients With Amyotrophic Lateral Sclerosis (ALS) (CENTAUR)," updated Oct. 19, 2017, retrieved May 31, 2023 from URL <https://www.clinicaltrials.gov/ct2/history/NCT03127514?V_16=View#StudyPageTop>, 7 pages.
clinicaltrials.gov, ID NCT03127514, "AMX0035 in Patients With Amyotrophic Lateral Sclerosis (ALS) (CENTAUR)," updated Oct. 20, 2017, retrieved May 31, 2023 from URL <https://www.clinicaltrials.gov/ct2/history/NCT03127514?V_17=View#StudyPageTop>, 7 pages.
clinicaltrials.gov, ID NCT03127514, "AMX0035 in Patients With Amyotrophic Lateral Sclerosis (ALS) (CENTAUR)," updated Oct. 25, 2017, retrieved May 31, 2023 from URL <https://www.clinicaltrials.gov/ct2/history/NCT03127514?V_18=View#StudyPageTop>, 8 pages.
clinicaltrials.gov, ID NCT03127514, "AMX0035 in Patients With Amyotrophic Lateral Sclerosis (ALS) (CENTAUR)," updated Oct. 6, 2017, retrieved May 31, 2023 from URL <https://www.clinicaltrials.gov/ct2/history/NCT03127514?V_14=View#StudyPageTop>, 7 pages.
clinicaltrials.gov, ID NCT03127514, "AMX0035 in Patients With Amyotrophic Lateral Sclerosis (ALS) (CENTAUR)," updated Oct. 8, 2019, retrieved May 31, 2023 from URL <https://www.clinicaltrials.gov/ct2/history/NCT03127514?V_39=View#StudyPageTop>, 7 pages.
clinicaltrials.gov, ID NCT03127514, "AMX0035 in Patients With Amyotrophic Lateral Sclerosis (ALS) (CENTAUR)," updated Sep. 19, 2018, retrieved May 31, 2023 from URL <https://www.clinicaltrials.gov/ct2/history/NCT03127514?V_34=View#StudyPageTop>, 8 pages.
clinicaltrials.gov, ID NCT03127514, "AMX0035 in Patients With Amyotrophic Lateral Sclerosis (ALS) (CENTAUR)," updated Sep. 19, 2019, retrieved May 31, 2023 from URL <https://www.clinicaltrials.gov/ct2/history/NCT03127514?V_38=View#StudyPageTop>, 7 pages.
clinicaltrials.gov, ID NCT03127514, "AMX0035 in Patients With Amyotrophic Lateral Sclerosis (ALS) (CENTAUR)," updated Sep. 21, 2017, retrieved May 31, 2023 from URL <https://www.clinicaltrials.gov/ct2/history/NCT03127514?V_7=View#StudyPageTop>, 8 pages.
clinicaltrials.gov, ID NCT03127514, "AMX0035 in Patients With Amyotrophic Lateral Sclerosis (ALS) (CENTAUR)," updated Sep. 7, 2017, retrieved May 31, 2023 from URL <https://www.clinicaltrials.gov/ct2/history/NCT03127514?V_12=View#StudyPageTop>, 8 pages.
KR Office Action in Korean Appln. No. 10-2022-7037260, dated Apr. 5, 2023, 13 pages (with English translation).
US Department of Health and Human Services, Center for Drug Evaluation and Research, "Guidance for Industry: Food-Effect Bioavailability and Fed Bioequivalence Studies," Dec. 2002, retrieved May 12, 2023 from URL <https://pink.pharmaintelligence.informa.com/-/media/pmbi-old-site/supporting-documents/the-pink-sheet/75/49/bioavailfoodguidance.pdf>, 12 pages.
Amylyx Pharmaceuticals Inc., "Evaluation of the Safety, Tolerability, Efficacy and Activity of AMX0035, a Fixed Combination of Phenylbutyrate (PB) and Tauroursodeoxycholic Acid (TUDCA), for Treatment of Amyotrophic Lateral Sclerosis (ALS)," Journal of Neurology, Neurosurgery & Psychiatry, Nov. 18, 2016, 204 pages.
Bregigeon et al., "Impact of tenofovir dose adjustment on both estimated glomerular filtration rate and tenofovir trough concentration," Antiviral Therapy, Feb. 2017, 22:529, 5 pages.
Dhapola et al., "Recent advances in molecular pathways and therapeutic implications targeting neuroinflammation for Alzheimer's disease," Inflammopharmacology, Dec. 2021, 1:1, 13 pages.
Iłżecka et al., "Serum bilirubin concentration in patients with amyotrophic lateral sclerosis," Clinical Neurology and Neurosurgery, Sep. 1, 2003, 105(4):237-40.
Kirkinezos et al., "An ALS mouse model with a permeable blood-brain barrier benefits from systemic cyclosporine A treatment," Journal of Neurochemistry, Feb. 2004, 88(4):821-6.
Nodera et al., "Frequent hepatic steatosis in amyotrophic lateral sclerosis: Implication for systemic involvement," Neurology and Clinical Neuroscience, Mar. 2015, 3(2):58-62.
PCT International Search Report and Written Opinion in International Appln. No. PCT/US2023/021830, dated Jul. 25, 2023, 13 pages.
PCT International Search Report and Written Opinion in International Appln. No. PCT/US2023/022383, dated Aug. 10, 2023, 13 pages.
PCT International Search Report and Written Opinion in International Appln. No. PCT/US2023/063495, dated Jun. 22, 2023, 14 pages.
Yamazaki et al., "Pharmacokinetic interactions between isavuconazole and the drug transporter substrates atorvastatin, digoxin, metformin, and methotrexate in healthy subjects," Clinical Pharmacology in Drug Development, Jan. 2017, 6(1):66-75.
Zhang et al., "Inhibition of bile salt transport by drugs associated with liver injury in primary hepatocytes from human, monkey, dog, rat, and mouse," Chemico-Biological Interactions, Aug. 5, 2016, 255:45, 25 pages.
amylyx.com, Amylyx Pharmaceuticals Announces Topline Results From Global Phase 3 Phoenix Trial of AMX0035 in ALS, Mar. 8, 2024, retrieved Mar. 21, 2024 from URL <https://www.amylyx.com/news/amylyx-pharmaceuticals-announces-topline-results-from-global-phase-3-phoenix-trial-ofamx0035-in-als>, 6 pages.
Arru et al., "HER V-K modulates the immune response in ALS patients," Microogranisms, Aug. 2021, 9(8):1784, 15 pages.
JP Office Action in Japanese Appln. No. 2023-035423, mailed on Apr. 2, 2024, 11 pages (with English translation).
KR Office Action in Korean Appln. No. 10-2023-7040555, mailed on Jun. 3, 2024, 15 pages (with English translation).
Li et al., "Human endogenous retrovirus-K contributes to motor neuron disease," Science Translational Medicine, Sep. 2015, 7(307):307ra153, 13 pages.
Oveson et al., "Constituents of bile bilirubin and TUDCA, protect against oxidative stress-induced retinal degeneration," Journal of Neurochemistry, Jan. 2011, 116(1):144, 19 pages.
Phan et al., "Pathological manifestation of human endogenous retrovirus K in frontotemporal dementia," Communications Medicine, Dec. 2021, 1(1):60, 11 pages.
Van den Berg et al., "Results From the Global Phase 3 Trial Evaluating Sodium Phenylbutyrate and Ursodoxicoltaurine in ALS," ENCALS (European Network to Cure ALS), Stockholm, Sweden, Jun. 18, 2024, 30 pages.

\* cited by examiner

METHODS AND COMPOSITIONS FOR TREATING AMYOTROPHIC LATERAL SCLEROSIS

TECHNICAL FIELD

The present disclosure generally relates to compositions and methods for treating Amyotrophic lateral sclerosis.

BACKGROUND

Amyotrophic lateral sclerosis (ALS) is the most prevalent progressive motor neuron disease. ALS causes the progressive degeneration of motor neurons, resulting in rapidly progressing muscle weakness and atrophy that eventually leads to partial or total paralysis. Median survival from symptom onset is 2 to 3 years, with respiratory failure being the predominant cause of death. ALS treatment currently centers on symptom management. Only two FDA-approved medications for ALS, riluzole and edaravone, are presently available. Accordingly, there is a need for improved therapies for treating ALS.

Concomitant administration of different drugs may lead to adverse effects since the metabolism and/or excretion of each drug may reduce or interfere with the metabolism and/or excretion of the other drug(s), thus increasing the effective concentrations of those drugs as compared to the effective concentrations of those drugs when administered alone. However, patients with neurodegenerative disease, such as ALS patients, often require treatment with multiple drugs, so that the potential toxicity of drug-drug interactions present disadvantages that can have deleterious consequences for these patients. Accordingly, improved methods of treatment allowing the administration of multiple drugs are desired.

SUMMARY

Provided herein are methods of treating at least one symptom of Amyotrophic Lateral Sclerosis (ALS) in a subject, the method comprising: (a) administering to a subject who has received a first dosage of an inhibitor of bile salt efflux pump (BSEP) a composition comprising about 1 gram of Taurursodiol (TURSO) and about 3 grams of sodium phenylbutyrate, (b) determining or having determined a first level of serum transaminases and/or bilirubin in a first biological sample from the subject, and (c) administering to the subject a second dosage of the inhibitor of BSEP, wherein the second dosage is lower than the first dosage.

In some embodiments, the inhibitor of BSEP is cyclosporine. In some embodiments, the first dosage of cyclosporine is about 0.5 to about 15 mg/kg/day.

In some embodiments, the methods further comprise step (d), determining or having determined a second level of serum transaminases and/or bilirubin a second biological sample from the subject.

In some embodiments, the second level of the serum transaminases and/or bilirubin is lower than the first level. In some embodiments, the biological sample is a plasma or serum sample.

In some embodiments, the TURSO is administered at an amount of about 1 to about 2 grams per day, inclusive. In some embodiments, the sodium phenylbutyrate is administered at an amount of about 3 to about 6 grams per day, inclusive. In some embodiments, the TURSO is administered at an amount of about 1 gram once a day. In some embodiments, the TURSO is administered at an amount of about 1 gram twice a day. In some embodiments, the sodium phenylbutyrate is administered at an amount of about 3 grams once a day. In some embodiments, the sodium phenylbutyrate is administered at an amount of about 3 grams twice a day.

In some embodiments, the composition is administered to the subject orally or through a feeding tube. In some embodiments, the subject is diagnosed with ALS. In some embodiments, the subject is suspected as having ALS. In some embodiments, the subject is human.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

All publications, patent applications, patents, and other references mentioned herein are incorporated by reference in their entirety. In case of conflict, the present specification, including definitions, will control. In addition, the materials, methods, and examples are illustrative only and not intended to be limiting. Other features and advantages of the invention will be apparent from the following detailed description, and from the claims.

DETAILED DESCRIPTION

Applicant has discovered that a combination of a bile acid (e.g. Taurursodiol (TURSO)) and a phenylbutyrate compound (e.g. sodium phenylbutyrate) can be used for treating one or more symptoms of ALS. Applicant has also surprisingly found that TURSO and its metabolites, ursodeoxycholic acid and glycoursodeoxycholic acid, are inhibitors of BSEP. Additionally, phenylacetic acid, a metabolite of sodium phenylbutyrate was surprisingly found to inhibit BSEP also. When inhibitors of BSEP are administered concomitantly with a composition comprising a bile acid and a phenylbutyrate compound, drug-drug interactions can result leading to an exacerbation of accumulation of conjugated bile salts in the liver, thereby leading to adverse events. Accordingly, the present disclosure provides methods of treating at least one symptom of ALS in a subject who is also receiving a BSEP inhibitor.

The present disclosure provides methods of treating at least one symptom of ALS in a subject, the methods including (a) administering to a subject who has received a first dosage of a BSEP inhibitor an effective amount of a composition comprising about 1 gram of TURSO and about 3 grams of sodium phenylbutyrate, (b) determining or having determined a first level of serum transaminases and/or bilirubin in a first biological sample from the subject, and (c) administering to the subject a second dosage of the BSEP inhibitor, wherein the second dosage is lower than the first dosage.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art.

I. Amyotrophic Lateral Sclerosis (ALS)

The terms "amyotrophic lateral sclerosis" and "ALS" are used interchangeably herein, and include all of the classifications of ALS known in the art, including, but not limited to classical ALS (e.g., ALS that affects both lower and upper motor neurons), Primary Lateral Sclerosis (PLS, e.g., those that affect only the upper motor neurons), Progressive Bulbar Palsy (PBP or Bulbar Onset, a version of ALS that typically begins with difficulties swallowing, chewing and speaking) and Progressive Muscular Atrophy (PMA, typically affecting only the lower motor neurons). The terms include sporadic and familial (hereditary) ALS, ALS at any rate of progression (e.g., rapid, non-slow or slow progression) and ALS at any stage (e.g., prior to onset, at onset and late stages of ALS).

The subjects in the methods described herein may exhibit one or more symptoms associated with ALS, or have been diagnosed with ALS. In some embodiments, the subjects may be suspected as having ALS, and/or at risk for developing ALS.

The subjects in the methods described herein may exhibit one or more symptoms associated with benign fasciculation syndrome (BFS) or cramp-fasciculation syndrome (CFS).

Some embodiments of any of the methods described herein can further include determining that a subject has or is at risk for developing ALS, diagnosing a subject as having or at risk for developing ALS, or selecting a subject having or at risk for developing ALS. Likewise, some embodiments of any of the methods described herein can further include determining that a subject has or is at risk for developing benign fasciculation syndrome or cramp fasciculation syndrome, diagnosing a subject as having or at risk for developing BFS or CFS, or selecting a subject having or at risk for developing BFS or CFS.

In some embodiments of any of the methods described herein, the subject has shown one or more symptoms of ALS for about 24 months or less (e.g., about 23, 22, 21, 20, 19, 18, 17, 16, 15, 14, 13, 12, 11, 10, 9, 8, 7, 6, 5, 4, 3, 2, 1 month, or 1 week or less). In some embodiments, the subject has shown one or more symptoms of ALS for about 36 months or less (e.g., about 35, 34, 33, 32, 31, 30, 29, 28, 27, 26, or 25 months or less).

The order and type of ALS symptoms displayed by a subject may depend on which motor neurons in the body are damaged first, and consequently which muscles in the body are damaged first. For example, bulbar onset, limb onset, or respiratory onset ALS may present with similar or different symptoms. In general, ALS symptoms may include muscle weakness or atrophy (e.g., affecting upper body, lower body, and/or speech), muscle fasciculation (twitching), cramping, or stiffness of affected muscles. Early symptoms of ALS may include those of the arms or legs, difficulty in speaking clearly or swallowing (e.g., in bulbar onset ALS). Other symptoms include loss of tongue mobility, respiratory difficulties, difficulty breathing or abnormal pulmonary function, difficulty chewing, and/or difficulty walking (e.g., resulting in stumbling). Subjects may have respiratory muscle weakness as the initial manifestation of ALS symptoms. Such subjects may have very poor prognosis and in some instances have a median survival time of about two months from diagnosis. In some subjects, the time of onset of respiratory muscle weakness can be used as a prognostic factor.

ALS symptoms can also be classified by the part of the neuronal system that is degenerated, namely, upper motor neurons or lower motor neurons. Lower motor neuron degeneration manifests, for instance, as weakness or wasting in one or more of the bulbar, cervical, thoracic, and/or lumbosacral regions. Upper motor neuron degeneration can include increased tendon reflexes, spasticity, pseudo bulbar features, Hoffmann reflex, extensor plantar response, and exaggerated reflexes (hyperreflexia) including an overactive gag reflex. Progression of neuronal degeneration or muscle weakness is a hallmark of the disease. Accordingly, some embodiments of the present disclosure provide a method of ameliorating at least one symptom of lower motor neuron degeneration, at least one symptom of upper motor neuron degeneration, or at least one symptom from each of lower motor neuron degeneration and upper motor neuron degeneration. In some embodiments of any of the methods described herein, symptom onset can be determined based on information from subject and/or subject's family members. In some embodiments, the median time from symptom onset to diagnosis is about 12 months.

In some instances, the subject has been diagnosed with ALS. For example, the subject may have been diagnosed with ALS for about 24 months or less (e.g., about 23, 22, 21, 20, 19, 18, 17, 16, 15, 14, 13, 12, 11, 10, 9, 8, 7, 6, 5, 4, 3, 2, or 1 month or less). For example, the subject may have been diagnosed with ALS for 1 week or less, or on the same day that the presently disclosed treatments are administered. The subject may have been diagnosed with ALS for more than about 24 months (e.g., more than about 28, 32, 36, 40, 44, 48, 52, 56, 60, 64, 68, 72, 76, or 80 months). Methods of diagnosing ALS are known in the art. For example, the subject can be diagnosed based on clinical history, family history, physical or neurological examinations (e.g., signs of lower motor neuron or upper motor neuron degeneration).

The subject can be confirmed or identified, e.g. by a healthcare professional, as having ALS. Multiple parties may be included in the process of diagnosis. For example, where samples are obtained from a subject as part of a diagnosis, a first party can obtain a sample from a subject and a second party can test the sample. In some embodiments of any of the human subjects described herein, the subject is diagnosed, selected, or referred by a medical practitioner (e.g., a general practitioner).

In some embodiments, the subject fulfills the El Escorial criteria for probable or definite ALS, i.e. the subject presents:
1. Signs of lower motor neuron (LMN) degeneration by clinical, electrophysiological or neuropathologic examination;
2. Signs of upper motor neuron (UMN) degeneration by clinical examination; and
3. Progressive spread of signs within a region or to other regions, together with the absence of:
Electrophysiological evidence of other disease processes that might explain the signs of LMN and/or UMN degenerations; and
Neuroimaging evidence of other disease processes that might explain the observed clinical and electrophysiological signs.
Under the El Escorial criteria, signs of LMN and UMN degeneration in four regions are evaluated, including brainstem, cervical, thoracic, and lumbrasacral spinal cord of the central nervous system. The subject may be determined to be one of the following categories:
A. Clinically Definite ALS, defined on clinical evidence alone by the presence of UMN, as well as LMN signs, in three regions.
B. Clinically Probable ALS, defined on clinical evidence alone by UMN and LMN signs in at least two regions with some UMN signs necessarily rostral to (above) the LMN signs.
C. Clinically Probable ALS—Laboratory-supported, defined when clinical signs of UMN and LMN dysfunction are in only one region, or when UMN signs alone are present in one region, and LMN signs defined by EMG criteria are present in at least two limbs, with proper application of neuroimaging and clinical laboratory protocols to exclude other causes.
D. Clinically Possible ALS, defined when clinical signs of UMN and LMN dysfunction are found together in only one region or UMN signs are found alone in two or more regions; or LMN signs are found rostral to UMN signs and the diagnosis of Clinically Probable—Laboratory-supported.

In some embodiments, the subject has clinically definite ALS (e.g., based on the El Escorial criteria).

The subject can be evaluated and/or diagnosed using the Revised Amyotrophic Lateral Sclerosis Functional Rating Scale (ALSFRS-R). The ALSFRS-R is an ordinal rating scale (ratings 0-4) used to determine subjects' assessment of their capability and independence in 12 functional activities relevant in ALS. ALSFRS-R scores calculated at diagnosis can be compared to scores throughout time to determine the speed of progression. Change in ALSFRS-R scores can be correlated with change in strength over time, and can be associated with quality of life measures and predicted survival. ALSFRS-R demonstrates a linear mean slope and can be used as a prognostic indicator (See e.g., Berry et al. Amyotroph Lateral Scler Frontotemporal Degener 15:1-8, 2014; Traynor et al., Neurology 63:1933-1935, 2004; Simon et al., Ann Neurol 76:643-657, 2014; and Moore et al. Amyotroph Lateral Scler Other Motor Neuron Disord 4:42, 2003).

In the ALSFRS-R, functions mediated by cervical, trunk, lumbosacral, and respiratory muscles are each assessed by 3 items. Each item is scored from 0-4, with 4 reflecting no involvement by the disease and 0 reflecting maximal involvement. The item scores are added to give a total. Total scores reflect the impact of ALS, with the following exemplary categorization: >40 (minimal to mild); 39-30 (mild to moderate); <30 (moderate to severe); <20 (advanced disease).

For example, a subject can have an ALSFRS-R score (e.g., a baseline ALSFRS-R score) of 40 or more (e.g., at least 41, 42, 43, 44, 45, 46, 47, or 48), between 30 and 39, inclusive (e.g., 31, 32, 33, 34, 35, 36, 37, or 38), or 30 or less (e.g., 21, 22, 23, 24, 25, 26, 27, 28, or 29). In some embodiments of any of the methods described herein, the subject has an ALSFRS-R score (e.g., a baseline ALSFRS-R score) of 40 or less (e.g., 39, 38, 37, 36, 35, 34, 33, 32, 31, 30, 29, 28, 27, 26, 25, 24, 23, 22, 21, 20, 19, 18, 17, 16, 15, 14, 13, 12, 11, 10 or less). In some embodiments, the subject has an ALSFRS-R score (e.g., a baseline ALSFRS-R score) of 20 or less (e.g., 19, 18, 17, 16, 15, 14, 13, 12, 11, 10, 9, 8, 7, 6, 5 or less).

As ALS is a progressive disease, all patients generally will progress over time. However, a large degree of inter-subject variability exists in the rate of progression, as some subjects die or require respiratory support within months while others have relatively prolonged survival. The subjects described herein may have rapid progression ALS or slow progression ALS. The rate of functional decline in a subject with ALS can be measured by the change in ALSFRS-R score per month. For example, the score can decrease by about 1.02 (±2.3) points per month.

One predictor of patient progression is the patient's previous rate of disease progression ($\Delta$FS), which can be calculated as: $\Delta$FS=(48 −ALSFRS-R score at the time of evaluation)/duration from onset to time of evaluation (month). The $\Delta$FS score represents the number of ALSFRS-R points lost per month since symptom onset, and can be a significant predictor of progression and/or survival in subjects with ALS (See e.g., Labra et al. J Neurol Neurosurg Psychiatry 87:628-632, 2016 and Kimura et al. Neurology 66:265-267, 2006). The subject may have a disease progression rate ($\Delta$FS) of about 0.50 or less (e.g., about 0.45, 0.40, 0.35, 0.30, 0.25, 0.20, 0.15, or 0.10 or less); between about 0.50 and about 1.20 inclusive (e.g., about 0.55, 0.60, 0.65, 0.70, 0.75, 0.80, 0.85, 0.90, 0.95, 1.00, 1.05, 1.10, or 1.15); or about 1.20 or greater (e.g., about 1.25, 1.30, 1.35, 1.40, 1.45, 1.50, 1.55, 1.60, 1.75, 1.80, 1.85, 1.90, 1.95, or 2.00 or greater). In some embodiments of any of the methods described herein, the subject can have an ALS disease progression rate ($\Delta$FS) of about 0.50 or greater (e.g., about 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.75, 1.80, 1.85, 1.90, 1.95, or 2.00 or greater). However, it should be noted that the $\Delta$FS score is a predictor of patient progression, and may under or overestimate a patient's progression once under evaluation.

In some embodiments, since initial evaluation, the subject has lost on average about 0.8 to about 2 (e.g., about 0.9, 1.0, 1.1, 1.2, 1.3, 1.4, 1.5, 1.6, 1.7, 1.8, or 1.9) ALSFRS-R points per month over 3-12 months. In some embodiments, the subject has lost on average more than about 1.2 ALSFRS-R points per month over 3-12 months since initial evaluation. The subject may have had a decline of at least 3 points (e.g., at least 4, 6, 8, 10, 12, 14, 16, 20, 24, 28, or 32 points) in ALSFRS-R score over 3-12 months since initial evaluation. In some embodiments, the subject has lost on average about 0.8 to about 2 (e.g., about 0.9, 1.0, 1.1, 1.2, 1.3, 1.4, 1.5, 1.6, 1.7, 1.8, or 1.9) ALSFRS-R points per month over the previous 3-12 months. In some embodiments, the subject has lost on average more than about 1.2 (e.g., more than about 1.5, 1.8, 2.0, 2.5, or 3) ALSFRS-R points per month over the previous 3-12 months.

In some embodiments of any of the methods described herein, the presence or level of a marker in a sample obtained from the subject may be used for ALS diagnosis or prognosis, or to track disease activity and treatment responses. Suitable samples include, for example, cells, tissues, or body fluids (e.g. blood, urine, or cerebral spinal fluid (CSF) samples). For instance, levels of phosphorylated neurofilament heavy subunit (pNF-H) or neurofilament light chain (NfL) in the CSF and/or blood can be used as a biomarker for ALS diagnosis, prognosis, or to track disease activity or treatment outcomes. pNF-H is a main component of the neuronal cytoskeleton and is released into the CSF and the bloodstream with neuronal damage. Levels of pNF-H may correlate with the level of axonal loss and/or burden of motor neuron dysfunction (See, e.g., De Schaepdryver et al. Journal of Neurology, Neurosurgery & Psychiatry 89:367-373, 2018).

The concentration of pNF-H in the CSF and/or blood of a subject with ALS may significantly increase in the early disease stage. Higher levels of pNF-H in the plasma, serum and/or CSF may be associated with faster ALS progression (e.g., faster decline in ALSFRS-R), and/or shorter survival. pNF-H concentration in plasma may be higher in ALS subjects with bulbar onset than those with spinal onset. In some cases, an imbalance between the relative expression levels of the neurofilament heavy and light chain subunits can be used for ALS diagnosis, prognosis, or tracking disease progression.

Methods of detecting pNF-H and NfL (for example, in the cerebrospinal fluid, plasma, or serum) are known in the art and include but are not limited to, ELISA and Simoa assays (See e.g., Shaw et al. Biochemical and Biophysical Research Communications 336:1268-1277, 2005; Ganesalingam et al. Amyotroph Lateral Scler Frontotemporal Degener 14(2): 146-9, 2013; De Schaepdryver et al. Annals of Clinical and Translational Neurology 6(10): 1971-1979, 2019; Wilke et al. Clin Chem Lab Med 57(10):1556-1564, 2019; Poesen et al. Front Neurol 9:1167, 2018; Pawlitzki et al. Front. Neurol. 9:1037, 2018; Gille et al. Neuropathol Appl Neurobiol 45(3):291-304, 2019). Commercialized pNF-H detection assays can also be used, such as those developed by EnCor Biotechnology, BioVendor, and Millipore-EMD. Commercial NfL assay kits based on the Simoa technology, such as those produced by Quanterix can also be used (See, e.g., Thouvenot et al. European Journal of Neurology 27:251-257, 2020). Factors affecting pNF-H and NfL levels or their detection in serum or plasma in relation to disease course may differ from those in CSF. The levels of neurofilament (e.g. pNF-H and/or NfL) in the CSF and serum may be correlated (See, e.g., Wilke et al. Clin Chem Lab Med 57(10):1556-1564, 2019).

Subjects described herein may have a CSF or blood pNF-H level of about 300 pg/mL or higher (e.g., about 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 3000, 3200, 3500, 3800, or 4000 pg/mL or higher). In some embodiments, the serum pNF-H level can be about 70 to about 1200 pg/mL (e.g., about 70 to about 1000, about 70 to about 800, about 80 to about 600, or about 90 to about 400 pg/mL). In some embodiments, the CSF pNF-H level can be about 1000 to about 5000 pg/mL (e.g., about 1500 to about 4000, or about 2000 to about 3000 pg/mL).

The subjects may have a CSF or blood level of NfL of about 50 pg/mL or higher (e.g., about 60, 70, 80, 90, 100, 110, 120, 130, 140, 150, 160, 170, 180, 190, 200, 210, 220, 230, 240, or 250 pg/mL or higher). In some embodiments, the serum NfL level can be about 50 to about 300 pg/mL (e.g., about 50 to about 280, about 50 to about 250, about 50 to about 200, about 50 to about 150, about 50 to about 100, about 100 to about 300, about 100 to about 250, about 100 to about 200, about 100 to about 150, about 150 to about 300, about 150 to about 250, about 150 to about 200, about 200 to about 300, about 200 to about 250, or about 250 to about 300 pg/mL). In some embodiments, the CSF NfL level can be about 2000 to about 40,000 pg/mL (e.g., about 2000 to about 35,000, about 2000 to about 30,000, about 2000 to about 25,000, about 2000 to about 20,000, about 2000 to about 15,000, about 2000 to about 10,000, about 2000 to about 8000, about 2000 to about 6000, about 2000 to about 4000, about 4000 to about 40,000, about 4000 to about 35,000, about 4000 to about 30,000, about 4000 to about 25,000, about 4000 to about 20,000, about 4000 to about 15,000, about 4000 to about 10,000, about 4000 to about 8000, about 4000 to about 6000, about 6000 to about 40,000, about 6000 to about 35,000, about 6000 to about 30,000, about 6000 to about 25,000, about 6000 to about 20,000, about 6000 to about 15,000, about 6000 to about 10,000, about 6000 to about 8000, about 8000 to about 40,000, about 8000 to about 35,000, about 8000 to about 30,000, about 8000 to about 25,000, about 8000 to about 20,000, about 8000 to about 15,000, about 8000 to about 10,000, about 10,000 to about 40,000, about 10,000 to about 35,000, about 10,000 to about 30,000, about 10,000 to about 25,000, about 10,000 to about 20,000, about 10,000 to about 15,000, about 15,000 to about 40,000, about 15,000 to about 35,000, about 15,000 to about 30,000, about 15,000 to about 25,000, about 15,000 to about 20,000, about 20,000 to about 40,000, about 20,000 to about 35,000, about 20,000 to about 30,000, about 20,000 to about 25,000, about 25,000 to about 40,000, about 25,000 to about 35,000, about 25,000 to about 30,000, about 30,000 to about 40,000, about 30,000 to about 35,000, or about 35,000 to about 40,000 pg/mL).

Additional biomarkers useful for ALS diagnosis, prognosis, and disease progression monitoring are contemplated herein, including but are not limited to, CSF levels of S10013, cystatin C, and chitotriosidase (CHIT) (See e.g., Chen et al. BMC Neurol 16:173, 2016). Serum levels of uric acid can be used as a biomarker for prognosing ALS (See e.g., Atassi et al. Neurology 83(19):1719-1725, 2014). Akt phosphorylation can also be used as a biomarker for prognosing ALS (See e.g., WO2012/160563). Urine levels of p75ECD and ketones can be used as a biomarker for ALS diagnosis (See e.g., Shepheard et al. Neurology 88:1137-1143, 2017). Serum and urine levels of creatinine can also be used as a biomarker. Other useful blood, CSF, neurophysiological, and neuroradiological biomarkers for ALS are described in e.g., Turner et al. Lancet Neurol 8:94-109, 2009. Any of the markers described herein can be used for diagnosing a subject as having ALS, or determining that a subject is at risk for developing ALS.

A subject may also be identified as having ALS, or at risk for developing ALS, based on genetic analysis. Genetic variants associated with ALS are known in the art (See, e.g., Taylor et al. Nature 539:197-206, 2016; Brown and Al-Chalabi N Engl J Med 377:162-72, 2017; and http://also-d.iop.kcl.ac.uk). Subjects described herein can carry mutations in one or more genes associated with familial and/or sporadic ALS. Exemplary genes associated with ALS include but are not limited to: ANG, TARDBP, VCP, VAPB, SQSTM1, DCTN1, FUS, UNC13A, ATXN2, HNRNPA1, CHCHD10, MOBP, C12ORF2, NEK1, TUBA4A, TBK1, MATR3, PFN1, UBQLN2, TAF15, OPTN, TDP-43, and DAO. Additional description of genes associated with ALS can be found at Therrien et al. Curr Neol Neurosci Rep 16:59-71, 2016; Peters et al. J. Clin Invest 125:2548, 2015, and Pottier et al. J Neurochem, 138:Suppl 1:32-53, 2016. Genetic variants associated with ALS can affect the ALS progression rate in a subject, the pharmacokinetics of the administered compounds in a subject, and/or the efficacy of the administered compounds for a subject.

The subjects may have a mutation in the gene encoding CuZn-Superoxide Dismutase (SOD1). Mutation causes the SOD1 protein to be more prone to aggregation, resulting in the deposition of cellular inclusions that contain misfolded SOD1 aggregates (See e.g., Andersen et al., Nature Reviews Neurology 7:603-615, 2011). Over 100 different mutations in SOD1 have been linked to inherited ALS, many of which result in a single amino acid substitution in the protein. In some embodiments, the SOD1 mutation is A4V (i.e., a substitution of valine for alanine at position 4). SOD1 mutations are further described in, e.g., Rosen et al. Hum. Mol. Genet. 3, 981-987, 1994 and Rosen et al. Nature 362:59-62, 1993. In some embodiments, the subject has a mutation in the C9ORF72 gene. Repeat expansions in the C9ORF72 gene are a frequent cause of ALS, with both loss of function of C9ORF72 and gain of toxic function of the repeats being implicated in ALS (See e.g., Balendra and Isaacs, Nature Reviews Neurology 14:544-558, 2018). The methods described herein can include, prior to administration of a bile acid and a phenylbutyrate compound, detecting a SOD1 mutations and/or a C9ORF72 mutation in the subject. Methods for screening for mutations are well known in the art. Suitable methods include, but are not limited to, genetic sequencing. See, e.g., Hou et al. Scientific Reports 6:32478, 2016; and Vajda et al. Neurology 88:1-9, 2017.

Skilled practitioners will appreciate that certain factors can affect the bioavailability and metabolism of the administered compounds for a subject, and can make adjustments accordingly. These include but are not limited to liver function (e.g. levels of liver enzymes), renal function, and gallbladder function (e.g., ion absorption and secretion, levels of cholesterol transport proteins). There can be variability in the levels of exposure each subject has for the administered compounds (e.g., bile acid and a phenylbutyrate compound), differences in the levels of excretion, and in the pharmacokinetics of the compounds in the subjects being treated. Any of the factors described herein may affect drug exposure by the subject. For instance, decreased clearance of the compounds can result in increased drug exposure, while improved renal function can reduce the actual drug exposure. The extent of drug exposure may be correlated with the subject's response to the administered compounds and the outcome of the treatment.

The subject can be e.g., older than about 18 years of age (e.g., between 18-100, 18-90, 18-80, 18-70, 18-60, 18-50, 18-40, 18-30, 18-25, 25-100, 25-90, 25-80, 25-70, 25-60, 25-50, 25-40, 25-30, 30-100, 30-90, 30-80, 30-70, 30-60, 30-50, 30-40, 40-100, 40-90, 40-80, 40-70, 40-60, 40-50, 50-100, 50-90, 50-80, 50-70, 50-60, 60-100, 60-90, 60-80, 60-70, 70-100, 70-90, 70-80, 80-100, 80-90, or 90-100 years of age). The subject can have a BMI of between about 18.5-30 kg/m2 (e.g., between 18.5-28, 18.5-26, 18.5-24, 18.5-22, 18.5-20, 20-30, 20-28, 20-26, 20-24, 20-22, 22-30, 22-28, 22-26, 22-24, 24-30, 24-28, 24-26, 26-30, 26-28, or 28-30 kg/m2). Having a mutation in any of the ALS-associated genes described herein or presenting with any of the biomarkers described herein may suggest that a subject is at risk for developing ALS. Such subjects can be treated with the methods provided herein for preventative and prophylaxis purposes.

In some embodiments, the subjects have one or more symptoms of benign fasciculation syndrome (BFS) or cramp-fasciculation syndrome (CFS). BFS and CFS are peripheral nerve hyperexcitability disorders, and can cause fasciculation, cramps, pain, fatigue, muscle stiffness, and paresthesia. Methods of identifying subjects with these disorders are known in the art, such as by clinical examination and electromyography.

II. Composition

The present disclosure provides methods of treating at least one symptom of ALS in a subject, the methods including administering to the subject a bile acid or a pharmaceutically acceptable salt thereof and a phenylbutyrate compound. In some embodiments, the methods include administering a composition comprising a TURSO and a sodium phenylbutyrate to a subject.

Bile Acid

As used herein, "bile acid" refers to naturally occurring surfactants having a nucleus derived from cholanic acid substituted with a 3α-hydroxyl group and optionally with other hydroxyl groups as well, typically at the C6, C7 or C12 position of the sterol nucleus. Bile acid derivatives (e.g., aqueous soluble bile acid derivatives) and bile acids conjugated with an amine are also encompassed by the term "bile acid". Bile acid derivatives include, but are not limited to, derivatives formed at the carbon atoms to which hydroxyl and carboxylic acid groups of the bile acid are attached with other functional groups, including but not limited to halogens and amino groups. Soluble bile acids may include an aqueous preparation of a free acid form of bile acids combined with one of HCl, phosphoric acid, citric acid, acetic acid, ammonia, or arginine. Suitable bile acids include but are not limited to, taurursodiol (TURSO), ursodeoxycholic acid (UDCA), chenodeoxycholic acid (also referred to as "chenodiol" or "chenic acid"), cholic acid, hyodeoxycholic acid, deoxycholic acid, 7-oxolithocholic acid, lithocholic acid, iododeoxycholic acid, iocholic acid, taurochenodeoxycholic acid, taurodeoxycholic acid, glycoursodeoxycholic acid, taurocholic acid, glycocholic acid, or an analog, derivative, or prodrug thereof.

In some embodiments, the bile acids of the present disclosure are hydrophilic bile acids. Hydrophilic bile acids include but are not limited to, TURSO, UDCA, chenodeoxycholic acid, cholic acid, hyodeoxycholic acid, lithocholic acid, and glycoursodeoxycholic acid. Pharmaceutically acceptable salts or solvates of any of the bile acids disclosed herein are also contemplated. In some embodiments, bases commonly employed to form pharmaceutically acceptable salts of the bile acids of the present disclosure include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or trialkylamines, dicyclohexylamine; tributyl amine; pyridine; N-methyl, N-ethylamine; diethylamine; triethylamine; mono-, bis-, or tris-(2-OH—(C1-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The terms "tauroursodeoxycholic acid" (TUDCA) and "taurursodiol" (TURSO) are used interchangeably herein.

The bile acid described herein can be TURSO, as shown in formula I (with labeled carbons to assist in understanding where substitutions may be made).

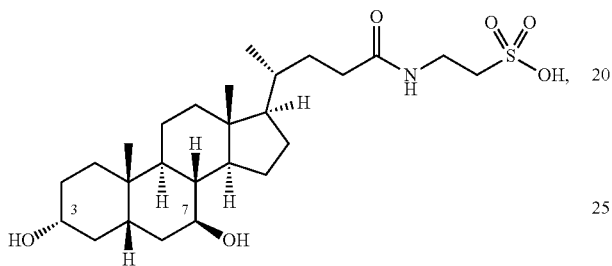

I or a pharmaceutically acceptable salt thereof.

The bile acid described herein can be UDCA as shown in formula II (with labeled carbons to assist in understanding where substitutions may be made).

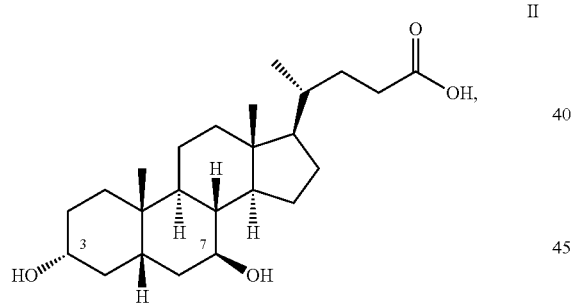

II or a pharmaceutically acceptable salt thereof.

Derivatives of bile acids of the present disclosure can be physiologically related bile acid derivatives. For example, any combination of substitutions of hydrogen at position 3 or 7, a shift in the stereochemistry of the hydroxyl group at positions 3 or 7, in the formula of TURSO or UDCA are suitable for use in the present composition.

The "bile acid" can also be a bile acid conjugated with an amino acid. The amino acid in the conjugate can be, but are not limited to, taurine, glycine, glutamine, asparagine, methionine, or carbocysteine. Other amino acids that can be conjugated with a bile acid of the present disclosure include arginine, histidine, lysine, aspartic acid, glutamic acid, serine, threonine, cysteine, proline, alanine, valine, isoleucine, leucine, phenylalanine, tyrosine, and tryptophan, as well as β-alanine, and γ-aminobutyric acid. One example of such a bile acid is a compound of formula III:

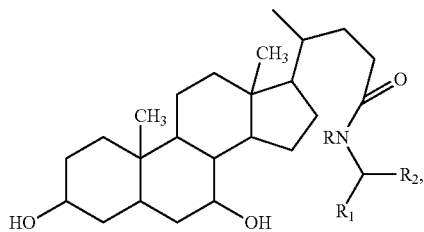

III wherein
R is —H or $C_1$-$C_4$ alkyl;
$R_1$ is —$CH_2$—$SO_3R_3$, $CH_2COOH$, or $CH_2CH_2COOH$, and $R_2$ is —H;
or $R_1$ is —COOH and $R_2$ is —$CH_2$—$CH_2$—$CONH_2$, —$CH_2$—$CONH_2$, —$CH_2$—$CH_2$—$SCH_3$, $CH_2CH_2CH_2NH(C$—$NH)NH_2$, $CH_2$(imidazolyl), $CH_2CH_2CH_2CH_2NH_2$, $CH_2COOH$, $CH_2CH_2COOH$, $CH_2OH$, $CH(OH)CH_3$, $CH_2SH$, pyrrolidin-2-yl, $CH_3$, 2-propyl, 2-butyl, 2-methylbutyl, $CH_2$(phenyl), $CH_2$(4-OH-phenyl), or —$CH_2$—S—$CH_2$—COOH; and
$R_3$ is —H or the residue of an amino acid, or a pharmaceutically acceptable analog, derivative, prodrug thereof, or a mixture thereof. One example of the amino acid is a basic amino acid. Other examples of the amino acid include glycine, glutamine, asparagine, methionine, carbocysteine, arginine, histidine, lysine, aspartic acid, glutamic acid, serine, threonine, cysteine, proline, alanine, valine, isoleucine, leucine, phenylalanine, tyrosine, and tryptophan, as well as β-alanine, and γ-aminobutyric acid.

Another example of a bile acid of the present disclosure is a compound of formula IV:

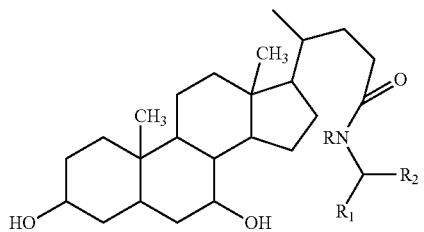

IV wherein
R is —H or $C_1$-$C_4$ alkyl; $R_1$ is —$CH_2$—$SO_3R_3$, and $R_2$ is —H;
or $R_1$ is —COOH and $R_2$ is —$CH_2$—$CH_2$—$CONH_2$, —$CH_2$—$CONH_2$, —$CH_2$—$CH_2$—$SCH_3$, or —$CH_2$—S—$CH_2$—COOH; and
$R_3$ is —H or the residue of a basic amino acid, or a pharmaceutically acceptable analog, derivative, prodrug thereof, or a mixture thereof. Examples of basic amino acids include lysine, histidine, and arginine.

In some embodiments, the bile acid is TURSO. TURSO is an ambiphilic bile acid and is the taurine conjugate form of UDCA. TURSO recovers mitochondrial bioenergetic deficits through incorporating into the mitochondrial membrane, reducing Bax translocation to the mitochondrial membrane, reducing mitochondrial permeability, and increasing the apoptotic threshold of the cell (Rodrigues et al. Biochemistry 42, 10: 3070-3080, 2003). It is used for the treatment of cholesterol gallstones, where long periods of treatment is generally required (e.g., 1 to 2 years) to obtain complete dissolution. It has been used for the treatment of cholestatic liver diseases including primary cirrhosis, pediatric familial intrahepatic cholestasis and primary sclerosing cholangitis and cholestasis due to cystic fibrosis. TURSO is contraindicated in subjects with biliary tract infections, frequent biliary colic, or in subjects who have trouble absorbing bile acids (e.g. ileal disease or resection). Drug interactions may include with substances that inhibit the absorption of bile acids, such as cholestyramine, and with drugs that increase the elimination of cholesterol in the bile (TURSO reduces biliary cholesterol content). Based on similar physicochemical characteristics, similarities in drug toxicity and interactions exist between TURSO and UDCA. The most common adverse reactions reported with the use of TURSO (≥1%) are: abdominal discomfort, abdominal pain, diarrhea, nausea, pruritus, and rash. There are some cases of pruritus and a limited number of cases of elevated liver enzymes.

In some embodiments, the bile acid is UDCA. UDCA, or ursodiol, has been used for treating gallstones, and is produced and secreted endogenously by the liver as a taurine (TURSO) or glycine (GUDCA) conjugate. Taurine conjugation increases the solubility of UDCA by making it more hydrophilic. TURSO is taken up in the distal ileum under active transport and therefore likely has a slightly a longer dwell time within the intestine than UDCA which is taken up more proximally in the ileum. Ursodiol therapy has not been associated with liver damage. Abnormalities in liver enzymes have not been associated with Actigall® (Ursodiol USP capsules) therapy and, Actigall® has been shown to decrease liver enzyme levels in liver disease. However, subjects given Actigall® should have SGOT (AST) and SGPT (ALT) measured at the initiation of therapy and thereafter as indicated by the particular clinical circumstances. Previous studies have shown that bile acid sequestering agents such as cholestyramine and colestipol may interfere with the action of ursodiol by reducing its absorption. Aluminum-based antacids have been shown to adsorb bile acids in vitro and may be expected to interfere with ursodiol in the same manner as the bile acid sequestering agents. Estrogens, oral contraceptives, and clofibrate (and perhaps other lipid-lowering drugs) increase hepatic cholesterol secretion, and encourage cholesterol gallstone formation and hence may counteract the effectiveness of ursodiol.

Phenylbutyrate Compounds

Phenylbutyrate compound is defined herein as encompassing phenylbutyrate (a low molecular weight aromatic carboxylic acid) as a free acid (4-phenylbutyrate (4-PBA), 4-phenylbutyric acid, or phenylbutyric acid), and pharmaceutically acceptable salts, co-crystals, polymorphs, hydrates, solvates, conjugates, derivatives or pro-drugs thereof. Phenylbutyrate compounds described herein also encompass analogs of 4-PBA, including but not limited to Glyceryl Tri-(4-phenylbutyrate), phenylacetic acid (which is the active metabolite of PBA), 2-(4-Methoxyphenoxy) acetic acid (2-POAA-OMe), 2-(4-Nitrophenoxy) acetic acid (2-POAA-NO2), and 2-(2-Naphthyloxy) acetic acid (2-NOAA), and their pharmaceutically acceptable salts. Phenylbutyrate compounds also encompass physiologically related 4-PBA species, such as but not limited to any substitutions for Hydrogens with Deuterium in the structure of 4-PBA. Other HDAC2 inhibitors are contemplated herein as substitutes for phenylbutyrate compounds.

Physiologically acceptable salts of phenylbutyrate, include, for example sodium, potassium, magnesium or calcium salts. Other example of salts include ammonium, zinc, or lithium salts, or salts of phenylbutyrate with an orgain amine, such as lysine or arginine.

In some embodiments of any of the methods described herein, the phenylbutyrate compound is sodium phenylbutyrate. Sodium phenylbutyrate has the following formula:

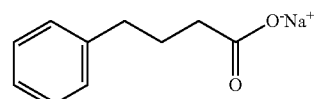

Phenylbutyrate is a pan-HDAC inhibitor and can ameliorate ER stress through upregulation of the master chaperone regulator DJ-1 and through recruitment of other chaperone proteins (See e.g., Zhou et al. J Biol Chem. 286: 14941-14951, 2011 and Suaud et al. JBC. 286:21239-21253, 2011). The large increase in chaperone production reduces activation of canonical ER stress pathways, folds misfolded proteins, and has been shown to increase survival in in vivo models including the G93A SOD1 mouse model of ALS (See e.g., Ryu, H et al. J Neurochem. 93:1087-1098, 2005).

In some embodiments, the combination of a bile acid (e.g., TURSO), or a pharmaceutically acceptable salt thereof, and a phenylbutyrate compound (e.g., sodium phenylbutyrate) has synergistic efficacy when dosed in particular ratios (e.g., any of the ratios described herein), in treating one or more symptoms associated with ALS. The combination can, for example, induce a mathematically synergistic increase in neuronal viability in a strong oxidative insult model (14202-mediated toxicity) by linear modeling, through the simultaneous inhibition of endoplasmic reticulum stress and mitochondrial stress (See, e.g. U.S. Pat. Nos. 9,872,865 and 10,251,896).

Formulation

Bile acids and phenylbutyrate compounds described herein can be formulated for use as or in pharmaceutical compositions. For example, the methods described herein can include administering an effective amount of a composition comprising TURSO and sodium phenylbutyrate. The term "effective amount", as used herein, refer to an amount or a concentration of one or more drugs for a period of time (including acute or chronic administration and periodic or continuous administration) that is effective within the context of its administration for causing an intended effect or physiological outcome. The composition can include about 5% to about 15% w/w (e.g., about 6% to about 14%, about 7% to about 13%, about 8% to about 12%, about 8% to about 11%, about 9% to about 10%, or about 9.7% w/w) of TURSO and about 15% to about 45% w/w (e.g., about 20% to about 40%, about 25% to about 35%, about 28% to about 32%, or about 29% to about 30%, e.g., about 29.2% w/w) of sodium phenylbutyrate. In some embodiments, the composition includes about 9.7% w/w of TURSO and 29.2% w/w of sodium phenylbutyrate.

The sodium phenylbutyrate and TURSO can be present in the composition at a ratio by weight of between about 1:1 to about 4:1 (e.g., about 2:1 or about 3:1). In some embodiments, the ratio between sodium phenylbutyrate and TURSO is about 3:1.

The compositions described herein can include any pharmaceutically acceptable carrier, adjuvant, and/or vehicle. The term "pharmaceutically acceptable carrier or adjuvant" refers to a carrier or adjuvant that may be administered to a patient, together with a compound disclosed herein, and which does not destroy the pharmacological activity thereof and is nontoxic when administered in doses sufficient to deliver a therapeutic amount of the compound. As used herein the language "pharmaceutically acceptable carrier" includes saline, solvents, dispersion media, coatings, antibacterial and antifungal agents, isotonic and absorption delaying agents, and the like, compatible with pharmaceutical administration. The pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

Compositions of the present disclosure can include about 8% to about 24% w/w of dextrates (e.g., about 9% to about 23%, about 10% to about 22%, about 10% to about 20%, about 11% to about 21%, about 12% to about 20%, about 13% to about 19%, about 14% to about 18%, about 14% to about 17%, about 15% to about 16%, or about 15.6% w/w of dextrates). Both anhydrous and hydrated dextrates are contemplated herein. The dextrates of the present disclosure can include a mixture of saccharides developed from controlled enzymatic hydrolysis of starch. Some embodiments of any of the compositions described herein include hydrated dextrates (e.g., NF grade, obtained from JRS Pharma, Colonial Scientific, or Quadra).

Compositions of the present disclosure can include about 1% to about 6% w/w of sugar alcohol (e.g., about 2% to about 5%, about 3% to about 4%, or about 3.9% w/w of sugar alcohol). Sugar alcohols can be derived from sugars and contain one hydroxyl group (—OH) attached to each carbon atom. Both disaccharides and monosaccharides can form sugar alcohols. Sugar alcohols can be natural or produced by hydrogenation of sugars. Exemplary sugar alcohols include but are not limited to, sorbitol, xylitol, and mannitol. In some embodiments, the composition comprises about 1% to about 6% w/w (e.g., about 2% to about 5%, about 3% to about 4%, or about 3.9% w/w) of sorbitol.

Compositions of the present disclosure can include about 22% to about 35% w/w of maltodextrin (e.g., about 22% to about 33%, about 24% to about 31%, about 25% to about 32%, about 26% to about 30%, or about 28% to about 29% w/w, e.g., about 28.3% w/w of maltodextrin). Maltodextrin can form a flexible helix enabling the entrapment of the active ingredients (e.g., any of the phenylbutyrate compounds and bile acids described herein) when solubilized into solution, thereby masking the taste of the active ingredients. Maltodextrin produced from any suitable sources are contemplated herein, including but not limited to, pea, rice, tapioca, corn, and potato. In some embodiments, the maltodextrin is pea maltodextrin. In some embodiments, the composition includes about 28.3% w/w of pea maltodextrin. For example, pea maltodextrin obtained from Roquette (KLEPTOSE® LINECAPS) can be used.

The compositions described herein can further include sugar substitutes (e.g. sucralose). For example, the compositions can include about 0.5% to about 5% w/w of sucralose (e.g., about 1% to about 4%, about 1% to about 3%, or about 1% to about 2%, e.g., about 1.9% w/w of sucralose). Other sugar substitutes contemplated herein include but are not limited to aspartame, neotame, acesulfame potassium, saccharin, and advantame.

In some embodiments, the compositions include one or more flavorants. The compositions can include about 2% to about 15% w/w of flavorants (e.g., about 3% to about 13%, about 3% to about 12%, about 4% to about 9%, about 5% to about 10%, or about 5% to about 8%, e.g., about 7.3% w/w). Flavorants can include substances that give another substance flavor, or alter the characteristics of a composition by affecting its taste. Flavorants can be used to mask unpleasant tastes without affecting physical and chemical stability, and can be selected based on the taste of the drug to be incorporated. Suitable flavorants include but are not limited to natural flavoring substances, artificial flavoring substances, and imitation flavors. Blends of flavorants can also be used. For example, the compositions described herein can include two or more (e.g., two, three, four, five or more) flavorants. Flavorants can be soluble and stable in water. Selection of suitable flavorants can be based on taste testing. For example, multiple different flavorants can be added to a composition separately, which are subjected to taste testing. Exemplary flavorants include any fruit flavor powder (e.g., peach, strawberry, mango, orange, apple, grape, raspberry, cherry or mixed berry flavor powder). The compositions described herein can include about 0.5% to about 1.5% w/w (e.g., about 1% w/w) of a mixed berry flavor powder and/or about 5% to about 7% w/w (e.g., about 6.3% w/w) of a masking flavor. Suitable masking flavors can be obtained from e.g., Firmenich.

The compositions described herein can further include silicon dioxide (or silica). Addition of silica to the composition can prevent or reduce agglomeration of the components of the composition. Silica can serve as an anti-caking agent, adsorbent, disintegrant, or glidant. In some embodiments, the compositions described herein include about 0.1% to about 2% w/w of porous silica (e.g., about 0.3% to about 1.5%, about 0.5% to about 1.2%, or about 0.8% to about 1%, e.g., 0.9% w/w). Porous silica may have a higher $H_2O$ absorption capacity and/or a higher porosity as compared to fumed silica, at a relative humidity of about 20% or higher (e.g., about 25%, 30%, 35%, 40%, 45%, 50%, 55%, 60%, 65%, 70%, 75%, 80%, 85%, 90%, or 95% or higher). The porous silica can have an $H_2O$ absorption capacity of about 5% to about 40% (e.g. about 20% to about 40%, or about 30% to about 40%) by weight at a relative humidity of about 50%. The porous silica can have a higher porosity at a relative humidity of about 20% or higher (e.g., about 30%, 40%, 50%, 60%, 70%, 80%, 90% or higher) as compared to that of fumed silica. In some embodiments, the porous silica have an average particle size of about 2 μm to about 10 μm (e.g. about 3 μm to about 9 μm, about 4 μm to about 8 μm, about 5 μm to about 8 μm, or about 7.5 μm). In some embodiments, the porous silica have an average pore volume of about 0.1 cc/gm to about 2.0 cc/gm (e.g., about 0.1 cc/gm to about 1.5 cc/gm, about 0.1 cc/gm to about 1 cc/gm, about 0.2 cc/gm to about 0.8 cc/gm, about 0.3 cc/gm to about 0.6 cc/gm, or about 0.4 cc/gm). In some embodiments, the porous silica have a bulk density of about 50 g/L to about 700 g/L (e.g. about 100 g/L to about 600 g/L, about 200 g/L to about 600 g/L, about 400 g/L to about 600 g/L, about 500 g/L to about 600 g/L, about 540 g/L to about 580 g/L, or about 560 g/L). In some embodiments, the compositions described herein include about 0.05% to about 2% w/w (e.g., any subranges of this range described herein) of Syloid® 63FP (WR Grace).

The compositions described herein can further include one or more buffering agents. For example, the compositions can include about 0.5% to about 5% w/w of buffering agents (e.g., about 1% to about 4% w/w, about 1.5% to about 3.5% w/w, or about 2% to about 3% w/w, e.g. about 2.7% w/w of buffering agents). Buffering agents can include weak acid or base that maintain the acidity or pH of a composition near a chosen value after addition of another acid or base. Suitable buffering agents are known in the art. In some embodiments, the buffering agent in the composition provided herein is a phosphate, such as a sodium phosphate (e.g., sodium phosphate dibasic anhydrous). For example, the composition can include about 2.7% w/w of sodium phosphate dibasic.

The compositions can also include one or more lubricants. For example, the compositions can include about 0.05% to about 1% w/w of lubricants (e.g., about 0.1% to about 0.9%, about 0.2% to about 0.8%, about 0.3% to about 0.7%, or about 0.4% to about 0.6%, e.g. about 0.5% w/w of lubricants). Exemplary lubricants include, but are not limited to sodium stearyl fumarate, magnesium stearate, stearic acid, metallic stearates, talc, waxes and glycerides with high melting temperatures, colloidal silica, polyethylene glycols, alkyl sulphates, glyceryl behenate, and hydrogenated oil. Additional lubricants are known in the art. In some embodiments, the composition includes about 0.05% to about 1% w/w (e.g., any of the subranges of this range described herein) of sodium stearyl fumarate. For example, the composition can include about 0.5% w/w of sodium stearyl fumarate.

In some embodiments, the composition include about 29.2% w/w of sodium phenylbutyrate, about 9.7% w/w of TURSO, about 15.6% w/w of dextrates, about 3.9% w/w of sorbitol, about 1.9% w/w of sucralose, about 28.3% w/w of maltodextrin, about 7.3% w/w of flavorants, about 0.9% w/w of silicon dioxide, about 2.7% w/w of sodium phosphate (e.g. sodium phosphate dibasic), and about 0.5% w/w of sodium stearyl fumarate.

The composition can include about 3000 mg of sodium phenylbutyrate, about 1000 mg of TURSO, about 1600 mg of dextrates, about 400 mg of sorbitol, about 200 mg of sucralose, about 97.2 mg of silicon dioxide, about 2916 mg of maltodextrin, about 746 mg of flavorants (e.g. about 102 mg of mixed berry flavor and about 644 mg of masking flavor), about 280 mg of sodium phosphate (e.g. sodium phosphate dibasic), and about 48.6 mg of sodium stearyl fumarate.

Additional suitable sweeteners or taste masking agents can also be included in the compositions, such as but not limited to, xylose, ribose, glucose, mannose, galactose, fructose, dextrose, sucrose, maltose, steviol glycosides, partially hydrolyzed starch, and corn syrup solid. Water soluble artificial sweeteners are contemplated herein, such as the soluble saccharin salts (e.g., sodium or calcium saccharin salts), cyclamate salts, acesulfam potassium (acesulfame K), and the free acid form of saccharin and aspartame based sweeteners such as L-aspartyl-phenylalanine methyl ester, Alitame® or Neotame®. The amount of sweetener or taste masking agents can vary with the desired amount of sweeteners or taste masking agents selected for a particular final composition.

Pharmaceutically acceptable binders in addition to those described above are also contemplated. Examples include cellulose derivatives including microcrystalline cellulose, low-substituted hydroxypropyl cellulose (e.g. LH 22, LH 21, LH 20, LH 32, LH 31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); and sodium carboxymethyl starch (e.g. Primogel® and Explotab®).

Additional fillers, diluents or binders may be incorporated such as polyols, sucrose, sorbitol, mannitol, Erythritol®, Tagatose®, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-RPC-CH31, L-RPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium sulfate, and calcium carbonate.

The compositions described herein can be formulated or adapted for administration to a subject via any route (e.g. any route approved by the Food and Drug Administration (FDA)). Exemplary methods are described in the FDA's CDER Data Standards Manual, version number 004 (which is available at fda.give/cder/dsm/DRG/drg00301.html).

Pharmaceutical compositions are typically formulated to be compatible with its intended route of administration. Examples of routes of administration include parenteral (subcutaneous, intracutaneous, intravenous, intradermal, intramuscular, intra-articular, intraarterial, intrasynovial, intrasternal, intrathecal, intralesional and intracranial injection or infusion techniques), oral (e.g., inhalation or through a feeding tube), transdermal (topical), transmucosal, and rectal administration.

Pharmaceutical compositions can be in the form of a solution or powder for inhalation and/or nasal administration. In some embodiments, the pharmaceutical composition is formulated as a powder filled sachet. Suitable powders may include those that are substantially soluble in water. Pharmaceutical compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions can be orally administered in any orally acceptable dosage form including, but not limited to, powders, capsules, tablets, emulsions and aqueous suspensions, dispersions and solutions. In the case of powders for oral administration, the powders can be substantially dissolved in water prior to administration. In the case of tablets for oral use, carriers which are commonly used include lactose and corn starch. Lubricating agents, such as magnesium stearate, may be added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, the compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, therapeutic compositions disclosed herein can be formulated for sale in the US, imported into the US, and/or exported from the US. The pharmaceutical compositions can be included in a container, pack, or dispenser together with instructions for administration. In some embodiments, the invention provides kits that include the bile acid and phenylbutyrate compounds. The kit may also include instructions for the physician and/or patient, syringes, needles, box, bottles, vials, etc.

III. Methods of Treatment

Applicant has discovered that a combination of a bile acid (e.g. TURSO) and a phenylbutyrate compound (e.g. sodium phenylbutyrate) can be used for treating one or more symptoms of ALS. Applicant has discovered that TURSO and its metabolites, ursodeoxycholic acid and glycoursodeoxycholic acid, are inhibitors of B SEP. It was also discovered that, phenylacetic acid, a metabolite of sodium phenylbutyrate was surprisingly found to inhibit B SEP. Therefore, when inhibitors of BSEP are administered concomitantly with a composition comprising a bile acid and a phenylbutyrate compound, drug-drug interactions can result leading to an exacerbation of accumulation of conjugated bile salts in the liver, thereby leading to adverse events. Accordingly, when inhibitors of BSEP and a composition comprising, e.g. TURSO and sodium phenylbutyrate are administered concomitantly to a subject in need of both treatment, signs of drug-drug interactions can be monitored, and the dose of the inhibitors of BSEP can be adjusted accordingly. For example, when BSEP inhibitors are administered concomitantly with a composition comprising TURSO and sodium phenylbutyrate, the levels of serum transaminases and bilirubin can be elevated, indicating liver toxicity. Monitoring of serum transaminases and bilirubin, and adjusting the dosage of the inhibitors of BSEP can therefore prevent or reduce the adverse effects associated with the drug-drug interaction.

Accordingly, the present disclosure provides methods of treating at least one symptom of ALS in a subject who is receiving a B SEP inhibitor, by adjusting the dosage of the B SEP inhibitor. Such adjustment may provide similar plasma concentrations of the BSEP inhibitor as, and may be as effective as, the dosage of BSEP inhibitor administered in the absence of the bile acid and the phenylbutyrate compound.

Applicant discloses herein methods for treating at least one symptom of ALS in a subject who has received a first dosage of a BSEP inhibitor, the method including administering to the subject a composition comprising about 1 gram of TURSO and about 3 grams of sodium phenylbutyrate, monitoring the subject for response to the BSEP inhibitor, and administering a second dosage of the BSEP inhibitor, wherein the second dosage is less than the first dosage. Monitoring the subject for response to the BSEP inhibitor can include determining a first level of serum transaminases and/or bilirubin in a biological sample from the subject, monitoring for known adverse events, and/or overdose symptoms or side effects associated with BSEP inhibition, or elevated levels of serum transaminsases or bilirubin levels.

In some embodiments of any of the methods described herein, the first and/or second dosage of the BSEP inhibitor can be a daily (once, twice, or three times daily), once every two days, three times a week, or a weekly dosage, or a dosage based on some other basis. The second dosage of the BSEP inhibitor can be less than the first dosage by about 1% to about 95% (e.g., about 5%, 10%, 15%, 20%, 25%, 30%, 35%, 40%, 45%, 50%, 55%, 60%, 65%, 70%, 75%, 80%, 85%, or 90%). In some instances, the second dosage involves administering the same or similar amount per administration but is less frequent as compared to the first dosage. In some instances, the administration of the BSEP inhibitor is stopped, i.e., there is no second dosage.

In some embodiments of any of the methods described herein, the methods include a step of determining or having determined a second level of serum transaminases and/or bilirubin in a second biological sample from the subject. In some embodiments, the second level is lower than the first level.

In some embodiments of any of the methods described herein, the first biological sample can be obtained from the subject about 1 hour to about 72 hours (e.g. about 2, 4, 6, 8, 10, 16, 24, 32, 48, or 56 hours) after administration of the composition comprising TURSO and phenylbutyrate. The second biological sample can be taken from the subject about 1 hour to about 72 hours (e.g. about 2, 4, 6, 8, 10, 16, 24, 32, 48, or 56 hours) after administration of the second dosage of the B SEP inhibitor.

In some embodiments of any of the methods described herein, the first and/or second biological sample can be a serum, plasma, urine, or saliva sample. Methods of measuring serum transaminases and/or bilirubin levels in a biological sample are known in the art.

BSEP Inhibitors

Transporters can be divided into (i) efflux transporters belonging to the ATP-binding cassette (ABC) family and (ii) uptake transporters belonging to the solute carrier (SLC) family that mediate the influx or bidirectional movement across the cell membrane. Efflux transporters pump compounds back into the blood as they traverse the apical cell membrane (i.e., the blood side) and also pump compounds out of the cell into the brain on the basolateral side.

Bile formation is one of the key functions of mammalian liver. It involves vectorial secretion of bile acids and other cholephilic compounds across hepatocytes from the sinusoidal blood plasma into bile canaliculi. Thereby, bile acids or bile salts are concentrated more than 500-fold in bile as compared to blood plasma. This concentrative process is dependent on ATP and mainly driven by the canalicular bile salt export pump (B SEP). B SEP is a member of the B-family of the ATPbinding cassette (ABC) superfamily of transporters and is classified as ABCB11.

Inhibition of B SEP leads to reduced bile salt secretion and decreased bile flow, a process which results in cholestasis. Cholestasis is a liver disease. Those with cholestasis experience: pain in the abdomen, bloating, fat in stool, nausea, or pale feces, loss of appetite or malaise, dark urine, failure to thrive, itching, or yellow skin and eyes, abnormal levels of bilirubin, and/or abnormal levels of liver enzymes.

Many known drugs are BSEP inhibitors. Such drugs may, in susceptible humans, cause acquired cholestasis, which rapidly resolves after the withdrawal of the drug. Exemplary inhibitors of BSEP include but are not limited to: cyclosporine, glybenclamide, rifamycin, bosentan, troglitazone, fluvastatin, ketoconazole.

As noted above, Applicant has discovered that TURSO and its metabolites, ursodeoxycholic acid and glycoursodeoxycholic acid, are inhibitors of BSEP. It was also discovered that, phenylacetic acid, a metabolite of sodium phenylbutyrate was surprisingly found to inhibit B SEP. Concomitant usage of a BSEP inhibitor and a a composition comprising a bile acid and a phenylbutyrate compound can lead to drug-drug interactions resulting in an exacerbation of accumulation of conjugated bile salts in the liver, thereby leading to adverse events, e.g., the levels of serum transaminases and bilirubin can increase resulting in toxic effects.

Accordingly, provided herein in some aspects, are methods of treating at least one symptom of ALS in a subject, including (a) administering to a subject who has received a first dosage of a BSEP inhibitor an effective amount of a composition comprising about 1 gram of TURSO and about 3 grams of sodium phenylbutyrate; (b) determining or having determined a first level of serum transaminases and/or bilirubin in a first biological sample from the subject; and (c) administering to the subject a second dosage of the BSEP inhibitor, wherein the second dosage is lower than the first dosage. The methods can further include step (d), determining or having determined a second level of the serum transaminases and/or bilirubin in a second biological sample from the subject.

In some embodiments, the BSEP inhibitor is cyclosporine. Cyclosporine (also referred to as Cyclosporine A) can be used for the prophylaxis of organ rejection in allogeneic kidney, liver, and heart transplants, or to prevent bone marrow transplant rejection. Cyclosporine is used for the treatment of patients with severe active rheumatoid arthritis (RA), or severe, recalcitrant, plaque psoriasis. The ophthalmic solution of cyclosporine is indicated to increase tear production in patients suffering from keratoconjunctivitis sicca. In addition, cyclosporine is approved for the treatment of steroid dependent and steroid-resistant nephrotic syndrome due to glomerular diseases which may include minimal change nephropathy, focal and segmental glomerulosclerosis or membranous glomerulonephritis. Cyclosporine is also commonly used for the treatment of various autoimmune and inflammatory conditions such as atopic dermatitis, blistering disorders, ulcerative colitis, juvenile rheumatoid arthritis, uveitis, connective tissue diseases, as well as idiopathic thrombocytopenic purpura. The subject may have received a first dosage of cyclosporine at about 0.5 to about 15 mg/kg/day of body weight (e.g., about 0.5 to about 5 mg/kg/day, about 1 to about 4 mg/kg/day, about 2.5 mg/kg/day, or about 12 to about 15 mg/kg/day). The second dosage of cyclosporine can be less than the first dosage by about 0.1 to about 14 mg/kg/day (e.g., about 0.5 to about 2.5 mg/kg/day, about 1 to about 5 mg/kg/day).

In addition to or instead of determining the first and/or second level of the BSEP inhibitor in a biological sample from the subject, other methods of monitoring the subject's response to the first dosage of the BSEP inhibitor are also contemplated herein. For instance, known adverse events, side effects, or symptoms of overdose associated with the BSEP inhibitor can be monitored. For example, in some embodiments, monitoring a subject for cholestasis. As noted above, symptoms of cholestasis include: pain in the abdomen, bloating, fat in stool, nausea, or pale feces, loss of appetite or malaise, dark urine, failure to thrive, itching, or yellow skin and eyes. Cyclosporine overdose symptoms can include hepatotoxicity and nephrotoxicity.

Measuring Liver Function

Drug metabolism can have an effect on liver function. Liver function tests check the levels of certain enzymes and proteins in your blood. Levels that are higher or lower than normal can indicate liver problems. For example, testing levels of one or more of the following: alanine transaminase, aspartate transaminase, alkaline phosphatase, albumin and total protein, bilirubin, gamma-glutamyltransferase, L-lactate dehydrogenase, and prothrombin time (to measure blood clotting factors).

Serum Transaminases

Serum transaminases include alanine transaminase (ALT) and aspartate transaminase (AST). Serum transaminases (also referred to as aminotransferases) are a group of enzymes that catalyze the interconversion of amino acids and oxoacids by transfer of amino groups. ALT and AST are two of the most reliable markers of hepatocellular injury or necrosis. Their levels can be elevated in a variety of hepatic disorders.

Normal ranges of ALT and AST can vary based on sex, age, and laboratory. Individuals with elevated levels of serum transaminases can be classified as "mild" (<5 times the normal range), "moderate" (5-10 times the normal range) or "marked" (>10 times the normal range). Accordingly, in some embodiments of the methods described herein, the methods include determining a first level of ALT or AST in a sample of the subject. In some instances, the first level of ALT or AST can be higher than a normal range of ALT or AST by about 5 times, by above 5-10 times, or greater than 5 times the normal range.

Methods of measuring levels of serum transaminases are well known in the art. Typically, levels of ALT and AST are measured from a patient's blood sample and commonly tested with other liver enzymes and compounds in the blood. For example, immuno/enzyme-immnoassays or liquid chromatography/tandem mass spectrometry (LC/MS) can be used.

Bilirubin

Bilirubin (BR) is a yellowish-orange compound that occurs in the normal catabolic pathway that breaks down heme in the liver of vertebrates. Elevated levels of bilirubin are indicative of liver disease. There are three types of bilirubin: unconjugated, conjugated, and total (combination of both unconjugated and conjugated). Unconjugated (also referred to as "indirect") bilirubin is the bilirubin created from red blood cell breakdown. It travels in the blood to the liver. Conjugated (also referred to as "direct") bilirubin is the bilirubin once it reaches the liver and undergoes a chemical change. It moves to the intestines before being removed through the urine and stool. Bilirubin tests can look at unconjugated, conjugated, and total amounts of bilirubin. For example, for adults over 18 years of age, normal total bilirubin can be up to 1.2 milligrams per deciliter (mg/dl) of blood. For those under 18 years of age, the normal level can be around 1 mg/dl. Normal results for conjugated (direct) bilirubin can be less than 0.3 mg/dl.

Some embodiments of the methods described herein include determining a first level of bilirubin in a sample of the subject etc. The first level of bilirubin can be higher than a normal range of bilirubin by about X. In some embodiments, a subject can have an elevated level of total bilirubin of >1.2 mg/dl, e.g., 1.3, 1.4, 1.5, 1.6, 1.7, 1.8, 1.9, 2.0 mg/dl, or greater. In some embodiments, a subject can have an elevated level of direct bilirubin of >0.3 mg/dl, e.g, 0.4, 0.5, 0.6, 0.7, 0.8, 0.9, 1.0 mg/dl, or greater.

Methods of measuring levels of bilirubin are well known in the art. Typically, levels of bilirubin is measured from a patient's blood sample and commonly tested with other liver enzymes and compounds in the blood, similar to ALT and AST. Bilirubin blood tests can be used to measure the amount of total bilirubin present in the blood. Bilirubin can also be tested from urine samples. The urinary bilirubin test measures whether or not bilirubin is present in the urine. Similar to ALT and AST, immuno/enzyme-immnoassays or liquid chromatography/tandem mass spectrometry (LC/MS) can be used to measure bilirubin levels.

Administration of TURSO and Sodium Phenylbutyrate

The methods described herein include administering to the subject a bile acid or pharmaceutically acceptable salt thereof, and a phenylbutyrate compound. The bile acid or a pharmaceutically acceptable salt thereof and the phenylbutyrate compound can be administered separately or concurrently, including as a part of a regimen of treatment. The compounds can be administered daily (e.g. once a day, twice a day, or three times a day or more), weekly, monthly, or quarterly. The compounds can be administered over a period of weeks, months, or years. For example, the compounds can be administered over a period of at least or about 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, or at least or about 5 years, or more. The compounds can be administered once a day or twice a day for 60 days or less (e.g., 55 days, 50 days, 45 days, 40 days, 35 days, 30 days or less). Alternatively, the bile acid and phenylbutyrate compound can be administered once a day or twice a day for more than 60 days (e.g., more than 65, 70, 75, 80, 85, 90, 95, 100, 105, 110, 115, 120, 130, 140, 150, 160, 180, 200, 250, 300, 400, 500, 600 days).

In some embodiments, the methods provided herein include administering an effective amount of a composition comprising about 1 gram of TURSO and about 3 grams of sodium phenylbutyrate. TURSO can be administered at an amount of about 0.5 to about 5 grams per day (e.g., about 0.5 to about 4.5, about 0.5 to about 4, about 0.5 to about 3.5, about 0.5 to about 3, about 0.5 to about 2.5, about 0.5 to about 2, about 0.5 to about 1.5, about 0.5 to about 1, about 1 to about 5, about 1 to about 4.5, about 1 to about 4, about 1 to about 3.5, about 1 to about 3, about 1 to about 2.5, about 1 to about 2, about 1 to about 1.5, about 1.5 to about 5, about 1.5 to about 4.5, about 1.5 to about 4, about 1.5 to about 3.5, about 1.5 to about 3, about 1.5 to about 2.5, about 1.5 to about 2, about 2 to about 5, about 2 to about 4.5, about 2 to about 4, about 2 to about 3.5, about 2 to about 3, about 2 to about 2.5, about 2.5 to about 5, about 2.5 to about 4.5, about 2.5 to about 4, about 2.5 to about 3.5, about 2.5 to about 3, about 3 to about 5, about 3 to about 4.5, about 3 to about 4, about 3 to about 3.5, about 3.5 to about 5 about 3.5 to about 4.5, about 3.5 to about 4, about 4 to about 5, about 4 to about 4.5, or about 4.5 to about 5 grams). In some embodiments, TURSO is administered at an amount of about 1 to about 2 grams per day, inclusive (e.g., about 1 to about 1.8 grams, about 1 to about 1.6 grams, about 1 to about 1.4 grams, about 1 to about 1.2 grams, about 1.2 to about 2.0 grams, about 1.2 to about 1.8 grams, about 1.2 to about 1.6 grams, about 1.2 to about 1.4 grams, about 1.4 to about 2.0 grams, about 1.4 to about 1.8 grams, about 1.4 to about 1.6 grams, about 1.6 to about 2.0 grams, about 1.6 to about 1.8 grams, about 1.8 to about 2.0 grams). In some embodiments, TURSO is administered at an amount of about 1 gram per day. In some embodiments, TURSO is administered at an amount of about 2 grams per day. For example, TURSO can be administered at an amount of about 1 gram twice a day.

Sodium phenylbutyrate can be administered at an amount of about 0.5 to about 10 grams per day (e.g., about 1 to about 10, about 1 to about 9, about 1 to about 8, about 1 to about 7, about 1 to about 6, about 1 to about 5, about 1 to about 4, about 1 to about 3, about 1 to about 2, about 2 to about 10, about 2 to about 9, about 2 to about 8, about 2 to about 7, about 2 to about 6, about 2 to about 5, about 2 to about 4, about 2.5 to about 9.5, about 2.5 to about 8.5, about 2.5 to about 7.5, about 2.5 to about 6.5, about 2.5 to about 5.5, about 2.5 to about 4.5, about 3 to about 10, about 3 to about 9, about 3 to about 8, about 3 to about 7, about 3 to about 6.5, about 3 to about 6, about 3 to about 5, about 4 to about 10, about 4 to about 9, about 4 to about 8, about 4 to about 7, about 4 to about 6, about 5 to about 10, about 5 to about 9, about 5 to about 8, about 5 to about 7, about 6 to about 10, about 6 to about 9, about 6 to about 8, about 7 to about 10, about 7 to about 9, about 8 to about 10 grams per day). In some embodiments, sodium phenylbutyrate is administered at an amount of about 3 to about 6 grams per day, inclusive (e.g., about 3 to about 5.5 grams, about 3 to about 5.0 grams, about 3 to about 4.5 grams, about 3 to about 4.0 grams, about 3 to about 3.5 grams, about 3.5 to about 6 grams, about 3.5 to about 5.5 grams, about 3.5 to about 5.0 grams, about 3.5 to about 4.5 grams, about 3.5 to about 4.0 grams, about 4.0 to about 6 grams, about 4.0 to about 5.5 grams, about 4.0 to about 5.0 grams, about 4.0 to about 4.5 grams, about 4.5 to about 6 grams, about 4.5 to about 5.5 grams, about 4.5 to about 5.0 grams, about 5.0 to about 6 grams, about 5.0 to about 5.5 grams, or about 5.5 to about 6.0 grams). In some embodiments, sodium phenylbutyrate is administered at an amount of about 3 grams per day. In some embodiments, sodium phenylbutyrate is administered at an amount of about 6 grams per day. For example, sodium phenylbutyrate can be administered at an amount of about 3 grams twice a day. In some embodiments, the bile acid and phenylbutyrate compound are administered at a ratio by weight of about 2.5:1 to about 3.5:1 (e.g., about 3:1).

The methods described herein can include administering about 1 gram of TURSO once a day and about 3 grams of sodium phenylbutyrate once a day, or about 1 gram of TURSO twice a day and about 3 grams of sodium phenylbutyrate twice a day. The methods can include administering about 1 gram of TURSO once a day and about 3 grams of sodium phenylbutyrate once a day for at least 14 days (e.g., at least 15, 16, 17, 18, 19, 20, 21, 22, 23, 24, 27, 30, 35, or 40 days), followed by administering about 1 gram of TURSO twice a day and about 3 grams of sodium phenylbutyrate twice a day or at least a day (e.g. at least 30, 40, 50, 60, 80, 100, 120, 150, 180, 250, 300, or 400 days). For example, the methods can include administering about 1 gram of TURSO once a day and about 3 grams of sodium phenylbutyrate once a day for 14-21 days, followed by administering about 1 gram of TURSO twice a day and about 3 grams of sodium phenylbutyrate twice a day.

In some embodiments, the methods described herein include administering to a subject about 10 mg/kg to about 50 mg/kg of body weight of TURSO per day (e.g., about 10 mg/kg to about 48 mg/kg, about 10 mg/kg to about 46 mg/kg, about 10 mg/kg to about 44 mg/kg, about 10 mg/kg to about 42 mg/kg, about 10 mg/kg to about 40 mg/kg, about 10 mg/kg to about 38 mg/kg, about 10 mg/kg to about 36 mg/kg, about 10 mg/kg to about 34 mg/kg, about 10 mg/kg to about 32 mg/kg, about 10 mg/kg to about 30 mg/kg, about 10 mg/kg to about 28 mg/kg, about 10 mg/kg to about 26 mg/kg, about 10 mg/kg to about 24 mg/kg, about 10 mg/kg to about 22 mg/kg, about 10 mg/kg to about 20 mg/kg, about 10 mg/kg to about 18 mg/kg, about 10 mg/kg to about 16 mg/kg, about 10 mg/kg to about 14 mg/kg, about 10 mg/kg to about 12 mg/kg, about 12 mg/kg to about 50 mg/kg, about 12 mg/kg to about 48 mg/kg, about 12 mg/kg to about 46 mg/kg, about 12 mg/kg to about 44 mg/kg, about 12 mg/kg to about 42 mg/kg, about 12 mg/kg to about 40 mg/kg, about 12 mg/kg to about 38 mg/kg, about 12 mg/kg to about 36 mg/kg, about 12 mg/kg to about 34 mg/kg, about 12 mg/kg to about 32 mg/kg, about 12 mg/kg to about 30 mg/kg, about 12 mg/kg to about 28 mg/kg, about 12 mg/kg to about 26 mg/kg, about 12 mg/kg to about 24 mg/kg, about 12 mg/kg to about 22 mg/kg, about 12 mg/kg to about 20 mg/kg, about 12 mg/kg to about 18 mg/kg, about 12 mg/kg to about 16 mg/kg, about 12 mg/kg to about 14 mg/kg, about 14 mg/kg to about 50 mg/kg, about 14 mg/kg to about 48 mg/kg, about 14 mg/kg to about 46 mg/kg, about 14 mg/kg to about 44 mg/kg, about 14 mg/kg to about 42 mg/kg, about 14 mg/kg to about 40 mg/kg, about 14 mg/kg to about 38 mg/kg, about 14 mg/kg to about 36 mg/kg, about 14 mg/kg to about 34 mg/kg, about 14 mg/kg to about 32 mg/kg, about 14 mg/kg to about 30 mg/kg, about 14 mg/kg to about 28 mg/kg, about 14 mg/kg to about 26 mg/kg, about 14 mg/kg to about 24 mg/kg, about 14 mg/kg to about 22 mg/kg, about 14 mg/kg to about 20 mg/kg, about 14 mg/kg to about 18 mg/kg, about 14 mg/kg to about 16 mg/kg, about 16 mg/kg to about 50 mg/kg, about 16 mg/kg to about 48 mg/kg, about 16 mg/kg to about 46 mg/kg, about 16 mg/kg to about 44 mg/kg, about 16 mg/kg to about 42 mg/kg, about 16 mg/kg to about 40 mg/kg, about 16 mg/kg to about 38 mg/kg, about 16 mg/kg to about 36 mg/kg, about 16 mg/kg to about 34 mg/kg, about 16 mg/kg to about 32 mg/kg, about 16 mg/kg to about 30 mg/kg, about 16 mg/kg to about 28 mg/kg, about 16 mg/kg to about 26 mg/kg, about 16 mg/kg to about 24 mg/kg, about 16 mg/kg to about 22 mg/kg, about 16 mg/kg to about 20 mg/kg, about 16 mg/kg to about 18 mg/kg, about 18 mg/kg to about 50 mg/kg, about 18 mg/kg to about 48 mg/kg, about 18 mg/kg to about 46 mg/kg, about 18 mg/kg to about 44 mg/kg, about 18 mg/kg to about 42 mg/kg, about 18 mg/kg to about 40 mg/kg, about 18 mg/kg to about 38 mg/kg, about 18 mg/kg to about 36 mg/kg, about 18 mg/kg to about 34 mg/kg, about 18 mg/kg to about 32 mg/kg, about 18 mg/kg to about 30 mg/kg, about 18 mg/kg to about 28 mg/kg, about 18 mg/kg to about 26 mg/kg, about 18 mg/kg to about 24 mg/kg, about 18 mg/kg to about 22 mg/kg, about 18 mg/kg to about 20 mg/kg, about 20 mg/kg to about 50 mg/kg, about 20 mg/kg to about 48 mg/kg, about 20 mg/kg to about 46 mg/kg, about 20 mg/kg to about 44 mg/kg, about 20 mg/kg to about 42 mg/kg, about 20 mg/kg to about 40 mg/kg, about 20 mg/kg to about 38 mg/kg, about 20 mg/kg to about 36 mg/kg, about 20 mg/kg to about 34 mg/kg, about 20 mg/kg to about 32 mg/kg, about 20 mg/kg to about 30 mg/kg, about 20 mg/kg to about 28 mg/kg, about 20 mg/kg to about 26 mg/kg, about 20 mg/kg to about 24 mg/kg, about 20 mg/kg to about 22 mg/kg, about 22 mg/kg to about 50 mg/kg, about 22 mg/kg to about 48 mg/kg, about 22 mg/kg to about 46 mg/kg, about 22 mg/kg to about 44 mg/kg, about 22 mg/kg to about 42 mg/kg, about 22 mg/kg to about 40 mg/kg, about 22 mg/kg to about 38 mg/kg, about 22 mg/kg to about 36 mg/kg, about 22 mg/kg to about 34 mg/kg, about 22 mg/kg to about 32 mg/kg, about 22 mg/kg to about 30 mg/kg, about 22 mg/kg to about 28 mg/kg, about 22 mg/kg to about 26 mg/kg, about 22 mg/kg to about 24 mg/kg, about 24 mg/kg to about 50 mg/kg, about 24 mg/kg to about 48 mg/kg, about 24 mg/kg to about 46 mg/kg, about 24 mg/kg to about 44 mg/kg, about 24 mg/kg to about 42 mg/kg, about 24 mg/kg to about 40 mg/kg, about 24 mg/kg to about 38 mg/kg, about 24 mg/kg to about 36 mg/kg, about 24 mg/kg to about 34 mg/kg, about 24 mg/kg to about 32 mg/kg, about 24 mg/kg to about 30 mg/kg, about 24 mg/kg to about 28 mg/kg, about 24 mg/kg to about 26 mg/kg, about 26 mg/kg to about 50 mg/kg, about 26 mg/kg to about 48 mg/kg, about 26 mg/kg to about 46 mg/kg, about 26 mg/kg to about 44 mg/kg, about 26 mg/kg to about 42 mg/kg, about 26 mg/kg to about 40 mg/kg, about 26 mg/kg to about 38 mg/kg, about 26 mg/kg to about 36 mg/kg, about 26 mg/kg to about 34 mg/kg, about 26 mg/kg to about 32 mg/kg, about 26 mg/kg to about 30 mg/kg, about 26 mg/kg to about 28 mg/kg, about 28 mg/kg to about 50 mg/kg, about 28 mg/kg to about 48 mg/kg, about 28 mg/kg to about 46 mg/kg, about 28 mg/kg to about 44 mg/kg, about 28 mg/kg to about 42 mg/kg, about 28 mg/kg to about 40 mg/kg, about 28 mg/kg to about 38 mg/kg, about 28 mg/kg to about 36 mg/kg, about 28 mg/kg to about 34 mg/kg, about 28 mg/kg to about 32 mg/kg, about 28 mg/kg to about 30 mg/kg, about 30 mg/kg to about 50 mg/kg, about 30 mg/kg to about 48 mg/kg, about 30 mg/kg to about 46 mg/kg, about 30 mg/kg to about 44 mg/kg, about 30 mg/kg to about 42 mg/kg, about 30 mg/kg to about 40 mg/kg, about 30 mg/kg to about 38 mg/kg, about 30 mg/kg to about 36 mg/kg, about 30 mg/kg to about 34 mg/kg, about 30 mg/kg to about 32 mg/kg, about 32 mg/kg to about 50 mg/kg, about 32 mg/kg to about 48 mg/kg, about 32 mg/kg to about 46 mg/kg, about 32 mg/kg to about 44 mg/kg, about 32 mg/kg to about 42 mg/kg, about 32 mg/kg to about 40 mg/kg, about 32 mg/kg to about 38 mg/kg, about 32 mg/kg to about 36 mg/kg, about 32 mg/kg to about 34 mg/kg, about 34 mg/kg to about 50 mg/kg, about 34 mg/kg to about 48 mg/kg, about 34 mg/kg to about 46 mg/kg, about 34 mg/kg to about 44 mg/kg, about 34 mg/kg to about 42 mg/kg, about 34 mg/kg to about 40 mg/kg, about 34 mg/kg to about 38 mg/kg, about 34 mg/kg to about 36 mg/kg, about 36 mg/kg to about 50 mg/kg, about 36 mg/kg to about 48 mg/kg, about 36 mg/kg to about 46 mg/kg, about 36 mg/kg to about 44 mg/kg, about 36 mg/kg to about 42 mg/kg, about 36 mg/kg to about 40 mg/kg, about 36 mg/kg to about 38 mg/kg, about 38 mg/kg to about 50 mg/kg, about 38 mg/kg to about 48 mg/kg, about 38 mg/kg to about 46 mg/kg, about 38 mg/kg to about 44 mg/kg, about 38 mg/kg to about 42 mg/kg, about 38 mg/kg to about 40 mg/kg, about 40 mg/kg to about 50 mg/kg, about 40 mg/kg to about 48 mg/kg, about 40 mg/kg to about 46 mg/kg, about 40 mg/kg to about 44 mg/kg, about 40 mg/kg to about 42 mg/kg, about 42 mg/kg to about 50 mg/kg, about 42 mg/kg to about 48 mg/kg, about 42 mg/kg to about 46 mg/kg, about 42 mg/kg to about 44 mg/kg, about 44 mg/kg to about 50 mg/kg, about 44 mg/kg to about 48 mg/kg, about 44 mg/kg to about 46 mg/kg, about 46 mg/kg to about 50 mg/kg, about 46 mg/kg to about 48 mg/kg, or about 46 mg/kg to about 50 mg/kg)

In some embodiments, the methods described herein include administering to a subject about 10 mg/kg to about 400 mg/kg of body weight of sodium phenylbutyrate per day (e.g., about 10 mg/kg to about 380 mg/kg, about 10 mg/kg to about 360 mg/kg, about 10 mg/kg to about 340 mg/kg, about 10 mg/kg to about 320 mg/kg, about 10 mg/kg to about 300 mg/kg, about 10 mg/kg to about 280 mg/kg, about 10 mg/kg to about 260 mg/kg, about 10 mg/kg to about 240 mg/kg, about 10 mg/kg to about 220 mg/kg, about 10 mg/kg to about 200 mg/kg, about 10 mg/kg to about 180 mg/kg, about 10 mg/kg to about 160 mg/kg, about 10 mg/kg to about 140 mg/kg, about 10 mg/kg to about 120 mg/kg, about 10 mg/kg to about 100 mg/kg, about 10 mg/kg to about 80 mg/kg, about 10 mg/kg to about 60 mg/kg, about 10 mg/kg to about 40 mg/kg, about 10 mg/kg to about 20 mg/kg, about 20 mg/kg to about 400 mg/kg, about 20 mg/kg to about 380 mg/kg, about 20 mg/kg to about 360 mg/kg, about 20 mg/kg to about 340 mg/kg, about 20 mg/kg to about 320 mg/kg, about 20 mg/kg to about 300 mg/kg, about 20 mg/kg to about 280 mg/kg, about 20 mg/kg to about 260 mg/kg, about 20 mg/kg to about 240 mg/kg, about 20 mg/kg to about 220 mg/kg, about 20 mg/kg to about 200 mg/kg, about 20 mg/kg to about 180 mg/kg, about 20 mg/kg to about 160 mg/kg, about 20 mg/kg to about 140 mg/kg, about 20 mg/kg to about 120 mg/kg, about 20 mg/kg to about 100 mg/kg, about 20 mg/kg to about 80 mg/kg, about 20 mg/kg to about 60 mg/kg, about 20 mg/kg to about 40 mg/kg, about 40 mg/kg to about 400 mg/kg, about 40 mg/kg to about 380 mg/kg, about 40 mg/kg to about 360 mg/kg, about 40 mg/kg to about 340 mg/kg, about 40 mg/kg to about 320 mg/kg, about 40 mg/kg to about 300 mg/kg, about 40 mg/kg to about 280 mg/kg, about 40 mg/kg to about 260 mg/kg, about 40 mg/kg to about 240 mg/kg, about 40 mg/kg to about 220 mg/kg, about 40 mg/kg to about 200 mg/kg, about 40 mg/kg to about 180 mg/kg, about 40 mg/kg to about 160 mg/kg, about 40 mg/kg to about 140 mg/kg, about 40 mg/kg to about 120 mg/kg, about 40 mg/kg to about 100 mg/kg, about 40 mg/kg to about 80 mg/kg, about 40 mg/kg to about 60 mg/kg, about 60 mg/kg to about 400 mg/kg, about 60 mg/kg to about 380 mg/kg, about 60 mg/kg to about 360 mg/kg, about 60 mg/kg to about 340 mg/kg, about 60 mg/kg to about 320 mg/kg, about 60 mg/kg to about 300 mg/kg, about 60 mg/kg to about 280 mg/kg, about 60 mg/kg to about 260 mg/kg, about 60 mg/kg to about 240 mg/kg, about 60 mg/kg to about 220 mg/kg, about 60 mg/kg to about 200 mg/kg, about 60 mg/kg to about 180 mg/kg, about 60 mg/kg to about 160 mg/kg, about 60 mg/kg to about 140 mg/kg, about 60 mg/kg to about 120 mg/kg, about 60 mg/kg to about 100 mg/kg, about 60 mg/kg to about 80 mg/kg, about 80 mg/kg to about 400 mg/kg, about 80 mg/kg to about 380 mg/kg, about 80 mg/kg to about 360 mg/kg, about 80 mg/kg to about 340 mg/kg, about 80 mg/kg to about 320 mg/kg, about 80 mg/kg to about 300 mg/kg, about 80 mg/kg to about 280 mg/kg, about 80 mg/kg to about 260 mg/kg, about 80 mg/kg to about 240 mg/kg, about 80 mg/kg to about 220 mg/kg, about 80 mg/kg to about 200 mg/kg, about 80 mg/kg to about 180 mg/kg, about 80 mg/kg to about 160 mg/kg, about 80 mg/kg to about 140 mg/kg, about 80 mg/kg to about 120 mg/kg, about 80 mg/kg to about 100 mg/kg, about 100 mg/kg to about 400 mg/kg, about 100 mg/kg to about 380 mg/kg, about 100 mg/kg to about 360 mg/kg, about 100 mg/kg to about 340 mg/kg, about 100 mg/kg to about 320 mg/kg, about 100 mg/kg to about 300 mg/kg, about 100 mg/kg to about 280 mg/kg, about 100 mg/kg to about 260 mg/kg, about 100 mg/kg to about 240 mg/kg, about 100 mg/kg to about 220 mg/kg, about 100 mg/kg to about 200 mg/kg, about 100 mg/kg to about 180 mg/kg, about 100 mg/kg to about 160 mg/kg, about 100 mg/kg to about 140 mg/kg, about 100 mg/kg to about 120 mg/kg, about 120 mg/kg to about 400 mg/kg, about 120 mg/kg to about 380 mg/kg, about 120 mg/kg to about 360 mg/kg, about 120 mg/kg to about 340 mg/kg, about 120 mg/kg to about 320 mg/kg, about 120 mg/kg to about 300 mg/kg, about 120 mg/kg to about 280 mg/kg, about 120 mg/kg to about 260 mg/kg, about 120 mg/kg to about 240 mg/kg, about 120 mg/kg to about 220 mg/kg, about 120 mg/kg to about 200 mg/kg, about 120 mg/kg to about 180 mg/kg, about 120 mg/kg to about 160 mg/kg, about 120 mg/kg to about 140 mg/kg, about 140 mg/kg to about 400 mg/kg, about 140 mg/kg to about 380 mg/kg, about 140 mg/kg to about 360 mg/kg, about 140 mg/kg to about 340 mg/kg, about 140 mg/kg to about 320 mg/kg, about 140 mg/kg to about 300 mg/kg, about 140 mg/kg to about 280 mg/kg, about 140 mg/kg to about 260 mg/kg, about 140 mg/kg to about 240 mg/kg, about 140 mg/kg to about 220 mg/kg, about 140 mg/kg to about 200 mg/kg, about 140 mg/kg to about 180 mg/kg, about 140 mg/kg to about 160 mg/kg, about 160 mg/kg to about 400 mg/kg, about 160 mg/kg to about 380 mg/kg, about 160 mg/kg to about 360 mg/kg, about 160 mg/kg to about 340 mg/kg, about 160 mg/kg to about 320 mg/kg, about 160 mg/kg to about 300 mg/kg, about 160 mg/kg to about 280 mg/kg, about 160 mg/kg to about 260 mg/kg, about 160 mg/kg to about 240 mg/kg, about 160 mg/kg to about 220 mg/kg, about 160 mg/kg to about 200 mg/kg, about 160 mg/kg to about 180 mg/kg, about 180 mg/kg to about 400 mg/kg, about 180 mg/kg to about 380 mg/kg, about 180 mg/kg to about 360 mg/kg, about 180 mg/kg to about 340 mg/kg, about 180 mg/kg to about 320 mg/kg, about 180 mg/kg to about 300 mg/kg, about 180 mg/kg to about 280 mg/kg, about 180 mg/kg to about 260 mg/kg, about 180 mg/kg to about 240 mg/kg, about 180 mg/kg to about 220 mg/kg, about 180 mg/kg to about 200 mg/kg, about 200 mg/kg to about 400 mg/kg, about 200 mg/kg to about 380 mg/kg, about 200 mg/kg to about 360 mg/kg, about 200 mg/kg to about 340 mg/kg, about 200 mg/kg to about 320 mg/kg, about 200 mg/kg to about 300 mg/kg, about 200 mg/kg to about 280 mg/kg, about 200 mg/kg to about 260 mg/kg, about 200 mg/kg to about 240 mg/kg, about 200 mg/kg to about 220 mg/kg, about 220 mg/kg to about 400 mg/kg, about 220 mg/kg to about 380 mg/kg, about 220 mg/kg to about 360 mg/kg, about 220 mg/kg to about 340 mg/kg, about 220 mg/kg to about 320 mg/kg, about 220 mg/kg to about 300 mg/kg, about 220 mg/kg to about 280 mg/kg, about 220 mg/kg to about 260 mg/kg, about 220 mg/kg to about 240 mg/kg, about 240 mg/kg to about 400 mg/kg, about 240 mg/kg to about 380 mg/kg, about 240 mg/kg to about 360 mg/kg, about 240 mg/kg to about 340 mg/kg, about 240 mg/kg to about 320 mg/kg, about 240 mg/kg to about 300 mg/kg, about 240 mg/kg to about 280 mg/kg, about 240 mg/kg to about 260 mg/kg, about 260 mg/kg to about 400 mg/kg, about 260 mg/kg to about 380 mg/kg, about 260 mg/kg to about 360 mg/kg, about 260 mg/kg to about 340 mg/kg, about 260 mg/kg to about 320 mg/kg, about 260 mg/kg to about 300 mg/kg, about 260 mg/kg to about 280 mg/kg, about 280 mg/kg to about 400 mg/kg, about 280 mg/kg to about 380 mg/kg, about 280 mg/kg to about 360 mg/kg, about 280 mg/kg to about 340 mg/kg, about 280 mg/kg to about 320 mg/kg, about 280 mg/kg to about 300 mg/kg, about 300 mg/kg to about 400 mg/kg, about 300 mg/kg to about 380 mg/kg, about 300 mg/kg to about 360 mg/kg, about 300 mg/kg to about 340 mg/kg, about 300 mg/kg to about 320 mg/kg, about 320 mg/kg to about 400 mg/kg, about 320 mg/kg to about 380 mg/kg, about 320 mg/kg to about 360 mg/kg, about 320 mg/kg to about 340 mg/kg, about 340 mg/kg to about 400 mg/kg, about 340 mg/kg to about 380 mg/kg, about 340 mg/kg to about 360 mg/kg, about 360 mg/kg to about 400 mg/kg, about 360 mg/kg to about 380 mg/kg, or about 380 mg/kg to about 400 mg/kg)

In some embodiments, TURSO is administered in an amount of about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, or about 70 mg/kg of body weight per day. In some embodiments, sodium phenylbutyrate is administered in an amount of about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 120 mg/kg, about 140 mg/kg, about 160 mg/kg, about 180 mg/kg, about 200 mg/kg, about 220 mg/kg, about 240 mg/kg, about 260 mg/kg, about 280 mg/kg, about 300 mg/kg, about 320 mg/kg, about 340 mg/kg, about 360 mg/kg, about 380 mg/kg, or about 400 mg/kg of body weight per day.

The methods described herein can be used for treating or ameliorating at least one symptom of ALS in a subject, slowing ALS disease progression, increasing survival time of a subject having one or more symptoms of ALS, preventing or reducing at least one adverse events (e.g., serious adverse events) associated with ALS or its treatment, and reducing the deterioration of, maintaining or improving muscle strength, respiratory muscle/pulmonary function and/or fine motor skill. The methods can also be used for prophylactically treating a subject at risk for developing ALS (e.g., a subject with a family history of ALS) or suspected to be developing ALS (e.g., a subject displaying at least one symptom of ALS, a symptom of upper motor neuron degeneration, and/or a symptom of lower motor neuron degeneration, but not enough symptoms at that time to support a full diagnosis of ALS). The methods are useful for ameliorating at least one symptom of lower motor neuron degeneration or upper motor neuron degeneration.

The methods disclosed herein are also useful for preventing or reducing constipation (e.g., constipation associated with ALS), and ameliorating at least one symptom of benign fasciculation syndrome or cramp fasciculation syndrome.

As disclosed herein, the methods can be used for treating a subject diagnosed with ALS, at risk for developing ALS, or suspected as having ALS. The subject may, for example, have been diagnosed with ALS for 24 months or less (e.g., any of the subranges within this range described herein). For example, the subject may have been diagnosed with ALS for 1 week or less, or on the same day that the presently disclosed treatments are administered. The subject may have shown one or more symptoms of ALS for 24 months or less (e.g., any of the subranges within this range described herein), have an ALS disease progression rate ($\Delta$FS) of about 0.50 or greater (e.g., any of the subranges within this range described herein), have an ALSFRS-R score of 40 or less (e.g., any of the subranges within this range described herein), have lost on average about 0.8 to about 2 ALSFRS-R points per month (e.g. any of the subranges within this range described herein) over the previous 3-12 months, have a mutation in one or more genes selected from the group consisting of: SOD1, $C_9$ORF72, ANG, TARDBP, VCP, VAPB, SQSTM1, DCTN1, FUS, UNC13A, ATXN2, HNRNPA1, CHCHD10, MOBP, $C_{21}$ORF2, NEK1, TUBA4A, TBK1, MATR3, PFN1, UBQLN2, TAF15, OPTN, and TDP-43, and/or have a CSF or blood level of pNF-H of about 300 pg/mL or higher (e.g., about 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 3000, 3200, 3500, 3800, or 4000 pg/mL or higher). In some embodiments, the serum pNF-H level of subjects in the methods described herein can be about 70 to about 1200 pg/mL (e.g., about 70 to about 1000, about 70 to about 800, about 80 to about 600, or about 90 to about 400 pg/mL). In some embodiments, the CSF pNF-H levels of subjects in the methods described herein can be about 1000 to about 5000 pg/mL (e.g., about 1500 to about 4000, or about 2000 to about 3000 pg/mL). The subject may have a CSF or blood level of NfL of about 50 pg/mL or higher (e.g., about 60, 70, 80, 90, 100, 110, 120, 130, 140, 150, 160, 170, 180, 190, 200, 210, 220, 230, 240, or 250 pg/mL or higher). In some embodiments, the serum NfL level of subjects in the methods described herein can be about 50 to about 300 pg/mL (e.g., any of the subranges within this range described herein). In some embodiments, the CSF NfL level of subjects in the methods described herein can be about 2000 to about 40,000 pg/mL (e.g., any of the subranges within this range described herein).

Methods described in the present disclosure can include treatment of ALS per se, as well as treatment for one or more symptoms of ALS. "Treating" ALS does not require 100% abolition of the disease or disease symptoms in the subject. Any relief or reduction in the severity of symptoms or features of the disease is contemplated. "Treating" ALS also refers to a delay in onset of symptoms (e.g., in prophylaxis treatment) or delay in progression of symptoms or the loss of function associated with the disease. "Treating" ALS also refers to eliminating or reducing one or more side effects of a treatment (e.g. those caused by any of the therapeutic agents for treating ALS disclosed herein or known in the art). "Treating" ALS also refers to eliminating or reducing one or more direct or indirect effects of ALS disease progression, such as an increase in the number of falls, lacerations, or GI issues. The subject may not exhibit signs of ALS but may be at risk for ALS. For instance, the subject may carry mutations in genes associated with ALS, have family history of having ALS, or have elevated biomarker levels suggesting a risk of developing ALS. The subject may exhibit early signs of the disease or display symptoms of established or progressive disease. The disclosure contemplates any degree of delay in the onset of symptoms, alleviation of one or more symptoms of the disease, or delay in the progression of any one or more disease symptoms (e.g., any improvement as measured by ALSFRS-R, or maintenance of an ALSFRS-R rating (signaling delayed disease progression)). Any relief or reduction in the severity of symptoms or features of benign fasciculation syndrome and cramp-fasciculation syndrome are also contemplated herein.

The treatment provided in the present disclosure can be initiated at any stage during disease progression. For example, treatment can be initiated prior to onset (e.g., for subjects at risk for developing ALS), at symptom onset or immediately following detection of ALS symptoms, upon observation of any one or more symptoms (e.g., muscle weakness, muscle fasciculations, and/or muscle cramping) that would lead a skilled practitioner to suspect that the subject may be developing ALS. Treatment can also be initiated at later stages. For example, treatment may be initiated at progressive stages of the disease, e.g., when muscle weakness and atrophy spread to different parts of the body and the subject has increasing problems with moving. At or prior to treatment initiation, the subject may suffer from tight and stiff muscles (spasticity), from exaggerated reflexes (hyperreflexia), from muscle weakness and atrophy, from muscle cramps, and/or from fleeting twitches of muscles that can be seen under the skin (fasciculations), difficulty swallowing (dysphagia), speaking or forming words (dysarthria).

Treatment methods can include a single administration, multiple administrations, and repeating administration as required for the prophylaxis or treatment of ALS, or at least one symptom of ALS. The duration of prophylaxis treatment can be a single dosage or the treatment may continue (e.g., multiple dosages), e.g., for years or indefinitely for the lifespan of the subject. For example, a subject at risk for ALS may be treated with the methods provided herein for days, weeks, months, or even years so as to prevent the disease from occurring or fulminating. In some embodiments treatment methods can include assessing a level of disease in the subject prior to treatment, during treatment, and/or after treatment. The treatment provided herein can be administered one or more times daily, or it can be administered weekly or monthly. In some embodiments, treatment can continue until a decrease in the level of disease in the subject is detected. The methods provided herein may in some embodiments begin to show efficacy (e.g., alleviating one or more symptoms of ALS, improvement as measured by the ALSFRS-R, or maintenance of an ALSFRS-R rating) less than 60 days (e.g., less than 50, 45, 40, 35, 30, 25, 20, 15, or 10 days) after the initial administration, or after less than 60 administrations (e.g., less than 50, 45, 40, 35, 30, 25, 20, 15, or 10 administrations).

The terms "administer", "administering", or "administration" as used herein refers to administering drugs described herein to a subject using any art-known method, e.g., ingesting, injecting, implanting, absorbing, or inhaling, the drug, regardless of form. In some embodiments, one or more of the compounds disclosed herein can be administered to a subject by ingestion orally and/or topically (e.g., nasally). For example, the methods herein include administration of an effective amount of compound or compound composition to achieve the desired or stated effect. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Following administration of the bile acid or a pharmaceutically acceptable salt thereof and the phenylbutyrate compound, the subject can be evaluated to detect, assess, or determine their level of ALS disease. In some embodiments, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this disclosure may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

IV. Symptom and Outcome Measurements

This disclosure further provides methods of evaluating ALS symptoms, monitoring ALS progression and evaluating the subject's response to the treatment methods. Non-limiting examples include physical evaluation by a physician, weight, Electrocardiogram (ECG), ALS Functional Rating Scale (ALSFRS or ALSFRS-R) score, respiratory function, muscle strength, cognitive/behavioral function, quality of life, and speech analysis.

Respiratory function of the subject can be measured by e.g. vital capacity (including forced vital capacity and slow vital capacity), maximum mid-expiratory flow rate (MMERF), forced vital capacity (FVC), and forced expiratory volume in 1 second (FEV1). Muscle strength can be evaluated by e.g. hand held dynamometry (HHD), hand grip strength dynamometry, manual muscle testing (MMT), electrical impedance myography (EIM), Maximum Voluntary Isometric Contraction Testing (MVICT), motor unit number estimation (MUNE), Accurate Test of Limb Isometric Strength (ATLIS), or a combination thereof. Cognitive/behavior function can be evaluated by e.g. the ALS Depression Inventory (ADI-12), the Beck Depression Inventory (BDI), and the Hospital Anxiety Depression Scale (HADS) questionnaires. Quality of life can be evaluated by e.g. the ALS Assessment Questionnaire (ALSAQ-40). The Akt level, Akt phosphorylation and/or pAktdAkt ratio can also be used to evaluate a subject's disease progression and response to treatment (See e.g., WO2012/160563).

The levels of biomarkers in the subject's CSF or blood samples are useful indicators of the subject's ALS progression and responsiveness to the methods of treatment provided herein. Biomarkers such as but not limited to, phosphorylated neurofilament heavy chain (pNF-H), neurofilament medium chain, neurofilament light chain (NFL), S10013, cystatin C, chitotriosidase, CRP, TDP-43, uric acid, and certain micro RNAs, can be analyzed for this purpose. Urinalysis can also be used for assessing the subject's response to treatment. Levels of biomarkers such as but not limited to p75ECD and ketones in the urine sample can be analyzed. Levels of creatinine can be measured in the urine and blood samples. In some embodiments, the methods provided herein result in increased or decreased ketone levels in the subject's urine sample. Medical imaging, including but not limited to MM and PET imaging of markers such as Translocator protein (TSPO), may also be utilized.

Muscle Strength

The muscle strength of a subject can be evaluated using known methods in the art. Quantitative strength measures generally demonstrate a linear, predictable strength loss within an ALS patient. Tufts Quantitative Neuromuscular Examination (TQNE) can be used to provide quantitative measurements using a fixed strain gauge. TQNE measures isometric strength of 20 muscle groups and produces interval strength data in both strong and weak muscles (See e.g., Andres et al., Neurology 36:937-941, 1986). Hand-held dynamometry (HHD) tests isometric strength of specific muscles in the arms and legs and produces interval level data (See e.g., Shefne JM, Neurotherapeutics 14:154-160, 2017).

Accurate Test of Limb Isometric Strength (ATLIS) can be used to measure both strong and weak muscle groups using a fixed, wireless load cell (See e.g., Andres et al., Muscle Nerve 56(4):710-715, 2017). Force in twelve muscle groups are evaluated in an ATLIS testing, which reflect the subject's strength in the lower limbs, upper limbs, as well as the subject's grip strength. In some embodiments, ATLIS testing detects changes in muscle strength before any change in function is observed.

The methods provided herein may improve, maintain, or slow down the deterioration of a subject's muscle strength (e.g., lower limb strength, upper limb strength, or grip strength), as evaluated by any suitable methods described herein. The methods may result in improvement of the subject's upper limb strength more significantly than other muscle groups. For example, the effect on muscle strength can be reflected in one or more muscle groups selected from quadriceps, biceps, hamstrings, triceps, and anterior tibialis.

Muscle strength can be assessed by HHD, hand grip strength dynamometry, MMT, EIM, MVICT, MUNE, ATLIS, or a combination thereof, before, during and/or after the administration of a bile acid or a pharmaceutically acceptable salt thereof and a phenylbutyrate compound.

In some embodiments, the muscle strength is assessed by ATLIS. The total ATLIS score as well as the upper extremity and lower extremity ATLIS scores can be assessed. The methods of the present disclosure can result in a rate of decline in the total ATLIS score of a subject of about 3.50 PPN/month or less (e.g., about 3.45, 3.40, 3.35, 3.30, 3.25, 3.20, 3.15, 3.10, 3.05, 3.00 PPN/month or less). The methods of the present disclosure can also results in a reduction of the mean rate of decline in the total ATLIS score of a subject by at least about 0.2 PPN/month (e.g., at least about 0.25, 0.30, 0.35, 0.40, 0.45, or 0.50 PPN/month) as compared to a control subject not receiving the administration. The mean rate of decline in the upper extremity ATLIS score of a subject can be reduced by at least about 0.50 PPN/month (e.g., at least about 0.55, 0.60, 0.65, 0.70, 0.75, 0.80, 0.85, or 0.90 PPN/month) as compared to a control subject not receiving the administration described herein. The mean rate of decline in the lower extremity ATLIS score of a subject can be reduced by at least about 0.20 PPN/month (e.g., at least about 0.25, 0.30, 0.35, 0.40, 0.45, 0.50, 0.55, or 0.60 PPN/month) as compared to a control subject not receiving the administration described herein. In some embodiments, improvement or maintenance of the subject's muscle strength may begin to occur less than 60 days (e.g., less than 55, 50, 45, 40, 30, 25, or 20 days) following the initial administration. PPN represents the percentage of predicted normal strength based on age, sex weight and height.

Pulmonary Function

ALS is a progressive neurodegenerative disease that ultimately leads to respiratory failure and death. Pulmonary function tests, such as vital capacity (VC), maximum mid-expiratory flow rate (MMERF), forced vital capacity (FVC), slow vital capacity (SVC), and forced expiratory volume in 1 second (FEV1), can be used to monitor ALS progression and/or the subject's response to treatment. On average, the rate of respiratory function decline of an ALS patient measured by Vital Capacity (VC) can be about 2.24% of predicted (±6.9) per month. In some embodiments, measures from pulmonary function tests are associated with survival (See e.g., Moufavi et al. Iran J Neurol 13(3): 131-137, 2014). Additional measures, such as maximal inspiratory and expiratory pressures, arterial blood gas measurements, and overnight oximetry, may provide earlier evidence of dysfunction. Comparison of vital capacity in the upright and supine positions may also provide an earlier indication of weakening ventilatory muscle strength.

The methods provided herein may improve or maintain the subject's respiratory muscle and/or pulmonary function, or slow down the deterioration of the subject's respiratory muscle and/or pulmonary function. A subject's respiratory muscle and/or pulmonary function can be evaluated by any of the suitable methods described herein or otherwise known in the art. In some embodiments, the respiratory muscle function of a human subject is assessed based on the subject's SVC. In some embodiments of any of the methods of improving, maintaining, or slowing down the deterioration of respiratory muscle function in a human subject described herein, the treatment results in a mean rate of decline in the SVC of the subject of about 3.50 PPN/month or less (e.g., about 3.45, 3.40, 3.35, 3.30, 3.25, 3.20, 3.15, 3.10, 3.05, or 3.00 PPN/month or less). In some embodiments, the treatment reduces the mean rate of decline in the SVC of the subject by at least about 0.5 PPN/month (e.g., at least about 0.55, 0.60, 0.65, 0.70, 0.75, 0.80, 0.85, 0.90, 0.95, or 1.00 PPN/month) as compared to a control subject not receiving the treatment. In some embodiments, improvement or maintenance of the subject's pulmonary function may begin to occur less than 60 days (e.g., less than 55, 50, 45, 40, 30, 25, or 20 days) following the initial administration. In some embodiments, the subject's pulmonary function progresses less than expected after fewer than 60 days following the initial administration.

Adverse Events

Subjects treated with any of the methods provided herein may present fewer adverse events (e.g., any of the adverse events disclosed herein), or present one or more of the adverse events to a lesser degree than control subjects not receiving the treatment. Exemplary adverse events include gastrointestinal related adverse events (e.g., abdominal pain, gastritis, nausea and vomiting, constipation, rectal bleeding, peptic ulcer disease, and pancreatitis); hematologic adverse events (e.g., aplastic anemia and ecchymosis); cardiovascular adverse events (e.g., arrhythmia and edema); renal adverse events (e.g., renal tubular acidosis); psychiatric adverse events (e.g., depression); skin adverse events (e.g., rash); and miscellaneous adverse events (e.g., syncope and weight gain). In some embodiments, the methods provided herein do not result in, or result in minimal symptoms of, constipation, neck pain, headache, falling, dry mouth, muscular weakness, falls, laceration, and Alanine Aminotransferase (ALT) increase. In some embodiments, the adverse events are serious adverse events, such as but not limited to respiratory adverse events, falls, or lacerations.

In some embodiments, administration of the combination of a bile acid and a phenylbutyrate compound can result in fewer adverse events (e.g., any of the adverse events disclosed herein), or less severe adverse events compared to administration of the bile acid or the phenylbutyrate compound alone.

The average survival time for an ALS patient may vary. The median survival time can be about 30 to about 32 months from symptom onset, or about 14 to about 20 months from diagnosis. The survival time of subjects with bulbar-onset ALS can be about 6 months to about 84 months from symptom onset, with a median of about 27 months. The methods provided herein may in some embodiments increase survival for a subject having ALS by at least one month (e.g., at least 2, 3, 4, 5, 6, 7, 8, 9, 10, 11, 12, 13, 14, 15, 16, 17, 18, 19, 20, 21, 22, 23, 24, 28, 32, 36, 40, 50, 60, 70, 80, or 90 months). Methods provided herein may in some embodiments delay the onset of ventilator-dependency or tracheostomy by at least one month (e.g., at least 2, 3, 4, 5, 6, 7, 8, 9, 10, 11, 12, 13, 14, 15, 16, 17, 18, 19, 20, 21, 22, 23, 24, 28, 32, 36, 40, 50, 60, 70, 80, or 90 months).

Methods provided herein may reduce disease progression rate wherein the average ALSFRS-R points lost per month by the subject is reduced by at least about 0.2 (e.g., at least about 0.25, 0.30, 0.35, 0.40, 0.45, 0.50, 0.55, 0.60, 0.65, 0.70, 0.75, 0.80, 0.85, 0.90, 0.95, 1.0, 1.05, 1.1, 1.15, 1.2, 1.25, 1.3, 1.35, 1.4, 1.45 or 1.5) as compared to a control subject not receiving the treatment. The methods provided herein may slow down the progression in one or more categories evaluated by the ALSFRS scale, including: speech, salivation, swallowing, handwriting, Cutting Food and Handling Utensils, Dressing and Hygiene, Turning in Bed and Adjusting Bed Clothes, Walking, Climbing Stairs, Dyspnea, Orthopnea, Respiratory Insufficiency. In some embodiments, the methods provided herein improve or slow down deterioration of a subject's fine motor function, as evaluated by one or more categories of the ALSFRS-R scale (e.g., handwriting, cutting food and handling utensils, or dressing and hygiene).

In some embodiments, the methods provided herein are more effective in treating subjects that are about 18 to about 50 years old (e.g., about 18 to about 45, about 18 to about 40, about 18 to about 35, about 18 to about 30, about 18 to about 25, or about 18 to about 22 years old), as compared to subjects 50 years or older (e.g., 55, 60, 65, 70, 75, or 80 years or older). In some embodiments, the methods provided herein are more effective in treating subjects who have been diagnosed with ALS and/or who showed ALS symptom onset less than about 24 months (e.g., less than about 22, 20, 18, 16, 14, 12, 10, 8, 6, 4, 2, or 1 month), as compared to subjects who has been diagnosed with ALS and/or who showed ALS symptom onset more than about 24 months (e.g., more than about 26, 28, 30, 32, 34, 36, 40, 45, 50, 55, or 60 months). In some embodiments, the methods provided herein are more effective in treating subjects who have been diagnosed with ALS and/or who showed ALS symptom onset more than about 24 months (e.g., more than about 26, 28, 30, 32, 34, 36, 40, 45, 50, 55, or 60 months), as compared to subjects who has been diagnosed with ALS and/or who showed ALS symptom less than about 24 months (e.g., less than about 22, 20, 18, 16, 14, 12, 10, 8, 6, 4, 2, or 1 month).

In some embodiments, responsiveness to the methods of treatment provided herein are gender-dependent. The methods provided herein can be more or less effective in treating female subjects as compared to male subjects. For instance, female subjects may show improvements (e.g., as measured by the ALSFRS-R or any other outcome measures described herein) earlier or later than male subjects when treated at similar stages of disease progression. Female subjects may in some embodiments show bigger or smaller improvements (e.g., as measured by the ALSFRS-R or any other outcome measures described herein) than male subjects when treated at similar stages of disease progression. The pharmacokinetics of the bile acid and the phenylbutyrate compound may be the same or different in female and male subjects.

V. Additional Therapeutic Agents

The methods described herein can further include administering to the subject one or more additional therapeutic agents, e.g. in amounts effective for treating or achieving a modulation of at least one symptom of ALS. Any known ALS therapeutic agents known in the art can be used as an additional therapeutic agent. Exemplary therapeutic agents include riluzole ($C_8H_5F_3N_2OS$, e.g. sold under the trade names Rilutek® and Tiglutik®), edaravone (e.g. sold under the trade names Radicava® and Radicut®), dextromethorphan, anticholinergic medications, and psychiatric medications (e.g. antidepressants, antipsychotics, anxiolytics/hypnotics, mood stabilizers, and stimulants).

Neudexta® is a combination of dextromethorphan and quinidine, and can be used for the treatment of pseudobulbar affect (inappropriate laughing or crying). Anticholinergic medications and antidepressants can be used for treating excessive salivation. Exemplary anticholinergic medications include glycopyrrolate, scopolamine, atropine (Atropen), belladonna alkaloids, benztropine mesylate (Cogentin), clidinium, cyclopentolate (Cyclogyl), darifenacin (Enablex), dicylomine, fesoterodine (Toviaz), flavoxate (Urispas), glycopyrrolate, homatropine hydrobromide, hyoscyamine (Levsinex), ipratropium (Atrovent), orphenadrine, oxybutynin (Ditropan XL), propantheline (Pro-banthine), scopolamine, methscopolamine, solifenacin (VESlcare), tiotropium (Spiriva), tolterodine (Detrol), trihexyphenidyl, trospium, and diphenhydramine (Benadryl). Exemplary antidepressants include selective serotonin inhibitors, serotonin-norepinephrine reuptake inhibitors, serotonin modulators and stimulators, serotonin antagonists and reuptake inhibitors, norepinephrine reuptake inhibitors, norepinephrine-dopamine reuptake inhibitors, tricyclic antidepressants, tetracyclic antidepressants, monoamine oxidase inhibitors, and NMDA receptor antagonists.

The additional therapeutic agent(s) can be administered for a period of time before administering the initial dose of a composition comprising a bile acid or a pharmaceutically acceptable salt thereof (e.g., TURSO) and a phenylbutyrate compound (e.g., sodium phenylbutyrate), and/or for a period of time after administering the final dose of the composition.

In some embodiments, a subject in the methods described herein has been previously treated with one or more additional therapeutic agents (e.g., any of the additional therapeutic agents described herein, such as riluzole and edavarone). In some embodiments, the subject has been administered a stable dose of the therapeutic agent(s) (e.g., riluzole and/or edaravone) for at least 30 days (e.g., at least 40 days, 50 days, 60 days, 90 days, or 120 days) prior to administering the composition of the present disclosure. The absorption, metabolism, and/or excretion of the additional therapeutic agent(s) may be affected by the bile acid or a pharmaceutically acceptable salt thereof and/or the phenylbutyrate compound. For instance, co-administration of sodium phenylbutyrate with riluzole, or edavarone, may increase the subject's exposure to riluzole or edavarone. Co-administering riluzole with the bile acid or a pharmaceutically acceptable salt thereof and the phenylbutyrate compound can improve riluzole tolerance by the subject as compared to administering riluzole alone.

The combination of a bile acid or a pharmaceutically acceptable salt thereof, a phenylbutyrate compound, and one or more additional therapeutic agents can have a synergistic effect in treating ALS. Smaller doses of the additional therapeutic agents may be required to obtain the same pharmacological effect, when administered in combination with a bile acid or a pharmaceutically acceptable salt thereof, and a phenylbutyrate compound. In some embodiments, the amount of the additional therapeutic agent(s) administered in combination with a bile acid or a pharmaceutically acceptable salt thereof and a phenylbutyrate compound can be reduced by at least about 10% (e.g., at least about 15%, 20%, 25%, 30%, 35%, 40%, 45%, 50%, or 55%) compared to the dosage amount used when the additional therapeutic agent(s) is administered alone. Additionally or alternatively, the methods of the present disclosure can reduce the required frequency of administration of other therapeutic agents (e.g., other ALS therapeutic agents) to obtain the same pharmacological effect.

The bile acid or a pharmaceutically acceptable salt thereof and the phenylbutyrate compound can be administered shortly after a meal (e.g., within two hours of a meal) or under fasting conditions. The subject may have consumed food items (e.g., solid foods or liquid foods) less than 2 hours before administration of a bile acid or a pharmaceutically acceptable salt thereof and/or a phenylbutyrate compound; or will consume food items less than 2 hours after administration of one or both of the compounds. Food items may affect the rate and extent of absorption of the bile acid or a pharmaceutically acceptable salt thereof and/or the phenylbutyrate compound. For instance, food can change the bioavailability of the compounds by delaying gastric emptying, stimulating bile flow, changing gastrointestinal pH, increasing splanchnic blood flow, changing luminal metabolism of the substance, or physically or chemically interacting with a dosage form or the substance. The nutrient and caloric contents of the meal, the meal volume, and the meal temperature can cause physiological changes in the GI tract in a way that affects drug transit time, luminal dissolution, drug permeability, and systemic availability. In general, meals that are high in total calories and fat content are more likely to affect the GI physiology and thereby result in a larger effect on the bioavailability of a drug. The methods provided herein can further include administering to the subject a plurality of food items, for example, less than 2 hours (e.g., less than 1.5 hour, 1 hour, or 0.5 hour) before or after administering the bile acid or a pharmaceutically acceptable salt thereof, and/or the phenylbutyrate compound.

EXAMPLES

Additional embodiments are disclosed in further detail in the following examples, which are provided by way of illustration and are not in any way intended to limit the scope of this disclosure or the claims.

The purpose of Examples 1 to 6 was to evaluate human drug transporter interactions with six test articles as a substrate and/or an inhibitor for the efflux transporter Bile Salt Export Pump (B SEP).

The criteria used to judge if a test article was a substrate of efflux transporters were an efflux ratio of >2 and >50% inhibition by known inhibitor. The criteria used to judge if a test article was an inhibitor of efflux transporters were inhibition of the probe substrate net efflux activity by >25%; the inhibition should exhibit concentration dependence by the test article. If inhibition is observed, half maximal inhibitory concentration ($IC_{50}$) values were estimated based on the doses used for each test article. The drug-drug interaction (DDI) potential for each test article was calculated using the appropriate R value equation from the FDA guidance (Food and Drug Administration, 2020).

Materials and Methods

The following Materials and Methods were used for Examples 1 to 6.

Vesicular Uptake Procedure

Membrane vesicles prepared from baculovirus-infected insect cells (Sf9) expressing BSEP proteins were obtained from Genomembrane (Thermo Fisher Scientific, Waltham, Massachusetts).

The BSEP-transfected Sf9 membrane vesicles were thawed and placed on wet ice prior to use. Assay uptake buffer and membrane vesicles were combined, as appropriate, with the appropriate substrate ($^3$H-taurocholic acid, TCA), inhibitor (cyclosporine A), or test article solution, and the mixtures were added to the appropriate wells of a 96-well filter plate (50 µg/well). The plate and adenosine triphosphate (ATP) and adenosine monophosphate (AMP) solutions were pre-incubated at 37° C. for 5 minutes. The reaction was initiated by the addition of ATP to the appropriate wells of the plate; AMP was added to the negative control wells to a final concentration of 5 mM each. The plate was incubated at 37° C. for 30 minutes. The reaction was terminated by the addition of chilled wash buffer, and the plate was maintained on wet ice until filtration. Chilled blocking buffer was added to a filter plate, and positive pressure was applied. The filter plate was then washed with ice-cold wash buffer, the incubation media was transferred to the pre-treated filter plate, and gentle positive pressure was applied. The filter plate was washed four times with chilled wash buffer, ethanol was added to the filter plate, and the samples were eluted into a deep-well 96-well plate at ambient temperature for 10 minutes. Vesicles were extracted from filter plates for LC-MS quantitation. Samples were stored at −20° C. until analysis, as applicable.

Assessment of Test Article as a Substrate of BSEP

Adenosine triphosphate (ATP)-dependent uptake of the test article (at concentrations shown in Table 1, below) by the transporter was conducted according to the vesicular uptake procedure, in the presence of vehicle or known inhibitor.

TABLE 1

| Test Article Concentrations (µM) | Test Article Concentrations (µM) |
|---|---|
| Sodium phenylbutyrate | 1 and 10 |
| Phenylacetic acid | 1 and 10 |
| Phenylacetyl-L-glutamine | 1 and 10 |
| Tauroursodeoxycholic acid | 1 and 10 |
| Ursodeoxycholic acid | 1 and 10 |
| Glycoursodeoxycholic acid | 1 and 10 |

Uptake of a probe substrate in the presence or absence of a known inhibitor was included as controls. Probe substrate and selective inhibitor information is summarized in Table 2, below.

TABLE 2

| Efflux Transporter Substrates and Inhibitors | | |
|---|---|---|
| Transporter | Probe Substrate (µM) | Selective Inhibitor (µM) |
| BSEP | $^3$H-Taurocholic acid (1) | Cyclosporine A (20) |

Assessment of Test Article as an Inhibitor of BSEP

Uptake of a radiolabeled probe substrate by the transporter was conducted in the presence of a) vehicle, b) selective inhibitor, and c) test article (at concentrations shown in Table 3, below) according to the vesicular uptake procedure. Probe substrate and selective inhibitor information is summarized in Table 2.

TABLE 3

| Test Article Concentrations (µM) | Test Article Concentrations (µM) |
|---|---|
| Sodium phenylbutyrate | 25 and 250 |
| Phenylacetic acid | 750 and 7500 |
| Phenylacetyl-L-glutamine | 50 and 500 |
| Tauroursodeoxycholic acid | 5 and 50 |
| Ursodeoxycholic acid | 50 and 500 |
| Glycoursodeoxycholic acid | 10 and 100 |

Sample Identification

Samples were uniquely identified by a tube/well number or plate position that was cross-referenced to study number, transporter, incubation time, test article/substrate/inhibitor concentration, and donor/receiver, as applicable.

Calculations

Efflux Transporters (Membrane Vesicle Assays: Vesicular Uptake)

Rate of Uptake Activity $$\text{Rate of Uptake Activity}(p\text{mol/min/mg}) = \frac{\text{Amount}_{ves}}{\text{Time} \times \text{Protein}}$$

where:

$\text{Amount}_{ves}$ Amount of substrate or test article in vesicles in each well (pmol)

Time Incubation time (minutes)

Protein Total protein in each well (mg)

A TP-Dependent Uptake Activity $$\text{ATP-Dependent Uptake Activity} = \text{Uptake}_{ATP} - \text{Uptake}_{AMP}$$

Signal to Noise Ratio (SNR)

$$SNR = \frac{Uptake_{ATP}}{Uptake_{AMP}}$$

where:
Uptake$_{ATP}$ Uptake in the presence of ATP (pmol/min/mg)
Uptake$_{AMP}$ Uptake in the presence of AMP (pmol/min/mg)
Inhibition of Uptake $$\text{Percent Remaining Uptake} = \frac{Uptake_{+inh}}{Uptake_{-inh}} \times 100$$

where:
Uptake+inh ATP-dependent uptake of substrate or test article in presence of inhibitor, or ATP-dependent uptake of substrate in the presence of test article (pmol/min/mg)
Uptake-inh ATP-dependent uptake of substrate or test article only (pmol/min/mg)

Data Analysis

Statistical analyses were limited to descriptive statistics such as mean, standard deviation, relative standard deviation, and regression analysis, where appropriate.

Data Acceptance Criteria

The membrane vesicle efflux system was considered fully functional as the fold ATP-dependent uptake over vehicle or vector control was ≥4 and selective inhibitors demonstrated >50% inhibition of probe substrate uptake.

A test article was identified as a substrate if there was a ≥2-fold ATP-dependent uptake over vehicle control and >50% inhibition by selective inhibitor. A test article was identified as an inhibitor if there was a >25% inhibition of probe substrate uptake.

Example 1— Assessment of Sodium Phenylbutyrate as a Substrate and/or Inhibitor of BSEP Experiments were conducted to assess whether sodium phenylbutyrate is a substrate and/or inhibitor of BSEP. Sodium phenylbutyrate dosed at 1 and 10 μM was not detected in uptake samples, indicating sodium phenylbutyrate was not a substrate of B SEP. Sodium phenylbutyrate (25 and 250 μM) was not an inhibitor of B SEP.

Solubility, Stability, and Non-Specific Binding of Sodium Phenylbutyrate

Solubility

The test article, sodium phenylbutyrate, was soluble up to 50,000 μM in methanol and to 250 μM in assay buffers, with a final 0.5% methanol content (v:v) at all concentrations tested.

Stability

Stability of 25 and 250 μM sodium phenylbutyrate was determined in glass vials before and after freezing once, and after freezing and thawing aliquots in an assay plate three times. The test article was tested in transport buffer alone or with 0.002% PS-80 or 1% HSA to assess recovery. The data are presented in Table 4, below. In transport buffer alone, recovery of sodium phenylbutyrate after the single freeze or after three freeze-thaw cycles was ≥98.9%. In buffer containing 0.002% PS-80, recovery of sodium phenylbutyrate was ≥91.6% after the single freeze and ≥95.3% after three freeze-thaw cycles. In transport buffer containing 1% HSA, recovery of sodium phenylbutyrate was ≥90.5% after the single freeze and ≥94.8% after three freeze-thaw cycles.

TABLE 4

Stability of sodium phenylbutyrate in HBSS with 10 mM HEPES, pH 7.4, with or without excipients, after freezing in glass vials or after 3 freeze-thaw cycles in assay plates

| | | | Percent Recovery[a] | |
|---|---|---|---|---|
| | Sodium phenylbutyrate (μM) | | Glass Vials 1 freeze-thaw | Assay Plates[b] 3 freeze-thaw cycles |
| Buffer | Nominal | Actual[a] | | |
| sHBSS | 25 | 21.4 | 102 | 105 |
| sHBSS | 250 | 223 | 98.9 | 99.4 |
| sHBSS + PS-80 | 25 | 22.4 | 105 | 100 |
| sHBSS + PS-80 | 250 | 244 | 91.6 | 95.3 |
| sHBSS + HSA | 25 | 22.0 | 103 | 103 |
| sHBSS + HSA | 250 | 222 | 90.5 | 94.8 |

HBSS Hank's Balanced Salt Solution.
HEPES N-(2-hydroxyethyl)piperazine-N'-(2-ethanesulfonic acid).
HSA 1% human serum albumin.
PS-80 0.002% polysorbate-80.
sHBSS HBSS with 10 mM HEPES, pH 7.4.
[a]Average of two replicates, unless otherwise noted.
[b]Mean of three replicates.

Non-Specific Binding

Non-specific binding of sodium phenylbutyrate to the transwell assay plate in the absence of cells was also evaluated. Sodium phenylbutyrate solutions (25 and 250 μM) were placed in the apical (250 μL) or basolateral (700 μL) chambers (donor chambers) of a transwell plate in triplicate wells, with matching blank buffer in the opposite receiver chambers, and were incubated at 37° C. for 2 hours. Data are presented in Table 5, below. In transport buffer alone, the recovery was ≥107% in the apical to basolateral direction and ≥82.8% in the basolateral to apical direction. In transport buffer containing 0.002% PS-80, the recovery was ≥110% in the apical-to-basolateral direction and ≥86.9% in the basolateral to apical direction. In transport buffer containing 1% HSA, the recovery was ≥107% in the apical to basolateral direction and ≥92.8% in the basolateral to apical direction. The stability and non-specific binding results were similar, with acceptable recovery from all buffer systems tested. Other test articles exhibited best recovery in transport buffer containing 0.002% PS-80; as such, this buffer was also used for sodium phenylbutyrate assay conditions.

TABLE 5

Recovery of sodium phenylbutyrate after incubation in a transwell plate in the absence of Caco-2 cells at 37° C. for 2 hours

| | | Percent Recovery | | | |
|---|---|---|---|---|---|
| | | A to B | | B to A | |
| Buffer | Treatment | Mean[a] | SD | Mean[a] | SD |
| sHBSS | SP (25 μM) | 129 | 1.98 | 95.3 | 2.38 |
| sHBSS | SP (250 μM) | 107 | 1.80 | 82.8 | 5.69 |
| sHBSS + PS-80 | SP (25 μM) | 120 | 5.08 | 92.6 | 0.930 |
| sHBSS + PS-80 | SP (250 μM) | 110 | 1.98 | 86.9 | 2.12 |

TABLE 5-continued

Recovery of sodium phenylbutyrate after incubation in a transwell plate in the absence of Caco-2 cells at 37° C. for 2 hours

| Buffer | Treatment | Percent Recovery | | | |
|---|---|---|---|---|---|
| | | A to B | | B to A | |
| | | Mean[a] | SD | Mean[a] | SD |
| sHBSS + HSA | SP (25 μM) | 120 | 1.26 | 96.9 | 0.962 |
| sHBSS + HSA | SP (250 μM) | 107 | 4.65 | 92.8 | 2.41 |

A to B Apical to basolateral direction.
B to A Basolateral to apical direction.
HSA 1% human serum albumin.
PS-80 0.002% polysorbate-80.
SD Standard deviation.
sHBSS HBSS with 10 mM HEPES, pH 7.4.
SP Sodium phenylbutyrate.
[a]Mean of three replicates.

Assessment of Sodium Phenylbutyrate as a Substrate and Inhibitor of BSEP (Using Membrane Vesicles)

The ATP-dependent uptake of sodium phenylbutyrate (1 and 10 μM) in BSEP-transfected Sf9 membrane vesicles, was tested alone or with the BSEP inhibitor cyclosporine A (20 μM), and the data are presented in Table 6, below. Sodium phenylbutyrate, dosed at 1 and 10 μM, was not detected in the experimental samples, indicating no uptake had occurred. Sodium phenylbutyrate was not a substrate of BSEP.

TABLE 6

ATP-dependent uptake of sodium phenylbutyrate by BSEP membrane vesicles

| Treatment | Sample | Uptake Activity (pmol/minute/mg protein) | Signal-to-Noise Ratio | | ATP-Dependent Uptake Activity (pmol/minute/mg protein) | |
|---|---|---|---|---|---|---|
| | | Mean[a] | Mean[a] | SD | Mean[a] | SD |
| SP (1 μM) | Mg-ATP | BLQ | NA | NA | NA | NA |
| | Mg-AMP | BLQ | | | | |
| SP (10 μM) + Cyclosporine (20 μM) | Mg-ATP | BLQ | NA | NA | NA | NA |
| | Mg-AMP | BLQ | | | | |
| SP (1 μM) | Mg-ATP | BLQ | NA | NA | NA | NA |
| | Mg-AMP | BLQ | | | | |
| SP (10 μM) + Cyclosporine (20 μM) | Mg-ATP | BLQ | NA | NA | NA | NA |
| | Mg-AMP | BLQ | | | | |

BLQ Below the limit of quantitation (0.1 μM).
Mg-AMP Magnesium-adenosine 5'-monophosphate.
Mg-ATP Magnesium-adenosine 5'-triphosphate.
NA Not applicable.
SD Standard deviation.
SP Sodium phenylbutyrate.
[a]Mean of three replicates.

The ATP-dependent uptake of BSEP substrate $^3$H-taurocholic acid (TCA) in BSEP vesicles, alone or with cyclosporine A (20 μM) or sodium phenylbutyrate (25 and 250 μM), is presented in Table 7, below. Mean ATP-dependent uptake activity for $^3$H-taurocholic acid was 25.0 pmol/minute/mg protein, with a signal-to-noise ratio of 41.9. The $^3$H-TCA uptake decreased to 2.85% in the presence of BSEP inhibitor cyclosporine A. Sodium phenylbutyrate slightly inhibited $^3$H-TCA uptake, with 77.2% activity remaining at 25 μM, but the inhibition was not concentration dependent and did not meet the criteria for identification as an inhibitor.

TABLE 7

ATP-dependent uptake of $^3$H-taurocholic acid by BSEP membrane vesicles
in the absence and presence of sodium phenylbutyrate and selective inhibitor

| Treatment | Sample | Uptake Activity (pmol/minute/mg protein) Mean[a] | Signal-to-Noise Ratio Mean[a] | SD | ATP-Dependent Uptake Activity (pmol/minute/mg protein) Mean[a] | SD | Percent of Control |
|---|---|---|---|---|---|---|---|
| Control | Mg-ATP | 25.6 | 41.9 | 8.50 | 25.0 | 5.21 | 100 |
|  | Mg-AMP | 0.613 |  |  |  |  |  |
| Cyclosporine A | Mg-ATP | 1.25 | 2.32 | 0.753 | 0.713 | 0.407 | 2.85 |
| (20 µM) | Mg-AMP | 0.540 |  |  |  |  |  |
| SP (25 µM) | Mg-ATP | 19.9 | 35.9 | 7.30 | 19.3 | 4.04 | 77.2 |
|  | Mg-AMP | 0.554 |  |  |  |  |  |
| SP (250 µM) | Mg-ATP | 21.3 | 31.6 | 3.29 | 20.6 | 2.22 | 82.4 |
|  | Mg-AMP | 0.673 |  |  |  |  |  |

Mg-AMP Magnesium-adenosine 5'-monophosphate.
Mg-ATP Magnesium-adenosine 5'-triphosphate.
SD Standard deviation.
SP Sodium phenylbutyrate.
[a]Mean of three replicates.

Example 2—Assessment of Phenylacetic Acid as a Substrate and/or Inhibitor of BSEP Experiments were conducted to assess whether phenylacetic acid is a substrate and/or inhibitor of BSEP. Adenosine triphosphate (ATP)-dependent BSEP uptake activity for phenylacetic acid at 1 and 10 µM was observed >2-fold of the adenosine monophosphate (AMP) uptake, but was not inhibited by cyclosporine A, suggesting phenylacetic acid was not a substrate of B SEP. Phenylacetic acid (750 and 7500 µM) strongly inhibited the probe substrate uptake by BSEP at 7500 µM, with an estimated $IC_{50}$<7500 µM.

Solubility, Stability, and Non-Specific Binding of Phenylacetic Acid

Solubility

The test article phenylacetic acid was soluble up to 1500 mM in methanol and to 7500 in assay buffers, with a final 0.5% methanol content (v:v) at all concentrations tested.

Stability

Stability of 250 and 2500 µM phenylacetic acid was determined in glass vials before and after freezing once, and after freezing and thawing aliquots in an assay plate three times. The test article was tested in transport buffer alone or with 0.002% PS-80 or 1% HSA to assess recovery. The data are presented in Table 8, below. In transport buffer alone, recovery of phenylacetic acid after the single freeze or after three freeze-thaw cycles was ≥90.8%. In buffer containing 0.002% PS-80, recovery of phenylacetic acid was at 96.1 and 54.7% at 250 and 2500 respectively, after the single freeze, and 77.9 and 57.7%, respectively, after three freeze-thaw cycles. The recovery was acceptable in this buffer at concentrations ≤250 µM. In transport buffer containing 1% HSA, recovery of phenylacetic acid was ≥99.5% after the single freeze, and >26.6% after three freeze-thaw cycles.

TABLE 8

Stability of phenylacetic acid in HBSS with 10 mM HEPES,
pH 7.4, with or without excipients, after freezing in glass vials
or after 3 freeze-thaw cycles in assay plates

| | Phenylacetic acid (µM) | | Percent Recovery[a] Glass Vials 1 freeze-thaw | Assay Plates[b] 3 freeze-thaw cycles |
|---|---|---|---|---|
| Buffer | Nominal | Actual[a] | | |
| sHBSS | 250 | 190 | 114 | 95.1 |
| sHBSS | 2500 | 679 | 90.8 | 99.8 |
| sHBSS + PS-80 | 250 | 230 | 96.1 | 77.9 |
| sHBSS + PS-80 | 2500 | 701 | 54.7 | 57.7 |
| sHBSS + HSA | 250 | 226 | 103 | 60.1 |
| sHBSS + HSA | 2500 | 796 | 99.5 | 26.6 |

HBSS Hank's Balanced Salt Solution.
HEPES N-(2-hydroxyethyl)piperazine-N'-(2-ethanesulfonic acid).
HSA 1% human serum albumin.
PS-80 0.002% polysorbate-80.
sHBSS HBSS with 10 mM HEPES, pH 7.4.
[a]Average of two replicates, unless otherwise noted.
[b]Mean of three replicates Non-Specific Binding Non-specific binding of phenylacetic acid to the transwell assay plate in the absence of cells was not conducted. However, the recovery of the test article (1 and 10 µM) was determined in the Caco-2 efflux assay, in the presence of cells, and was acceptable.

Based on the stability results, transporter assays for phenylacetic acid were conducted in transport buffer containing 0.002% PS-80.

Assessment of Phenylacetic Acid as a Substrate and Inhibitor of BSEP (Using Membrane Vesicles)

The ATP-dependent uptake of phenylacetic acid (1 and 10 µM) in BSEP-transfected Sf9 membrane vesicles was tested alone or with the B SEP inhibitor cyclosporine A (20 µM), and the data are presented in Table 9, below. ATP-dependent uptake of phenylacetic acid at 1 and 10 μM was observed at 24.2 and 814 pmol/minute/mg protein, respectively, with signal-to-noise ratios of 9.95 and 12.6, respectively. However, the activity in the presence of the inhibitor was 75.6 and 94.9% of control at 1 and 10 μM, respectively. The inhibition is not concentration dependent; as such, it is unlikely that phenylacetic acid is a substrate of BSEP.

Example 3—Assessment of Phenylacetyl-L-Glutamine as a Substrate and/or Inhibitor of BSEP Experiments were conducted to assess whether phenylacetyl-L-glutamine is a substrate and/or inhibitor of BSEP. ATP-dependent BSEP uptake activity for phenylacetyl-L-glutamine at 1 and 10 11M was not observed, suggesting

TABLE 9

ATP-dependent uptake of phenylacetic acid by BSEP membrane vesicles

| Treatment | Sample | Uptake Activity (pmol/minute/mg protein) Mean[a] | Signal-to-Noise Ratio Mean[a] | SD | ATP-Dependent Uptake Activity (pmol/minute/mg protein) Mean[a] | SD | Percent of Control |
|---|---|---|---|---|---|---|---|
| PA (1 μM) | Mg-ATP | 26.9 | 9.95 | 1.54 | 24.2 | 4.16 | 100 |
|  | Mg-AMP | 2.71[b] |  |  |  |  |  |
| PA (1 μM) + | Mg-ATP | 25.9 | 3.41 | 0.732 | 18.3 | 5.56 | 75.6 |
| Cyclosporine (20 μM) | Mg-AMP | 7.60[c] |  |  |  |  |  |
| PA (10 μM) | Mg-ATP | 884 | 12.6 | 21.1 | 814 | 1480 | 100 |
|  | Mg-AMP | 70.3 |  |  |  |  |  |
| PA (10 μM) + | Mg-ATP | 857 | 10.1 | 15.8 | 772 | 1340 | 94.9 |
| Cyclosporine (20 μM) | Mg-AMP | 84.7 |  |  |  |  |  |

Mg-AMP Magnesium-adenosine 5'-monophosphate.
Mg-ATP Magnesium-adenosine 5'-triphosphate.
PA Phenylacetic acid.
SD Standard deviation.
[a]Mean of three replicates, unless otherwise noted.
[b]Single replicate.
[c]Average of two replicates.

The ATP-dependent uptake of BSEP substrate $^3$-TCA in BSEP vesicles, alone or with cyclosporine A (20 μM) or phenylacetic acid (750 and 7500 is presented in Table 10, below. Mean ATP-dependent uptake activity for $^3$-TCA was 4.69 pmol/minute/mg protein, with a signal-to-noise ratio of 9.97. The $^3$-TCA uptake decreased to 3.49% in the presence of BSEP inhibitor cyclosporine A. Phenylacetic acid inhibited $^3$-TCA uptake, with 99.6% activity remaining at 750 μM but 0.00% activity remaining at 7500 μM, for an estimated IC50<7500 μM. Phenylacetic acid was, therefore, identified as an inhibitor of BSEP.

phenylacetyl-L-glutamine was not a substrate of BSEP. Phenylacetyl-L-glutamine (50 and 500 μM) was not an inhibitor of BSEP.

Solubility, Stability, and Non-Specific Binding of Phenylacetyl-L-Glutamine

Solubility

The test article, phenylacetyl-L-glutamine, was soluble up to 100,000 μM in DMSO. Stock solutions were further diluted from the DMSO stock with methanol.

TABLE 10

ATP-dependent uptake of $^3$H-taurocholic acid by BSEP membrane vesicles in the absence and presence of phenylacetic acid and selective inhibitor

| Treatment | Sample | Uptake Activity (pmol/minute/mg protein) Mean[a] | Signal-to-Noise Ratio Mean[a] | SD | ATP-Dependent Uptake Activity (pmol/minute/mg protein) Mean[a] | SD | Percent of Control |
|---|---|---|---|---|---|---|---|
| Control | Mg-ATP | 5.21 | 9.97 | 0.683 | 4.69 | 0.357 | 100 |
|  | Mg-AMP | 0.523 |  |  |  |  |  |
| Cyclosporine A | Mg-ATP | 0.419 | 1.64 | 0.727 | 0.164 | 0.186 | 3.49 |
| (20 μM) | Mg-AMP | 0.255 |  |  |  |  |  |
| PA (750 μM) | Mg-ATP | 4.96 | 17.2 | 1.04 | 4.68 | 0.300 | 99.6 |
|  | Mg-AMP | 0.288 |  |  |  |  |  |
| PA (7500 μM) | Mg-ATP | 0.370 | 0.731 | 0.305 | −0.136 | 0.155 | 0.00[b] |
|  | Mg-AMP | 0.506 |  |  |  |  |  |

Mg-AMP Magnesium-adenosine 5'-monophosphate.
Mg-ATP Magnesium-adenosine 5'-triphosphate.
PA Phenylacetic acid.
SD Standard deviation.
[a]Mean of three replicates.
[b]Negative percentage is reported as zero.

Phenylacetyl-L-glutamine was soluble to 500 µM in assay buffers, with a final 0.5% organic content (v:v) at all concentrations tested.

Stability

Stability of 50 and 500 µM phenylacetyl-L-glutamine was determined in glass vials before and after freezing once, and after freezing and thawing aliquots in an assay plate three times. The test article was tested in transport buffer alone or with 0.002% PS-80 or 1% HSA to assess recovery. The data are presented in Table 11, below. In transport buffer alone, recovery of phenylacetyl-L-glutamine after the single freeze or after three freeze-thaw cycles was ≥95.0%. In buffer containing 0.002% PS-80, recovery of phenylacetyl-L-glutamine was ≥96.3% after the single freeze and ≥98.8% after three freeze-thaw cycles. In transport buffer containing 1% HSA, recovery of phenylacetyl-L-glutamine was ≥96.9% after the single freeze and ≥106% after three freeze-thaw cycles.

TABLE 11

Stability of phenylacetyl-L-glutamine in HBSS with 10 mM HEPES, pH 7.4, with or without excipients, after freezing in glass vials or after 3 freeze-thaw cycles in assay plates

| | | | Percent Recovery[a] | |
|---|---|---|---|---|
| | Phenylacetyl-L-glutamine (µM) | | Glass Vials 1 freeze-thaw | Assay Plates[b] 3 freeze-thaw cycles |
| Buffer | Nominal | Actual[a] | | |
| sHBSS | 50 | 45.1 | 95.0 | 101 |
| sHBSS | 500 | 429 | 96.2 | 98.3 |
| sHBSS + PS-80 | 50 | 46.5 | 96.3 | 98.8 |
| sHBSS + PS-80 | 500 | 453 | 98.9 | 100 |
| sHBSS + HSA | 50 | 47.1 | 96.9 | 114 |
| sHBSS + HSA | 500 | 459 | 104 | 106 |

HBSS Hank's Balanced Salt Solution.
HEPES N-(2-hydroxyethyl)piperazine-N'-(2-ethanesulfonic acid).
HSA 1% human serum albumin.
PS-80 0.002% polysorbate-80.
sHBSS HBSS with 10 mM HEPES, pH 7.4.
[a]Average of two replicates, unless otherwise noted.
[b]Mean of three replicates Non-Specific Binding Non-specific binding of phenylacetyl-L-glutamine to the transwell assay plate in the absence of cells was also evaluated. Phenylacetyl-L-glutamine solutions (50 and 500 µM) were placed in the apical (250 µL) or basolateral (700 µL) chambers (donor chambers) of a transwell plate in triplicate wells, with matching blank buffer in the receiver chambers, and were incubated at 37° C. for 2 hours. Data are presented in Table 12, below. In transport buffer alone, the recovery was ≥107% in the apical to basolateral direction and ≥103% in the basolateral to apical direction. In transport buffer containing 0.002% PS-80, the recovery was ≥105% in the apical to basolateral direction and ≥98.6% in the basolateral to apical direction. In transport buffer containing 1% HSA, the recovery was ≥106% in the apical to basolateral direction and ≥99.4% in the basolateral to apical direction.

TABLE 12

Recovery of phenylacetyl-L-glutamine after incubation in a transwell plate in the absence of Caco-2 cells at 37° C. for 2 hours

| | | Percent Recovery | | | |
|---|---|---|---|---|---|
| | | A to B | | B to A | |
| Buffer | Treatment | Mean[a] | SD | Mean[a] | SD |
| sHBSS | PG (50 µM) | 107 | 1.62 | 104 | 1.89 |
| sHBSS | PG (500 µM) | 110 | 1.19 | 103 | 2.05 |
| sHBSS + PS-80 | PG (50 µM) | 105 | 1.22 | 98.6 | 1.54 |
| sHBSS + PS-80 | PG (500 µM) | 108 | 3.17 | 101 | 0.0649 |
| sHBSS + HSA | PG (50 µM) | 106 | 0.619 | 99.4 | 3.09 |
| sHBSS + HSA | PG (500 µM) | 115 | 2.00 | 105 | 4.95 |

A to B Apical to basolateral direction.
B to A Basolateral to apical direction.
HSA 1% human serum albumin.
PG Phenylacetyl-L-glutamine.
PS-80 0.002% polysorbate-80.
SD Standard deviation.
sHBSS HBSS with 10 mM HEPES, pH 7.4.
[a]Mean of three replicates The stability and non-specific binding results were similar with acceptable recovery from all buffer systems tested. Other test articles exhibited best recovery in transport buffer containing 0.002% PS-80; as such, this buffer was also used for phenylacetyl-L-glutamine assay conditions.

Assessment of Phenylacetyl-L-Glutamine as a Substrate and Inhibitor of BSEP (Using Membrane Vesicles)

The ATP-dependent uptake of phenylacetyl-L-glutamine (1 and 10 µM) in BSEP-transfected Sf9 membrane vesicles, was tested alone or with the BSEP inhibitor cyclosporine A (20 and the data are presented in Table 13, below. No ATP-dependent uptake activity for phenylacetyl-L-glutamine at 1 and 10 µM was observed. These data indicated phenylacetyl-L-glutamine was not a substrate of BSEP.

TABLE 13

ATP-dependent uptake of phenylacetyl-L-glutamine by BSEP membrane vesicles

| | | Uptake Activity (pmol/minute/ mg protein) | Signal-to-Noise Ratio | | ATP-Dependent Uptake Activity (pmol/minute/mg protein) | |
|---|---|---|---|---|---|---|
| Treatment | Sample | Mean[a] | Mean[a] | SD | Mean[a] | SD |
| PG (1 µM) | Mg-ATP | 56.8[b] | 0.686 | NA | 0.00[c] | NA |
| | Mg-AMP | 82.7[b] | | | | |
| PG (1 µM) + Cyclosporine (20 µM) | Mg-ATP | BLQ | NA | NA | NA | NA |
| | Mg-AMP | BLQ | | | | |
| PG (10 µM) | Mg-ATP | BLQ | NA | NA | NA | NA |
| | Mg-AMP | BLQ | | | | |

TABLE 13-continued

ATP-dependent uptake of phenylacetyl-L-glutamine by BSEP membrane vesicles

| Treatment | Sample | Uptake Activity (pmol/minute/ mg protein) Mean[a] | Signal-to-Noise Ratio Mean[a] | SD | ATP-Dependent Uptake Activity (pmol/minute/mg protein) Mean[a] | SD |
|---|---|---|---|---|---|---|
| PG (10 µM) + Cyclosporine (20 µM) | Mg-ATP Mg-AMP | 27.9[b] BLQ | NA | NA | NA | NA |

BLQ Below the limit of quantitation.
Mg-AMP Magnesium-adenosine 5'-monophosphate.
Mg-ATP Magnesium-adenosine 5'-triphosphate.
NA Not applicable.
PG Phenylacetyl-L-glutamine.
SD Standard deviation.
[a]Mean of three replicates, unless otherwise noted.
[b]Single replicate.
[c]Negative values are reported as 0.00.

The ATP-dependent uptake of BSEP substrate $^3$-TCA in BSEP vesicles, alone or with cyclosporine A (20 µM) or phenylacetyl-L-glutamine (50 and 500 is presented in Table 14, below. Mean ATP-dependent uptake activity for $^3$-TCA was 15.4 pmol/minute/mg protein, with a signal-to-noise ratio of 25.5. The $^3$-TCA uptake decreased to 2.09% in the presence of BSEP inhibitor cyclosporine A. Phenylacetyl-L-glutamine did not inhibit $^3$-TCA uptake, with 86.4% activity remaining at 500 µM.

TABLE 14

ATP-dependent uptake of $^3$H-taurocholic acid by BSEP membrane vesicles in the absence and presence of phenylacetyl-L-glutamine and selective inhibitor

| Treatment | Sample | Uptake Activity (pmol/minute/ mg protein) Mean[a] | Signal-to-Noise Ratio Mean[a] | SD | ATP-Dependent Uptake Activity (pmol/minute/mg protein) Mean[a] | SD | Percent of Control |
|---|---|---|---|---|---|---|---|
| Control | Mg-ATP | 16.0 | 25.5 | 3.83 | 15.4 | 2.41 | 100 |
|  | Mg-AMP | 0.630 |  |  |  |  |  |
| Cyclosporine A (20 µM) | Mg-ATP | 0.910 | 1.55 | 0.912 | 0.322 | 0.536 | 2.09 |
|  | Mg-AMP | 0.588 |  |  |  |  |  |
| PG (50 µM) | Mg-ATP | 18.8 | 28.1 | 1.41 | 18.1 | 0.941 | 117 |
|  | Mg-AMP | 0.667 |  |  |  |  |  |
| PG (500 µM) | Mg-ATP | 14.1 | 18.6 | 8.78 | 13.3 | 6.65 | 86.4 |
|  | Mg-AMP | 0.758 |  |  |  |  |  |

Mg-AMP Magnesium-adenosine 5'-monophosphate.
Mg-ATP Magnesium-adenosine 5'-triphosphate.
NA Not applicable.
PG Phenylacetyl-L-glutamine.
SD Standard deviation.
[a]Mean of three replicates.

Example 4—Assessment of Tauroursodeoxycholic Acid as a Substrate and/or Inhibitor of BSEP Experiments were conducted to assess whether Tauroursodeoxycholic Acid is a substrate and/or inhibitor of BSEP. ATP-dependent BSEP uptake activity for tauroursodeoxycholic acid at 1 and 10 µM was >2-fold of the AMP uptake and was inhibited by cyclosporine A, identifying tauroursodeoxycholic acid as a substrate of BSEP. Tauroursodeoxycholic acid (5 and 50 µM) strongly inhibited the probe substrate uptake by BSEP, with an estimated IC50<5 µM.

Solubility, Stability, and Non-Specific Binding of Tauroursodeoxycholic Acid

Solubility

The test article, tauroursodeoxycholic acid, was soluble up to 10,000 µM in methanol and to 50 µM into assay buffers, with a final 0.5% methanol content (v:v) at all concentrations tested.

Stability

Stability of 1 and 10 µM tauroursodeoxycholic acid was determined in glass vials before and after freezing once, and after freezing and thawing aliquots in an assay plate three times. The test article was tested in transport buffer alone or with 0.002% PS-80 or 1% HSA to assess recovery. The data are presented in Table 15, below. In transport buffer alone, recovery of tauroursodeoxycholic acid after the single freeze or after three freeze-thaw cycles was ≥77.7%. In buffer containing 0.002% PS-80, recovery of tauroursodeoxycholic acid was ≥108% after the single freeze and ≥106% after three freeze-thaw cycles. In transport buffer containing 1% HSA, recovery of tauroursodeoxycholic acid was ≥102% after the single freeze and ≥82.7% after three freeze-thaw cycles.

TABLE 15

Stability of tauroursodeoxycholic acid in HBSS with 10 mM HEPES, pH 7.4, with or without excipients, after freezing in glass vials or after 3 freeze-thaw cycles in assay plates

| Buffer | Tauroursodeoxycholic acid (μM) | | Percent Recovery[a] | |
|---|---|---|---|---|
| | Nominal | Actual[a] | Glass Vials 1 freeze-thaw | Assay Plates[b] 3 freeze-thaw cycles |
| sHBSS | 1 | 1.04 | 77.7 | 91.4 |
| sHBSS | 10 | 7.32 | 101 | 103 |
| sHBSS + PS-80 | 1 | 0.967 | 108 | 106 |
| sHBSS + PS-80 | 10 | 9.50 | 108 | 109 |
| sHBSS + HSA | 1 | 1.15 | 107 | 100 |
| sHBSS + HSA | 10 | 12.7 | 102 | 82.7 |

HBSS Hank's Balanced Salt Solution.
HEPES N-(2-hydroxyethyl)piperazine-N'-(2-ethanesulfonic acid).
HSA 1% human serum albumin.
PS-80 0.002% polysorbate-80.
sHBSS HBSS with 10 mM HEPES, pH 7.4.
[a]Average of two replicates, unless otherwise noted.
[b]Mean of three replicates.

Non-Specific Binding

Non-specific binding of tauroursodeoxycholic acid to the transwell assay plate in the absence of cells was also evaluated. Tauroursodeoxycholic acid solutions (1 and 10 μM) were placed in the apical (250 μL) or basolateral (700 μL) chambers (donor chambers) of a transwell plate in triplicate wells, with matching blank buffer in the receiver chambers, and were incubated at 37° C. for 2 hours. Data are presented in Table 16, below. In transport buffer alone, the recovery was ≥112% in the apical to basolateral direction and ≥74.4% in the basolateral to apical direction, suggesting some sticking to plastic in the absence of cells when using buffer with no excipients. In transport buffer containing 0.002% PS-80, the recovery was ≥136% in the apical to basolateral direction and ≥95.3% in the basolateral to apical direction. In transport buffer containing 1% HSA, the recovery was ≥124% in the apical to basolateral direction and ≥69.3% in the basolateral to apical direction.

Based on the stability and non-specific binding results, transporter assays were conducted in transport buffer containing 0.002% PS-80 for best recovery of tauroursodeoxycholic acid under assay conditions.

TABLE 16

Recovery of tauroursodeoxycholic acid after incubation in a transwell plate in the absence of Caco-2 cells at 37° C. for 2 hours

| Buffer | Treatment | A to B | | B to A | |
|---|---|---|---|---|---|
| | | Mean[a] | SD | Mean[a] | SD |
| sHBSS | TA (1 μM) | 112 | 2.44 | 74.4 | 9.21 |
| sHBSS | TA (10 μM) | 238 | 24.5 | 94.9 | 8.10 |
| sHBSS + PS-80 | TA (1 μM) | 136 | 4.29 | 109 | 13.7 |
| sHBSS + PS-80 | TA (10 μM) | 316 | 54.9 | 95.3 | 1.34 |
| sHBSS + HSA | TA (1 μM) | 137 | 2.50 | 84.4[b] | NA |
| sHBSS + HSA | TA (10 μM) | 124 | 9.82 | 69.3 | 1.89 |

A to B Apical to basolateral direction.
B to A Basolateral to apical direction.
HSA 1% human serum albumin.
NA Not applicable.
PS-80 0.002% polysorbate-80.
SD Standard deviation.
sHBSS HBSS with 10 mM HEPES, pH 7.4.
TA Tauroursodeoxycholic acid.
[a]Mean of three replicates.
[b]Single quantifiable replicate Assessment of Tauroursodeoxycholic Acid as a Substrate and Inhibitor of BSEP (Using Membrane Vesicles)

The ATP-dependent uptake of tauroursodeoxycholic acid (1 and 10 μM) in BSEP-transfected Sf9 membrane vesicles was tested alone or with the BSEP inhibitor cyclosporine A (20 μM), and the data are presented in Table 17, below. Mean ATP-dependent uptake activity for tauroursodeoxycholic acid at 1 and 10 μM was 14.4 and 22.4 pmol/minute/mg protein, respectively, with a signal-to-noise ratio of 3.94- and 10.6-fold over the AMP controls, respectively. Cyclosporine A treatment resulted in ≤12.6% remaining BSEP activity. These data indicated tauroursodeoxycholic acid was actively transported and was a substrate of BSEP.

TABLE 17

ATP-dependent uptake of tauroursodeoxycholic acid by BSEP membrane vesicles

| Treatment | Sample | Uptake Activity (pmol/minute/mg protein) Mean[a] | Signal-to-Noise Ratio Mean[a] | SD | ATP-Dependent Uptake Activity (pmol/minute/mg protein) Mean[a] | SD | Percent of Control |
|---|---|---|---|---|---|---|---|
| TA (1 µM) | Mg-ATP | 19.3[b] | 3.94 | NA | 14.4 | 10.5 | 100 |
| | Mg-AMP | 4.90[c] | | | | | |
| TA (1 µM) + Cyclosporine (20 µM) | Mg-ATP | BLQ | NA | NA | NA | NA | NA |
| | Mg-AMP | BLQ | | | | | |
| TA (10 µM) | Mg-ATP | 24.7 | 10.6 | 7.52 | 22.4 | 17.5 | 100 |
| | Mg-AMP | 2.33 | | | | | |
| TA (10 µM) + Cyclosporine (20 µM) | Mg-ATP | 6.79 | 1.71 | 0.168 | 2.81 | 0.670 | 12.6 |
| | Mg-AMP | 3.98 | | | | | |

BLQ Below the limit of quantitation.
Mg-AMP Magnesium-adenosine 5'-monophosphate.
Mg-ATP Magnesium-adenosine 5'-triphosphate.
NA Not applicable.
SD Standard deviation.
TA Tauroursodeoxycholic acid.
[a]Mean of three replicates, unless noted otherwise.
[b]Single replicate.
[c]Mean of two replicates.

The ATP-dependent uptake of BSEP substrate $^3$H-TCA in BSEP vesicles, alone or with cyclosporine A (20 µM) or tauroursodeoxycholic acid (5 and 50 is presented in Table 18, below. Mean ATP-dependent uptake activity for $^3$H-TCA was 14.5 pmol/minute/mg protein, with a signal-to-noise ratio of 28.3. The $^3$H-TCA uptake decreased to 4.88% in the presence of B SEP inhibitor cyclosporine A. Tauroursodeoxycholic acid inhibited $^3$-TCA uptake, with 5.14% activity remaining at 50 µM; an estimated IC$_{50}$ would be <5 µM.

TABLE 18

ATP-dependent uptake of $^3$H-taurocholic acid by BSEP membrane vesicles in the absence and presence of tauroursodeoxycholic acid and selective inhibitor

| Treatment | Sample | Uptake Activity (pmol/minute/mg protein) Mean[a] | Signal-to-Noise Ratio Mean[a] | SD | ATP-Dependent Uptake Activity (pmol/minute/mg protein) Mean[a] | SD | Percent of Control |
|---|---|---|---|---|---|---|---|
| Control | Mg-ATP | 15.1[b] | 28.3[b] | NA | 14.5[b] | NA | 100 |
| | Mg-AMP | 0.531 | | | | | |
| Cyclosporine A (20 µM) | Mg-ATP | 1.17[b] | 2.55[b] | NA | 0.708[b] | NA | 4.88 |
| | Mg-AMP | 0.458 | | | | | |
| TA (5 µM) | Mg-ATP | 7.45[b] | 10.1[b] | NA | 6.71 | NA | 46.2 |
| | Mg-AMP | 0.737 | | | | | |
| TA (50 µM) | Mg-ATP | 1.30 | 2.34 | 0.709 | 0.747 | 0.394 | 5.14 |
| | Mg-AMP | 0.556 | | | | | |

Mg-AMP Magnesium-adenosine 5'-monophosphate.
Mg-ATP Magnesium-adenosine 5'-triphosphate.
NA Not applicable.
SD Standard deviation.
TA Tauroursodeoxycholic acid.
[a]Mean of three replicates, unless noted otherwise.
[b]Mean of two replicates.

Example 5—Assessment of Ursodeoxycholic Acid as a Substrate and/or Inhibitor of BSEP Experiments were conducted to assess whether ursodeoxycholic acid is a substrate and/or inhibitor of BSEP. ATP-dependent BSEP uptake of ursodeoxycholic acid at 1 and 1011M was <2-fold above uptake in the AMP samples, which indicated the test article was not a substrate of BSEP. Ursodeoxycholic acid (50 and 500 µM) inhibited the probe substrate uptake by BSEP, with an estimated IC$_{50<50011}$M.

Solubility, Stability, and Non-Specific Binding of Ursodeoxycholic Acid

Solubility

The test article, ursodeoxycholic acid, was soluble up to 100,000 µM in methanol and to 500 µM in assay buffers, with a final 0.5% methanol content (v:v) at all concentrations tested.

Stability

Stability of 1 and 10 µM ursodeoxycholic acid was determined in glass vials before and after freezing once, and after freezing and thawing aliquots in an assay plate three times. The test article was tested in transport buffer alone or with 0.002% PS-80 or 1% HSA to assess recovery. The data are presented in Table 19, below. In transport buffer alone, recovery of ursodeoxycholic acid after the single freeze or after three freeze-thaw cycles was ≥85.8%. In buffer containing 0.002% PS-80, recovery of ursodeoxycholic acid was 110% after the single freeze and ≥98.4% after three freeze-thaw cycles. In transport buffer containing 1% HSA, recovery of ursodeoxycholic acid was ≥95.0% after the single freeze and ≥89.8% after three freeze-thaw cycles.

TABLE 19

Stability of ursodeoxycholic acid in HBSS with 10 mM HEPES, pH 7.4, with or without excipients, after freezing in glass vials or after 3 freeze-thaw cycles in assay plates

| | Ursodeoxycholic acid (μM) | | Percent Recovery[a] | |
|---|---|---|---|---|
| Buffer | Nominal | Actual[a] | Glass Vials 1 freeze-thaw | Assay Plates[b] 3 freeze-thaw cycles |
| sHBSS | 1 | 1.15 | 96.1 | 85.8 |
| sHBSS | 10 | 10.3 | 92.9 | 95.5 |
| sHBSS + PS-80 | 1 | 0.884 | 110 | 98.4 |
| sHBSS + PS-80 | 10 | 8.45 | 110 | 101 |
| sHBSS + HSA | 1 | 0.935 | 95.0 | 98.6 |
| sHBSS + HSA | 10 | 7.88 | 98.1 | 89.8 |

HBSS Hank's Balanced Salt Solution.
HEPES N-(2-hydroxyethyl)piperazine-N'-(2-ethanesulfonic acid).
HSA 1% human serum albumin.
PS-80 0.002% polysorbate-80.
sHBSS HBSS with 10 mM HEPES, pH 7.4.
[a]Average of two replicates, unless otherwise noted.
[b]Mean of three replicates.

Non-Specific Binding

Non-specific binding of ursodeoxycholic acid to the transwell assay plate in the absence of cells was also evaluated. Ursodeoxycholic acid solutions (1 and 10 μM) were placed in the apical (250 μL) or basolateral (700 μL) chambers (donor chambers) of a transwell plate in triplicate wells, with matching blank buffer in the receiver chambers, and were incubated at 37° C. for 2 hours. Data are presented in Table 20, below. In transport buffer alone, the recovery was ≥118% in the apical to basolateral direction and ≥84.8% in the basolateral to apical direction. In transport buffer containing 0.002% PS-80, the recovery was ≥104% in the apical to basolateral direction and ≥96.9% in the basolateral to apical direction. In transport buffer containing 1% HSA, the recovery was ≥107% in the apical to basolateral direction, but the test article was not detectable in the apical chamber of the basolateral to apical direction.

TABLE 20

Recovery of ursodeoxycholic acid after incubation in a transwell plate in the absence of Caco-2 cells at 37° C. for 2 hours

| | | Percent Recovery | | | |
|---|---|---|---|---|---|
| | | A to B | | B to A | |
| Buffer | Treatment | Mean[a] | SD | Mean[a] | SD |
| sHBSS | UA (1 μM) | 118 | 9.07 | 84.8 | 2.02 |
| sHBSS | UA (10 μM) | 126 | 10.6 | 93.5 | 2.32 |
| sHBSS + PS-80 | UA (1 μM) | 121 | 19.7 | 96.9 | 11.5 |
| sHBSS + PS-80 | UA (10 μM) | 104 | 6.49 | 106 | 11.8 |
| sHBSS + HSA | UA (1 μM) | 107[b] | NA | NA[c] | NA |
| sHBSS + HSA | UA (10 μM) | 117[b] | NA | NA[c] | NA |

A to B Apical to basolateral direction.
B to A Basolateral to apical direction.
HSA 1% human serum albumin.
NA Not applicable.
PS-80 0.002% polysorbate-80.
SD Standard deviation.
sHBSS HBSS with 10 mM HEPES, pH 7.4.
UA Ursodeoxycholic acid.
[a]Mean of three replicates, unless noted otherwise.
[b]Average of two replicates.
[c]Papp value could not be calculated since receiver chamber samples were below the limit of quantitation.

Based on the stability and non-specific binding results, transporter assays were conducted in transport buffer containing 0.002% PS-80 for best recovery of ursodeoxycholic acid under assay conditions.

Assessment of Ursodeoxycholic Acid as a Substrate and Inhibitor of BSEP (Using Membrane Vesicles)

The ATP-dependent uptake of ursodeoxycholic acid (1 and 10 μM) in BSEP-transfected Sf9 membrane vesicles was tested alone or with the BSEP inhibitor cyclosporine A (20 and the data are presented in Table 21, below. Mean ATP-dependent uptake activity for ursodeoxycholic acid could not be detected at 1 μM. The ATP-dependent uptake activity at 10 μM was 0.792 pmol/minute/mg protein from a single replicate, with a signal-to-noise ratio of only 1.26-fold over the AMP controls. These data indicated ursodeoxycholic acid was not a substrate of BSEP.

TABLE 21

ATP-dependent uptake of ursodeoxycholic acid by BSEP membrane vesicles

| Treatment | Sample | Uptake Activity (pmol/minute/mg protein) Mean[a] | Signal-to-Noise Ratio Mean[a] | | ATP-Dependent Uptake Activity (pmol/minute/mg protein) Mean[a] | |
|---|---|---|---|---|---|---|
| | | | | SD | | SD |
| UA (1 μM) | Mg-ATP | BLQ | NA | NA | NA | NA |
| | Mg-AMP | BLQ | | | | |
| UA (1 μM) + Cyclosporine (20 μM) | Mg-ATP | BLQ | NA | NA | NA | NA |
| | Mg-AMP | BLQ | | | | |
| UA (10 μM) | Mg-ATP | 3.87[b] | 1.26[b] | NA | 0.792[b] | NA |
| | Mg-AMP | 3.08[b] | | | | |
| UA (10 μM) + Cyclosporine (20 μM) | Mg-ATP | 5.61[b] | NA | NA | NA | NA |
| | Mg-AMP | BLQ | | | | |

BLQ Below the limit of quantitation.
Mg-AMP Magnesium-adenosine 5'-monophosphate.
Mg-ATP Magnesium-adenosine 5'-triphosphate.
NA Not applicable.
SD Standard deviation.
UA Ursodeoxycholic acid.
[a]Mean of three replicates, unless otherwise noted.
[b]Single replicate The ATP-dependent uptake of BSEP substrate $^3$H-TCA in BSEP vesicles, alone or with cyclosporine A (20 μM) or ursodeoxycholic acid (50 and 500 is presented in Table 22, below. Mean ATP-dependent uptake activity for $^3$H-TCA was 9.43 pmol/minute/mg protein, with a signal-to-noise ratio of 21.0. The $^3$H-TCA uptake decreased to 4.39% in the presence of BSEP inhibitor cyclosporine A. Ursodeoxycholic acid inhibited $^3$-TCA uptake, with 64.0% activity remaining at 50 μM and 4.50% remaining at 500 μM, for an estimated IC50<500 μM.

are presented in Table 23, below. In transport buffer alone, recovery of glycoursodeoxycholic acid after the single freeze or after three freeze-thaw cycles was ≥84.1%. In buffer containing 0.002% PS-80, recovery of glycoursodeoxycholic acid was ≥99.8% after the single freeze and ≥107% after three freeze-thaw cycles. In transport buffer containing 1% HSA, the dose solutions were approximately twice the expected concentration; from these, the recovery of glycoursodeoxycholic acid was ≥94.8% after the single freeze and ≥98.4% after three freeze-thaw cycles.

TABLE 22

ATP-dependent uptake of $^3$H-taurocholic acid by BSEP membrane vesicles in the absence and presence of ursodeoxycholic acid and selective inhibitor

| Treatment | Sample | Uptake Activity (pmol/minute/mg protein) Mean[a] | Signal-to-Noise Ratio Mean[a] | | ATP-Dependent Uptake Activity (pmol/minute/mg protein) Mean[a] | | Percent of Control |
|---|---|---|---|---|---|---|---|
| | | | Mean[a] | SD | Mean[a] | SD | |
| Control | Mg-ATP | 9.90 | 21.0 | 4.15 | 9.43 | 1.95 | 100 |
| | Mg-AMP | 0.470 | | | | | |
| Cyclosporine A (20 μM) | Mg-ATP | 0.820 | 2.02 | 0.434 | 0.414 | 0.176 | 4.39 |
| | Mg-AMP | 0.406 | | | | | |
| UA (50 μM) | Mg-ATP | 6.73 | 9.66 | 0.653 | 6.04 | 0.455 | 64.0 |
| | Mg-AMP | 0.697 | | | | | |
| UA (500 μM) | Mg-ATP | 0.873 | 1.95 | 0.231 | 0.425 | 0.104 | 4.50 |
| | Mg-AMP | 0.449 | | | | | |

Mg-AMP Magnesium-adenosine 5'-monophosphate.
Mg-ATP Magnesium-adenosine 5'-triphosphate.
SD Standard deviation.
UA Ursodeoxycholic acid.
aMean of three replicates

Example 6—Assessment of Glycoursodeoxycholic Acid as a Substrate and/or Inhibitor of BSEP Experiments were conducted to assess whether glycoursodeoxycholic acid as a substrate and/or inhibitor of BSEP. ATP-dependent BSEP uptake activity for glycoursodeoxycholic acid at 1 and 10 μM was >2-fold of the AMP uptake and was inhibited by cyclosporine A, identifying glycoursodeoxycholic acid as a substrate of BSEP. Glycoursodeoxycholic acid (10 and 100 μM) strongly inhibited the probe substrate uptake by BSEP, with an estimated IC50<10 μM.

Solubility, Stability, and Non-Specific Binding of Glycoursodeoxycholic Acid

Solubility

The test article, glycoursodeoxycholic acid, was soluble up to 50,000 μM in methanol and to 100 μM in assay buffers, with a final 0.5% methanol content (v:v) at all concentrations tested.

Stability

Stability of 1 and 10 μM glycoursodeoxycholic acid was determined in glass vials before and after freezing once, and after freezing and thawing aliquots in an assay plate three times. The test article was tested in transport buffer alone or with 0.002% PS-80 or 1% HSA to assess recovery. The data

TABLE 23

Stability of glycoursodeoxycholic acid in HBSS with 10 mM HEPES, pH 7.4, with or without excipients, after freezing in glass vials or after 3 freeze-thaw cycles in assay plates

| | Glycoursodeoxycholic acid (μM) | | Percent Recovery[a] | |
|---|---|---|---|---|
| | | | Glass Vials 1 freeze- | Assay Plates[b] 3 freeze-thaw |
| Buffer | Nominal | Actual[a] | thaw | cycles |
| sHBSS | 1 | 0.765 | 84.1 | 93.8 |
| sHBSS | 10 | 9.67 | 111 | 132 |
| sHBSS + PS-80 | 1 | 0.818 | 99.8 | 107 |
| sHBSS + PS-80 | 10 | 7.49 | 120 | 137 |
| sHBSS + HSA | 1 | 1.96 | 101 | 100 |
| sHBSS + HSA | 10 | 21.3 | 94.8 | 98.4 |

HBSS Hank's Balanced Salt Solution.
HEPES N-(2-hydroxyethyl)piperazine-N'-(2-ethanesulfonic acid).
HSA 1% human serum albumin.
PS-80 0.002% polysorbate-80.
sHBSS HBSS with 10 mM HEPES, pH 7.4.
[a]Average of two replicates, unless otherwise noted.
[b]Mean of three replicates.

Non-Specific Binding

Non-specific binding of glycoursodeoxycholic acid to the transwell assay plate in the absence of cells was also evaluated. Glycoursodeoxycholic acid solutions (1 and 10 μM) were placed in the apical (250 μL) or basolateral (700 μL) chambers (donor chambers) of a transwell plate in triplicate wells, with matching blank buffer in the receiver chambers, and were incubated at 37° C. for 2 hours. Data are presented in Table 24, below. In transport buffer alone, the recovery was ≥138% in the apical to basolateral direction and ≥85.3% in the basolateral to apical direction. In transport buffer containing 0.002% PS-80, the recovery was ≥81.7% in the apical to basolateral direction and ≥99.1% in the basolateral to apical direction. In transport buffer containing 1% HSA, the recovery was ≥140% in the apical to basolateral direction and ≥68.4% in the basolateral to apical direction.

TABLE 24

Recovery of glycoursodeoxycholic acid after incubation in a transwell plate in the absence of Caco-2 cells at 37° C. for 2 hours

| | | Percent Recovery | | | |
|---|---|---|---|---|---|
| | | A to B | | B to A | |
| Buffer | Treatment | Mean[a] | SD | Mean[a] | SD |
| sHBSS | GA (1 μM) | 138 | 1.27 | 102 | 9.23 |
| sHBSS | GA (10 μM) | 169 | 18.6 | 85.3 | 1.88 |
| sHBSS + PS-80 | GA (1 μM) | 81.7 | 50.5 | 110 | 0.993 |
| sHBSS + PS-80 | GA (10 μM) | 170 | 11.9 | 99.1 | 1.51 |
| sHBSS + HSA | GA (1 μM) | 150 | 4.00 | 116 | 3.67 |
| sHBSS + HSA | GA (10 μM) | 140 | 15.2 | 68.4 | 1.35 |

A to B Apical to basolateral direction.
B to A Basolateral to apical direction.
GA Glycoursodeoxycholic acid.
HSA 1% human serum albumin.
PS-80 0.002% polysorbate-80.
SD Standard deviation.
sHBSS HBSS with 10 mM HEPES, pH 7.4.
[a]Mean of three replicates.

Based on the stability and non-specific binding results, transporter assays were conducted in transport buffer containing 0.002% PS-80 for best recovery of glycoursodeoxycholic acid under assay conditions.

Assessment of Glycoursodeoxycholic Acid as a Substrate and Inhibitor of BSEP (Using Membrane Vesicles)

The ATP-dependent uptake of glycoursodeoxycholic acid (1 and 10 μM) in BSEP-transfected Sf9 membrane vesicles was tested alone or with the BSEP inhibitor cyclosporine A (20 and the data are presented in Table 25, below. Mean ATP-dependent uptake activity for glycoursodeoxycholic acid at 1 and 10 μM was 11.2 and 14.2 pmol/minute/mg protein, respectively. The signal-to-noise ratio could not be determined as the AMP incubations were below the limit of quantitation. No remaining BSEP activity was noted following treatment with cyclosporine A. These data indicated that glycoursodeoxycholic acid was actively transported and was a substrate of BSEP.

TABLE 25

ATP-dependent uptake of glycoursodeoxycholic acid by BSEP membrane vesicles

| | | Uptake Activity (pmol/minute/ mg protein) | Signal-to-Noise Ratio | | ATP-Dependent Uptake Activity (pmol/minute/mg protein) | |
|---|---|---|---|---|---|---|
| Treatment | Sample | Mean[a] | Mean[a] | SD | Mean[a] | SD |
| GA (1 μM) | Mg-ATP | 11.2 | NA | NA | 11.2 | 0.797 |
| | Mg-AMP | BLQ | | | | |
| GA (1 μM) + Cyclosporine (20 μM) | Mg-ATP | BLQ | NA | NA | NA | NA |
| | Mg-AMP | BLQ | | | | |
| GA (10 μM) | Mg-ATP | 14.2 | NA | NA | 14.2 | 12.9 |
| | Mg-AMP | BLQ | | | | |
| GA (10 μM) + Cyclosporine (20 μM) | Mg-ATP | BLQ | NA | NA | 0.00[b] | NA |
| | Mg-AMP | 6.93 | | | | |

BLQ Below the limit of quantitation.
GA Glycoursodeoxycholic acid.
Mg-AMP Magnesium-adenosine 5'-monophosphate.
Mg-ATP Magnesium-adenosine 5'-triphosphate.
NA Not applicable.
SD Standard deviation.
[a]Mean of three replicates.
[b]Negative percentages reported as zero.

The ATP-dependent uptake of BSEP substrate $^3$-TCA in BSEP vesicles, alone or with cyclosporine A (20 μM) or glycoursodeoxycholic acid (10 and 100 is presented in Table 26, below. Mean ATP-dependent uptake activity for $^3$-TCA was 17.7 pmol/minute/mg protein, with a signal-to-noise ratio of 19.2. The $^3$-TCA uptake decreased to 3.64% in the presence of BSEP inhibitor cyclosporine A. Glycoursodeoxycholic acid inhibited $^3$-TCA uptake, with 10.4% activity remaining at 100 μM; an estimated IC$_{50}$ would be <10 μM.

TABLE 26

ATP-dependent uptake of $^3$H-taurocholic acid by BSEP membrane vesicles in the absence and presence of glycoursodeoxycholic acid and selective inhibitor

| Treatment | Sample | Uptake Activity (pmol/minute/mg protein) Mean$^a$ | Signal-to-Noise Ratio Mean$^a$ | SD | ATP-Dependent Uptake Activity (pmol/minute/mg protein) Mean$^a$ | SD | Percent of Control |
|---|---|---|---|---|---|---|---|
| Control | Mg-ATP | 18.7 | 19.2 | 1.80 | 17.7 | 1.75 | 100 |
| | Mg-AMP | 0.972 | | | | | |
| Cyclosporine A (20 μM) | Mg-ATP | 1.29 | 2.00 | 1.12 | 0.645 | 0.728 | 3.64 |
| | Mg-AMP | 0.648 | | | | | |
| GA (10 μM) | Mg-ATP | 9.35 | 11.9 | 1.20 | 8.56 | 0.944 | 48.3 |
| | Mg-AMP | 0.788 | | | | | |
| GA (100 μM) | Mg-ATP | 2.81 | 2.89 | 0.346 | 1.84 | 0.337 | 10.4 |
| | Mg-AMP | 0.974 | | | | | |

GA Glycoursodeoxycholic acid.
Mg-AMP Magnesium-adenosine 5'-monophosphate.
Mg-ATP Magnesium-adenosine 5'-triphosphate.
SD Standard deviation.
$^a$Mean of three replicates.

CONCLUSIONS

As shown in the examples above, sodium phenylbutyrate was not identified as a substrate of BSEP transporters. Sodium phenylbutyrate (25 and 250 μM) did not inhibit BSEP transporters. Phenylacetic acid (1 and 10 μM) was not identified as a substrate of BSEP transporters. Phenylacetic acid (750 and 7500 μM) inhibited BSEP, showing the potential for drug-drug interactions. Phenylacetyl-L-glutamine was neither a substrate (1 and 10 μM) nor inhibitor (50 and 500 μM) of BSEP transporters. Tauroursodeoxycholic acid (1 and 10 μM) was a substrate of BSEP transporters. Tauroursodeoxycholic acid (5 and 50 μM) inhibited B SEP. The B SEP inhibition interaction exhibited the potential for drug-drug interactions. Ursodeoxycholic acid (1 and 10 μM) was not a substrate of BSEP transporters. Ursodeoxycholic acid (50 and 500 μM) inhibited uptake of the probe substrate for BSEP. Glycoursodeoxycholic acid (1 and 10 μM) was a substrate of BSEP transporters. Glycoursodeoxycholic acid (10 and 100 μM) inhibited B SEP transporters, showing the potential for drug-drug interactions.

What is claimed is:

1. A method of administering Taurursodiol (TURSO) and sodium phenylbutyrate to a human subject having at least one symptom of Amyotrophic Lateral Sclerosis (ALS) who has received a first dosage of cyclosporine, the method comprising:

(a) administering to the human subject a composition comprising about 1 gram of TURSO and about 3 grams of sodium phenylbutyrate,
(b) determining or having determined a first level of serum transaminases and/or bilirubin in a first biological sample from the human subject, and
(c) administering to the human subject a second dosage of cyclosporine, wherein the second dosage is lower than the first dosage, wherein the subject has had onset of at least one symptom of ALS for more than about 24 months, and wherein the first dosage of cyclosporine is about 0.5 to about 15 mg/kg/day.

2. The method of claim 1, further comprising step (d), determining or having determined a second level of serum transaminases and/or bilirubin a second biological sample from the human subject.

3. The method of claim 2, wherein the second level of the serum transaminases and/or bilirubin is lower than the first level.

4. The method of claim 1, wherein the biological sample is a plasma or serum sample.

5. The method of claim 1, wherein the TURSO is administered at an amount of about 1 gram once a day.

6. The method of claim 1, wherein the TURSO is administered at an amount of about 1 gram twice a day.

7. The method of claim 1, wherein the sodium phenylbutyrate is administered at an amount of about 3 grams once a day.

8. The method of claim 1, wherein the sodium phenylbutyrate is administered at an amount of about 3 grams twice a day.

9. The method of claim 1, wherein the composition is administered to the human subject orally or through a feeding tube.

10. The method of claim 1, wherein the human subject is diagnosed with ALS.

11. The method of claim 1, wherein the human subject is suspected as having ALS.

* * * * *

UNITED STATES PATENT AND TRADEMARK OFFICE
CERTIFICATE OF CORRECTION

PATENT NO. : 12,138,272 B2  
APPLICATION NO. : 17/742707  
DATED : November 12, 2024  
INVENTOR(S) : Joshua Cohen and Justin Klee Page 1 of 1

It is certified that error appears in the above-identified patent and that said Letters Patent is hereby corrected as shown below:

On the Title Page

Column 2 (Abstract), Line 6, delete "B SEP" and insert -- BSEP --

Signed and Sealed this  
Twenty-ninth Day of April, 2025

Coke Morgan Stewart  
*Acting Director of the United States Patent and Trademark Office*